US012767994B2

(12) United States Patent
Pouletty et al.

(10) Patent No.: US 12,767,994 B2
(45) Date of Patent: Oct. 20, 2026

(54) BIOMARKERS, AND USES IN TREATMENT OF VIRAL INFECTIONS, INFLAMMATIONS, OR CANCER

(71) Applicants: ABIVAX, Paris (FR); CENTRE NATIONAL DE LA RECHERCHE SCIENTIFIQUE, Paris (FR); INSTITUT CURIE, Paris (FR); UNIVERSITÉ DE MONTPELLIER, Montpellier (FR)

(72) Inventors: Philippe Pouletty, Paris (FR); Hartmut Ehrlich, Paris (FR); Didier Scherrer, Castelnau-le-Lez (FR); Jamal Tazi, Clapiers (FR); Laurent Manchon, Combaillaux (FR)

(73) Assignees: ABIVAX, Paris (FR); CENTRE NATIONAL DE LA RECHERCHE SCIENTIFQUE, Paris (FR); INSTITUT CURIE, Paris (FR); UNIVERSITÉ MONTPELLIER, Montpellier (FR)

( * ) Notice: Subject to any disclaimer, the term of this patent is extended or adjusted under 35 U.S.C. 154(b) by 1082 days.

(21) Appl. No.: 17/416,988

(22) PCT Filed: Dec. 19, 2019

(86) PCT No.: PCT/EP2019/086494
§ 371 (c)(1),
(2) Date: Jun. 21, 2021

(87) PCT Pub. No.: WO2020/127853
PCT Pub. Date: Jun. 25, 2020

(65) Prior Publication Data
US 2022/0145406 A1 May 12, 2022

(30) Foreign Application Priority Data
Dec. 20, 2018 (EP) .................................... 18306784

(51) Int. Cl.
*C12Q 1/68* (2018.01)
*A61K 31/706* (2006.01)
*C12N 15/113* (2010.01)
*C12Q 1/70* (2006.01)

(52) U.S. Cl.
CPC .............. *C12Q 1/70* (2013.01); *A61K 31/706* (2013.01); *C12N 15/1132* (2013.01); *C12N 2310/141* (2013.01)

(58) Field of Classification Search
None
See application file for complete search history.

(56) References Cited

U.S. PATENT DOCUMENTS

| | | | |
|---|---|---|---|
| 2,605,182 A | 7/1952 | Peterson | |
| 4,376,202 A | 3/1983 | Ura et al. | |
| 4,425,343 A | 1/1984 | Sakata et al. | |
| 4,434,290 A | 2/1984 | Bisagni et al. | |
| 4,738,710 A | 4/1988 | Serban et al. | |
| 6,180,632 B1 | 1/2001 | Myers et al. | |
| 7,019,147 B1 | 3/2006 | Barth et al. | |
| 8,394,796 B2 | 3/2013 | Castanedo et al. | |
| 8,933,033 B2 | 1/2015 | Naylor et al. | |
| 8,957,065 B2 | 2/2015 | Cha et al. | |
| 8,962,583 B2 * | 2/2015 | Weiner ................. | C12N 15/113 536/23.1 |
| 9,061,999 B2 | 6/2015 | Tazi et al. | |
| 9,108,919 B2 | 8/2015 | Roux et al. | |
| 9,145,367 B2 | 9/2015 | Tazi et al. | |
| 9,637,475 B2 | 5/2017 | Roux et al. | |
| 9,827,237 B2 | 11/2017 | Tazi et al. | |
| 10,017,498 B2 | 7/2018 | Tazi et al. | |
| 10,253,020 B2 | 4/2019 | Tazi et al. | |
| 10,435,370 B2 | 10/2019 | Tazi et al. | |
| 10,683,284 B2 | 6/2020 | Tazi et al. | |
| 10,981,874 B2 | 4/2021 | Scherrer et al. | |
| 12,202,804 B2 | 1/2025 | Scherrer et al. | |
| 2003/0207886 A1 | 11/2003 | Plucker et al. | |
| 2004/0038969 A1 | 2/2004 | Doherty et al. | |
| 2004/0242603 A1 | 12/2004 | Fujiwara et al. | |
| 2005/0085482 A1 | 4/2005 | Ramurthy et al. | |
| 2005/0119225 A1 | 6/2005 | Schumacher et al. | |
| 2006/0089380 A1 | 4/2006 | Barnham et al. | |
| 2008/0119478 A1 | 5/2008 | Tsubouchi et al. | |
| 2008/0161353 A1 | 7/2008 | Barnham et al. | |
| 2008/0318984 A1 | 12/2008 | Verkman et al. | |
| 2009/0227628 A1 | 9/2009 | Kolczewski et al. | |
| 2010/0167948 A1 | 7/2010 | Krichevsky et al. | |
| 2011/0003843 A1 | 1/2011 | Lejeune et al. | |
| 2011/0111976 A1 | 5/2011 | Fare et al. | |

(Continued)

FOREIGN PATENT DOCUMENTS

| | | |
|---|---|---|
| DE | 958 647 C | 2/1957 |
| EP | 0 394 112 A2 | 10/1990 |

(Continued)

OTHER PUBLICATIONS

Koukos et al; Gastroenterology, vol. 145, pp. 842-852, 2013.*

(Continued)

*Primary Examiner* — Jehanne S Sitton
(74) *Attorney, Agent, or Firm* — Oliff PLC

(57) ABSTRACT

Biomarkers and uses thereof in monitoring, assessing, and/or treatment of viral infections, or inflammatory diseases, disorders, or conditions, or cancer.

5 Claims, 17 Drawing Sheets

Specification includes a Sequence Listing.

(56) References Cited

U.S. PATENT DOCUMENTS

| | | | |
|---|---|---|---|
| 2012/0202870 A1 | 8/2012 | Weiner et al. | |
| 2012/0277230 A1 | 11/2012 | Roux et al. | |
| 2012/0283265 A1 | 11/2012 | Tazi et al. | |
| 2012/0329796 A1 | 12/2012 | Tazi et al. | |
| 2013/0040988 A1 | 2/2013 | Deka et al. | |
| 2013/0267703 A1 | 10/2013 | Tazi et al. | |
| 2014/0051085 A1 | 2/2014 | Ding et al. | |
| 2014/0080831 A1 | 3/2014 | Roux et al. | |
| 2014/0288120 A1 | 9/2014 | Tazi et al. | |
| 2015/0225796 A1 | 8/2015 | Snijders et al. | |
| 2015/0299129 A1 | 10/2015 | Roux et al. | |
| 2015/0307478 A1 | 10/2015 | Tazi et al. | |
| 2015/0361491 A1* | 12/2015 | Tazi .................... | C12Q 1/6876 435/6.12 |
| 2016/0041153 A1 | 2/2016 | Brown et al. | |
| 2017/0204063 A1 | 7/2017 | Tazi et al. | |
| 2017/0226095 A1 | 8/2017 | Tazi et al. | |
| 2018/0030078 A1 | 2/2018 | Scherrer et al. | |
| 2019/0077760 A1 | 3/2019 | Rabe et al. | |
| 2019/0382347 A1 | 12/2019 | Scherrer et al. | |
| 2020/0062713 A1 | 2/2020 | Rabe et al. | |
| 2021/0047273 A1 | 2/2021 | Scherrer et al. | |
| 2021/0087145 A1 | 3/2021 | Tazi et al. | |
| 2022/0023324 A1 | 1/2022 | Pouletty et al. | |

FOREIGN PATENT DOCUMENTS

| | | | |
|---|---|---|---|
| EP | 1 897 914 | A1 | 3/2008 |
| EP | 2 075 309 | A2 | 7/2009 |
| EP | 2 266 972 | A1 | 12/2010 |
| EP | 2465502 | A1 | 6/2012 |
| EP | 2 757 161 | A1 | 7/2014 |
| EP | 2 974 729 | A1 | 1/2016 |
| EP | 3 058 940 | A1 | 8/2016 |
| EP | 3 059 236 | A1 | 8/2016 |
| FR | 2 387 229 | A1 | 11/1978 |
| FR | 2 436 786 | A1 | 4/1980 |
| FR | 2 627 493 | A1 | 8/1989 |
| FR | 2 645 861 | A1 | 10/1990 |
| FR | 2 849 474 | A3 | 7/2004 |
| FR | 2 859 474 | A1 | 3/2005 |
| FR | 2 859 475 | A1 | 3/2005 |
| GB | 585362 | A | 2/1947 |
| GB | 2087387 | A | 5/1982 |
| IN | 554/CHE/2003 | | 4/2005 |
| JP | S52-72821 | A | 6/1977 |
| JP | S56-051454 | A | 5/1981 |
| JP | H09-508642 | A | 9/1997 |
| JP | 2005-507365 | A | 3/2005 |
| JP | 2006-504646 | A | 2/2006 |
| JP | 2006-519846 | A | 8/2006 |
| JP | 2008-519814 | A | 6/2008 |
| JP | 2009-174368 | A | 8/2009 |
| JP | 6378802 | B2 | 8/2018 |
| WO | 95/21613 | A1 | 8/1995 |
| WO | 00/59875 | A2 | 10/2000 |
| WO | 2002/074726 | A2 | 9/2002 |
| WO | 02/083643 | A1 | 10/2002 |
| WO | 03/000660 | A1 | 1/2003 |
| WO | 2003/037866 | A1 | 5/2003 |
| WO | 2004/007461 | A1 | 1/2004 |
| WO | 2004/078731 | A1 | 9/2004 |
| WO | 2004/080463 | A1 | 9/2004 |
| WO | 2005/023255 | A2 | 3/2005 |
| WO | 2005/051302 | A2 | 6/2005 |
| WO | 2005/112930 | A1 | 12/2005 |
| WO | 2006/051311 | A1 | 5/2006 |
| WO | 2006/060318 | A2 | 6/2006 |
| WO | 2006/081444 | A2 | 8/2006 |
| WO | 2007/000876 | A1 | 1/2007 |
| WO | 2007/042899 | A2 | 4/2007 |
| WO | 2007/103162 | A2 | 9/2007 |
| WO | 2007/147217 | A1 | 12/2007 |
| WO | 2008/003864 | A1 | 1/2008 |
| WO | 2008/008234 | A1 | 1/2008 |
| WO | 2008/089459 | A1 | 7/2008 |
| WO | 2008/101935 | A2 | 8/2008 |
| WO | 2008/115870 | A2 | 9/2008 |
| WO | 2008/118468 | A1 | 10/2008 |
| WO | 2008/143440 | A1 | 11/2008 |
| WO | 2009/021696 | A1 | 2/2009 |
| WO | 2009/023844 | A2 | 2/2009 |
| WO | 2009/029617 | A1 | 3/2009 |
| WO | 2009/085234 | A2 | 7/2009 |
| WO | 2009/087238 | A2 | 7/2009 |
| WO | 2009/132273 | A2 | 10/2009 |
| WO | 2010/107965 | A1 | 9/2010 |
| WO | 2010/127208 | A1 | 11/2010 |
| WO | 2010/129451 | A1 | 11/2010 |
| WO | 2010/143168 | A2 | 12/2010 |
| WO | 2010/143169 | A2 | 12/2010 |
| WO | 2010/143170 | A2 | 12/2010 |
| WO | 2010/151755 | A2 | 12/2010 |
| WO | 2011/057003 | A2 | 5/2011 |
| WO | 2012/080953 | A1 | 6/2012 |
| WO | 2014/055944 | A1 | 4/2014 |
| WO | 2014/111892 | A1 | 7/2014 |
| WO | 2015/001518 | A1 | 1/2015 |
| WO | 2015/131019 | A1 | 9/2015 |
| WO | 2016/009065 | A2 | 1/2016 |
| WO | 2016/009066 | A1 | 1/2016 |
| WO | 2016/135052 | A1 | 9/2016 |
| WO | 2016/135055 | A1 | 9/2016 |
| WO | 2017/158201 | A1 | 9/2017 |
| WO | 2020/011810 | A1 | 1/2020 |

OTHER PUBLICATIONS

Pavek et al; "Correlation of miR-124 to extracellular matrix protein MMP-3 in patients with Rheumatoid Arthritis", THU0003, abstract, 2013.*

"HIV-1 isolate R17 from Spain noncoding spliced transcript mRNA sequence," Database EMBL, Database Accession No. GU453421.

Farberov et al., "MicroRNA-mediated regulation of p21 and TASK1 cellular restriction factors enhances HIV-1 Infection," Journal of Cell Science, 2015, vol. 128, pp. 1607-1616.

Manchon et al., "Data Descriptor: RNA sequencing analysis of activated macrophages treated with the anti-HIV ABX464 in intestinal inflammation," Scientific Data, 2017, vol. 4, 170150.

Campos et al., "Long lasting control of viral rebound with a new drug ABX464 targeting Rev—mediated viral RNA biogenesis," Retrovirology, 2015, vol. 12, No. 30, pp. 1-15.

Qin et al., "miRNA-124 in Immune System and Immune Disorders," Frontiers in Immunology, Oct. 2016, vol. 7, Article 406, pp. 1-8.

Balasubramaniam et al., "Are microRNAs Important Players in HIV-1 Infection? An update," Viruses, 2018, vol. 10, No. 110, pp. 1-35.

Vautrin et al., "Both anti-inflammatory and antiviral properties of novel drug candidate ABX464 are mediated by modulation of RNA splicing," Scientific Reports, 2019, vol. 9, No. 792, pp. 1-15.

Feb. 18, 2020 International Search Report issued in International Patent Application No. PCT/EP2019/086494.

Feb. 18, 2020 Written Opinion of the International Searching Authority issued in International Patent Application No. PCT/EP2019/086494.

Jun. 23, 2021 International Search Report issued in International Patent Application No. PCT/EP2021/057123.

Jun. 23, 2021 Written Opinion issued in International Patent Application No. PCT/EP2021/057123.

Milewska et al. "Entry of Human Coronavirus NL63 into the Cell", Journal of Virology, vol. 92 No. 3. (2017), 16 pages.

Yang et al. "miR-124 attenuates Japanese encephalitis virus replication by targeting DNM2", Virology Journal, vol. 13 No. 1. (2016), 10 pages.

Liu et al. "The potential role of IL-6 in monitoring severe case of coronavirus disease 2019", medRxiv. (2020), 24 pages.

"NCT04393038: ABX464 in Treating Inflammation and Preventing Acute Respiratory Failure in Patents with Covid-19", p. 1-4 (2020).

(56) References Cited

OTHER PUBLICATIONS

U.S. Appl. No. 17/913,063, filed Sep. 20, 2022 in the name of Tazi et al.
Feb. 2, 2024 Office Action issued in Chinese Patent Application No. 201980092774.2.
Laurent Manchon et al., "Data Descriptor: RNA sequencing analysis of activated macrophages treated with the anti-HIV ABX464 in intestinal inflammation", Scientific Data, www.nature.com/sdata/, (2017), pp. 1-11.
Guo, et al., "Haplotype Distribution and Evolutionary Pattern of miR-17 and miR-124 Families Based on Population Analysis", PLoS ONE, vol. 4, Issue 11, 2009.
Hernandez-Lopez et al., "Alternative splicing in human tumour viruses: a therapeutic target?" Biochemical Journal, 2012, Biochemical Society, vol. 445, pp. 145-156.
Hofmann et al., "Htra2-β1 Stimulates an Exonic Splicing Enhancer and can Restore Full-length SMN Expression to Survival Motor Neuron 2 (SMN2)," PNAS, 2000, vol. 97, No. 17, pp. 9618-9623.
Hostyn et al. "Synthesis of ?- Carbolines Starting from 2,3-Dichloropyridines and Substituted Anilines." Advanced Synthesis & Catalysis, Wiley, vol. 350, Oct. 2008, pp. 2653-2660.
Houzet, et al., "MicroRNAs and human retroviruses," Biochimica et Biophysica Acta, 1809(11-12), pp. 686-693, 2011.
Huang-Kai Peng et al., "Synthesis and anti-HCV activity evaluation of anilinoquinoline derivatives," Bioorganic & Medicinal Chemistry Letters, vol. 22, 2012, pp. 1107-1110.
J. Tazi et al., "Alternative Splicing and Disease," Biochimica et Biophysica Acta, 1792 (2009), 14-26.
J. Wei et al., "miR-124 Inhibits STAT3 Signaling to Enhance T Cell-Mediated Immune Clearance of Glioma," Cancer Research, vol. 73, No. 13, Jul. 1, 2013, pp. 3913-3926.
J. Zugazagoitia et al. "Current Challenges in Cancer Treatment." Clinical Therapeutics, vol. 38, No. 7, May 2016, pp. 1551-1566.
Johnson et al., "Genome-Wide Survey of Human Alternative Pre-mRNA Splicing with Exon Junction Microarrays," Science, vol. 302, pp. 2141-2144, 2003.
Jonckers et al. "Selective Palladium-Catalyzed Aminations of Dicholoropyridines," Tetrahedron, 2001, vol. 57, pp. 7027-7034.
Kaczmarek et al. "Synthesis and Antineoplastic Properties of Some Benzoiso-.Alpha.-Carbolines". Archiv Der Pharmazie, Weinheim, Germany, vol. 321, No. 8, pp. 463-467, 1988.
Katoh et al. "Isolation of the intermediates and improved synthesis of pyrido[1',2': 1 ,2]imidazo[4, 5b]pyrazines and-quinoxalines", Heterocycles, 1992, 34(10), p. 1965-1972.
Khalifa. "Hutchinson-Gilford Progeria Syndrome: Report of a Libyan Family and Evidence of Autosomal Recessive Inheritance". Clinical Genetics, vol. 35, pp. 125-132, 1989.
Kher Samir et al., "Microwave Mediated Dearylation of 2-Aryloxy-5-Nitropyridine," Research Journal of Chemical Sciences, vol. 1, No. 6, Sep. 2011, pp. 84-87.
Kim, et al., "Processing of intronic microRNAs", EMBO Journal, vol. 26, No. 3, pp. 775-783, 2007.
Klinck, et al., "Multiple Alternative Splicing Markers for Ovarian Cancer", Cancer Research, vol. 68, No. 3, pp. 657-663, 2008.
Kondratenko et al. "Bactericidal Activity of Some Derivatives of N-Heteroaromatic Compounds". Mikrobiologichnii Zhurnal, 1934-1977, vol. 40, No. 3, pp. 368-370 (abstract only), 1978.
Labourier et al. "Recognition of Exonic Splicing Enhancer Sequences by the *Drosophila* Splicing Repressor RSF1". Nucleic Acids Research, vol. 27, No. 11, pp. 2377-2386, 1999.
Lai, et al., "Micro RNAs are complementary to 3' UTR sequence motifs that mediate negative post-transcriptional regulation", Nature Genetics, vol. 30, No. 4, pp. 363-364, 2002.
Lee, et al., "MicroRNA maturation: stepwise processing and subcellular localization", EMBO Journal, vol. 21, No. 17, pp. 4663-4670, 2002.
Lin Min et al., "Nonsense-mediated mRNA decay and tumors," Journal of International Pathology and Clinical Medicine, vol. 26, No. 4, pp. 291-294.
Lindow, et al., "Principles and Limitations of Computational MicroRNA Gene and Target Finding", DNA and Cell Biology, vol. 26, No. 5, pp. 339-351, 2007.
Litvickji, P.F. Pathophysiology. Moscow. GEOTAR-MED, vol. 1, 2003, pp. 142-144, 192-200.
Liu et al. "Partial Correction of Endogenous DF508 CFTR in Human Cystic Fibrosis Airway Epithelia by Spliceosome-Mediated RNA Trans-Splicing". Nature Biotechnology, vol. 20, pp. 47-52, 2002.
Liu, et al., "The evolution and functional diversification of animal microRNA genes", Cell Research, vol. 18, No. 10, pp. 985-996, 2008.
Longping Yao et al. "MicroRNA-124 regulates the expression of MEKK3 in the inflammatory pathogenesis of Parkinson's disease." Journal of Neuroinflammation, vol. 15, No. 13, 2016, pp. 1-19.
Marc Fakhoury et al. "Inflammatory bowel disease: clinical aspects and treatments." Journal of Inflammation Research, Dovepress, Jun. 2014, pp. 113-120.
"MicroRNA-124 Deactivates Human HIV-1-Infected and Classically Activated Macrophages/microglia: Implication for Neurogenesis. ," J. Neuroimmune Pharmacol (2012), vol. 7, Suppl. 1, pp. S75-S76.
O.A. Yanborisova et al., "Derivatives of 2-aminocinchoninic acids: synthesis and antiinflammatory activity," Pharmaceutical Chemistry Journal, vol. 2B, No. 1, 1994, pp. 29-31.
O.A. Yanborisova et al., "Synthesis and antiinflammatory activity of 2-arylaminocinchoninic acids and amides of 1,2-dihydro-2-oxocinchoninic acid," Pharmaceutical Chemistry Journal, vol. 29, No. 6, Jun. 1995, pp. 32-33.
O.A. Yanborisova et al., "Synthesis and study of antiinflammatory and nd analgesic activity of 2-arylaminocinchoninic acid hydrazides and β-(1-carboxyethylidene)hydrazides." Pharmaceutical Chemistry Journal, vol. 31, No. 6, Jun. 1997, pp. 309-310.
Rolak, Clin Med Res, Jan. 2003, vol. 1 (1), 57-60. (Year: 2003).
Ruth M. Murray et al., "The Nitration of Some Aryloxy-2- and -4-methylquinoline. Syntheses of Substanes having possible Antimalarial Action," Journal of the Chemical Society, 1934, pp. 856-860.
S.-L. Tang et al. "MiR-124 regulates osteoblast differentiation through GSK-3? in ankylosing spondylitis." European Review for Medical and Pharmacological Sciences, vol. 22, 2018, pp. 6616-6624.
S.D. Carter et al. "Quinoxalines and Related Compounds-X: The Formation of Indolo[2,3-b]Quinoxalines and 2-p-Aminophenyl-3-Anilinoquinoxalines from 2-Anilinoquinoxalines." Tetrahedron, Pergamon Press, vol. 34, Issue No. 7, 1978, pp. 981-988.
Saari, R., et al. "Microwave-assisted synthesis of quinoline, isoquinoline, quinoxaline and quinazoline derivatives as CB2 receptor agonists." Bioorganic & Medicinal Chemistry. Elservier. vol. 19, Jan. 2011, pp. 939-950.
Scott D. Kuduk et al., "Amiloride derived inhibitors of acid-sensing ion channel-3 (ASIC3)," Bioorganic & Medicinal Chemistry Letters, vol. 19, 2009, pp. 2514-2518.
STN Database Registration No. 374598-11-5, Chemical Abstracts Service, American Chemical Society, Registered Oct. 1, 2007, pp. 1-10.
STN Database Registration No. 933238-11-0, Chemical Abstracts Service, American Chemical Society, Registered Apr. 29, 2007, pp. 1-4.
Tatyana Veremeyko et al. "IL-4/IL-13-Dependent and Independent Expression of miR-124 and Its Contribution to M2 Phenotype of Monocytic Cells in Normal Conditions and during Allergic Inflammation." Plos One, vol. 8, No. 12, 2013, 13 pages.
Wang, et al., "Quantitation of mRNA by the polymerase chain reaction", Proc. Natl. Acad. Sci., vol. 86, pp. 9717-9721, 1989.
Witwer, et al., "Relationships of PBMC microRNA expression, plasma viral load, and CD4+ T-cell count in HIV-1-infected elite suppressors and viremic patients", Retrovirology, vol. 9, No. 1, 2012.
Wong, et al., "Real-time PCR for mRNA quantitation", BioTechniques, vol. 39, No. 1, pp. 75-85, 2005.
Xueying Li et al. "Long non-coding RNA NEAT1 overexpression associates with increased exacerbation risk, severity, and inflammation, as well as decreased lung function through the interaction

(56) References Cited

OTHER PUBLICATIONS with microRNA-124 in asthma." Journal of Clinical Laboratory Analysis, vol. 34, No. 1, 2019, 9 pages.
Yueyuan Xiao et al. "miR124-3p/FGFR2 axis inhibits human keratinocyte proliferation and migration and improve the inflammatory microenvironment in psoriasis." Molecular Immunology, vol. 122, 2020, pp. 89-98.
Zeng, et al., "Epigenetic regulation of miR-124 by Hepatitis C Virus core protein promotes migration and invasion of intrahepatic cholangiocarcinoma cells by targeting SMYD3", FEBS Letters, vol. 586, No. 19, pp. 3271-3278, 2012.
Zhen Qin et al. "miR-124, a potential therapeutic target in colorectal cancer." OncoTargets and Therapy, Dovepress, Dec. 2019, pp. 749-751.
Zhibo Yang et al. "MicroRNA-124 alleviates chronic skin inflammation in atopic eczema via suppressing innate immune responses in keratinocytes." Cellular Immunology, vol. 319, 2017, pp. 53-60.
"Abivax sets its course on colitis and Crohn's." Pharmaphorum, pp. 1-3. Sep. 4, 2018.
CAS Registry No. 438481-24-4 added on STN on Jul. 12, 2002.
CAS Registry No. 933238-11-0 added on STN on Apr. 29, 2007.
Connor et al., "Vpr is Required for Efficient Replication of Human Immunodeficiency Virus type-1 in Mononuclear Phagocytes," Virology, 1995, vol. 206, pp. 935-944.
Cottet et al., "Recommendable Routes to Trifluoromethyl-Substituted Pyridine-and Quinolinecarboxylic Acids," Eur. J. Org. Chem., 2003, pp. 1559-1568.
Database CAS Registry of RN 1019446-43-5. Retreived 2020.
Database CAS Registry of RN 1094714-12-1. Retreived 2020.
Database CAS Registry of RN 1457614-02-6. Retreived Feb. 2020.
Database CAS Registry of RN 1548036-82-3. Retreived 2020.
Database CAS Registry of RN 1556532-05-8. Retreived Feb. 2020.
Database CAS Registry of RN 298216-45-2. Retreived 2020.
Database CAS Registry of RN 338749-91-0. Retreived Feb. 2020.
Database CAS Registry of RN 338750-07-5, RN 338749-97-6, and RN 338417-00-8 (2001).
Database CAS Registry of RN 448932-63-6. Retreived Feb. 2020.
Database CAS Registry of RN 478032-29-0. Retreived Feb. 2020.
Database CAS Registry of RN 926207-30-9. Retreived 2020.
De Sandre-Giovannoli et al. "Lamin a Truncation in Hutchinson-Gilford Progeria". Science, vol. 300, p. 2055, 2003.
De Sandre-Giovannoli et al., "Altered Splicing in Prelamin A-associated Premature Aging Phenotypes," Progress in Molecular and Subcellular Biology, 2006, pp. 199-232.
Derrick D. Eichele et al. "Dextran sodium sulfate colitis murine model: An indispensable tool for advancing our understanding of inflammatory bowel diseases pathogenesis." World Journal of Gastroenterology, No. 33, vol. 23, Sep. 2017, pp. 6016-6029.
Desai et al., "2-Methyl-4-quinoline-hydrazide Derivatives as Antitubercular/Antibacterial Agents—Part I," Asian Journal of Chemistry, vol. 10, No. 2, (1998), pp. 370-372.
Desai et al., "Some Quinoline, Quinazoline and Pyrazine Derivatives as Antitubercular-Antibacterial Agents," Asian Journal of Chemistry, vol. 10, No. 4 (1998), pp. 993-994.
Deuerlein, "Dipryridyl-, diquinolyl-, and Pyridylquinolylamines," Journal fuer Praktische Chemie (Liepzig), 1923, vol. 106, pp. 53-65.
Dhanabal et al., "Heteroatom Directed Photoannulation: Synthesis of Indoloquinoline Alkaloids: Cryptolepine, Cryptotackieine, Cryptosanguinolentine, and their Methyl Derivatives," Tetrahedron, 2006, vol. 62, pp. 6258-6263.
Dignam et al., "Eukaryotic Gene Transcription with Purified Components," Methods in Enzymology, 1983, vol. 101, pp. 582-598.
Dobson, J. et al., "Attempts to find new antimalarials. XXVII. Derivatives of various benzacridines and pyridoacridines", Journal of the Chemical Society, pp. 123-126, Jan. 1948.
Ducrocq et al., "Synthesis of 10-substituted 5H-pyrido[3', 4':4,5]pyrrolo[2,3-]isoquinolines," Journal of the Chemical Society, Perkin Transactions 1: Organic and Bio-Organic Chemistry (1972-1999), 1979, vol. 1, pp. 142-145.
Dudash et al., "Synthesis and Evaluation of 3-anilio-quinoxalinones as glycogen phosphorlyase inhibitors", Bioorganic & Medicinal Chemistry Letters, 15(21), p. 4790-4793, 2005.
Edwards et al., "Orf-I and Orf-II-Encoded Proteins in HTLV-1 Infection and Persistence", Viruses, 2011, MDPI, vol. 3, pp. 861-885.
El-Sayed et al. "Synthesis of Some Novel Quinoline-3-Carboxylic Acids and Pyrimidoquinoline Derivatives as Potential Antimicrobial Agents". Archiv der Pharmize, vol. 335, No. 9, pp. 403-410, 2002.
Etukala et al., "A Short and Convenient Synthesis and Evaluation of the Antiinfective Properties of Indoloquinoline Alkaloids: 10H-Indolo[3,2-b]quinoline and 7H-Indolo[2,3-c]quinolines," Journal of Heterocyclic Chemistry, No. 45, Mar. 2008, pp. 507-511.
Ewing et al., "Analysis of Expressed Sequence Tags Indicates 35,000 Human Genes," Nature Genetics, 2000, vol. 25, pp. 232-234.
F. J. Leinweber, "Possible Physiological Roles of Carboxylic Ester Hydrolases," Drug Metabolism Reviews, vol. 18, No. 4, pp. 379-439, 1987.
Fangfang Jin et al. "Serum microRNA Profiles Serve as Novel Biomarkers for Autoimmune Diseases." Frontiers in Immunology, vol. 9, Art. 2381, Oct. 2018, pp. 1-9.
Fengmao An et al. "MiR-124 acts as a target for Alzheimer's disease by regulating BACE1." Oncotarget, No. 69, vol. 8, 2017, pp. 114065-114071.
File Registry on STN, 101350-67-8, entered on Apr. 5, 1986.
File Registry on STN, 195876-33-6/RN, entered on Oct. 23, 1997.
File Registry on STN, 408510-56-5, entered on Apr. 29, 2002.
File Registry on STN, 55360-88-8, entered on Nov. 16, 1984.
File Registry on STN, 67412-46-8, entered on Nov. 16, 1984.
File Registry on STN, 70125-24-5/RN, entered on Nov. 16, 1984.
File Registry on STN, 92873-44-4, entered on Dec. 7, 1984.
File Registry on STN, 94541-69-2, entered on Feb. 3, 1985.
File Registry on STN, 97978-62-6, entered on Sep. 16, 1985.
Fong et al., "A Protein Farnesyltransferase Inhibitor Ameliorates Disease in a Mouse Model of Progeria," Science, 2006, vol. 311, pp. 1621-1623.
Fors et al., "An Efficient Process for Pd-Catalyzed C—N Cross-Coupling Reactions of Aryl Iodides: Insight Into Controlling Factors," J. Am. Chem. Soc., 2009, 131, 5766-5768.
G. Bhattancharjee et al. "Synthesis of physiologically important quinoxaline derivatives using conventional method and microwave irradiation." Indian Journal of Chemical Technology, Council of Scientific & Industrial Research, vol. 15, No. 1, Jan. 2008, pp. 72-74.
Gordon et al., "Hutchinson-Gilford Progeria Syndrome," NCBI Bookshelf, 2003, accessed http://www.ncbi.nlm.gov/books/NBK1121/ on Jan. 26, 2016, 21 pages.
Graveley, "Sorting out the Complexity of SR Protein Functions," RNA, 2000, vol. 6, pp. 1197-1211.
Gritsenko et al., "Synthesis in Phenothiazines. XXXIX. Dimethylpyridophenothiazines," Khimiya Geterotsiklicheskikh Soedinenii, 1975, vol. 1, pp. 50-54 (abstract).
Grout et al., "Polyazabenzo[a]pyrenes," Journal of the Chemical Society [Section] C: Organic, 1968, vol. 21, pp. 2689-2693.
Jan. 22, 2016 Search Report issued in International Patent Application No. PCT/EP2015/066458.
Eugene D. Ponomarev et al., "MicroRNA-124 Promotes Microglia Quiescence and Suppresses EAE by Deactivating Macrophages via the C/EBP-α-PU.1 Pathway", Nature Medicine, vol. 17, No. 1, Jan. 2011, pp. 64-71.
Yang Sun et al., "MicroRNA-124 Mediates the Cholinergic Anti-Flammatory Action Throught Inhibiting the Production of Pro-Inflammatory Cytokines", Cell Research, vol. 23, No. 11, (2013), pp. 1270-1283.
Alsaidi H et al., "Convenient Synthesis of Heteroaryl Phenyl Ethers from Chloropyridines and Chloroquinolines Using Phase-Transfer Catalysis", Synthesis, Georg Thieme Verlag, Stuttgart, DE, No. 11, (1980), pp. 921-924.
Jan. 3, 2019 U.S. Office Action issued in U.S. Appl. No. 15/326,755.
A. Simacek et al. "Preparation and Reactivity of 3-Amino-2,4-dichloroquinoline." Synlett, vol. 23, 2012, pp. 2205-2208.

(56) References Cited

OTHER PUBLICATIONS

A.K. El-Damasy et al. "Novel 5-substituted-2-anilinoquinolines with 3-(morpholino or 4-methylpiperazin-1-yl)propoxy moiety as broad spectrum antiproliferative agents: Synthesis, cell based assays and kinase screening." Bioorganic & Medicinal Chemistry Letters, vol. 26, No. 14, May 2016, pp. 3307-3312.
A.L. Wilson et al. "New Trends in Anti-Cancer Therapy: Combining Conventional Chemotherapeutics with Novel Immunomodulators." Current Medicinal Chemistry, vol. 25, No. 36, Dec. 2018, pp. 4758-4784.
Altuvia, et al., "Clustering and conservation patterns of human microRNAs", Nucleic Acids Research, 2005, vol. 33, No. 8, pp. 2697-2706, 2005.
Andreassi et al., "Aclarubicin Treatment Restores SMN Levels to Cells Derived from Type 1 Spinal Muscular Atrophy Patients," Human Molecular Genetics, 2001, vol. 10, No. 24, pp. 2841-2849.
Antonella Amoruso et al. "Immune and central nervous system-related miRNAs expression profiling in monocytes of multiple sclerosis patients." Nautre: Scientific Reports, vol. 10, Art. 6125, 2020, URL: https://doi.org/10.1038/s41598-020-63282-3.
Apr. 27, 2020 Office Action issued in U.S. Appl. No. 16/554,748.
Audrey Vautrin et al. "Both anti-inflammatory and antiviral properties of novel drug candidate ABX464 are mediated by modulation of RNA splicing." Nautre: Scientific Reports, vol. 9, Art. 792, 2019, URL: https://doi.org/10.1038/s41598-018-37813-y.
Bakkour et al., "Small-Molecule Inhibition of HIV pre-mRNA Splicing as a Novel Antiretroviral Therapy to Overcome Drug Resistance," PLOS Pathogens, 2007, vol. 3, issue 10, pp. 1530-1539.
Baklanov et al., "Photocyclization of (o-haloaryl)hetarylamines," Zhurnal Organicheskoi Khimii, 1991, vol. 27, No. 3, pp. 638-649 (abstract).
Balkau et al., "Syntheis of Ellipticine Intermediates: 6-Amino-, 6-hydroxy-, and 6-Methoxy-5,8-Dimethylisoquinoline," Australian. J. Chem., 1969, vol. 22, pp. 2489-2492.
Bartel, et al., "MicroRNAs: Target Recognition and Regulatory Functions", Cell, vol. 136, No. 2, pp. 215-233, 2009.
Baskerville, et al., "Microarray profiling of microRNAs reveals frequent coexpression with neighboring miRNAs and host genes", RNA, vol. 11, No. 3, pp. 241-247, 2005.
Belikov, V.G. Pharmaceutical Chemistry. Moscow. MEDpress-inform, 2007, pp. 27-29.
Bisset et al., "Combined effect of zidovudine (ZDV), lamivudine (3TC) and abacavir (ABC) antiretoviral therapy in suppressing in vitro FIV replication," Antiviral Research, 2002, Elsevier, vol. 53 pp. 35-45.
Black, "Mechanisms of Alternative Pre-Messenger RNA Splicing," Annu. Rev. Biochem., 2003, vol. 72, pp. 291-336.
Boganyi et al., "Syntheses of New Quinoline-Containing Heterocyclic Scaffolds Using Inter- and Intramolecular Pd-Catalyzed Amination," Journal of Heterocyclic Chemistry, 2009, vol. 46, No. 1, pp. 33-38.
Brandt et al., "Uncoupling activity and physicochemical properties of derivatives of fluazinam," Biochimica et Biophysica Acta, Protein Structure and Molecular Enzymology, 1101(1): 41-7, 1992, abstract only CA 117:82915.
Brune et al., "Progeria: A New Kind of Laminopathy—Clinical and Molecular Update of the Hutchinson-Gilford Syndrome," 1st European Symposium, 2003.
Buchmann et al., "The Preparation and Reactivity of 4-hydroxy-7-chloroquinaldine," Journal fuer Praktische Chemie, 1962, vol. 17, pp. 135-146 (abstract).
Bustin, "Absolute quantification of mRNA using real-time reverse transcription polymerase chain reaction assays", Journal of Molecular Endocrinology, vol. 25, pp. 169-193, 2000.
CAPLUS Record for Loriga et al., "Part 7." (Retrieved Nov. 2013).
CAPLUS Record for Loriga et al., "Part 8." (Retrieved Nov. 2013).
Cartegni et al., "Correction of Disease-associated Exon Skipping by Synthetic Exon-specific Activators," Nature Structural Biology, 2003, vol. 10, No. 2, pp. 120-125.
Cartegni et al., "Listening to Silence and Understanding Nonsense: Exonic Mutations that Affect Splicing," Nature Reviews—Genetics, Apr. 2002, vol. 3, pp. 285-298.
Carter et al., "Quinoxalines and related compounds-X-1", Tetrahedron, 34(7), p. 981-988, 1978.
CAS (Chemical Abstracts Service) Registry No. 1011408-51-7, American Chemical Society, added on STN on Apr. 1, 2008, 1 page.
CAS (Chemical Abstracts Service) Registry No. 92873-44-4, American Chemical Society, added on STN on Dec. 7, 1984, 1 page.
CAS (Chemical Abstracts Service) Registry No. 94541-69-2, American Chemical Society, added on STN on Feb. 3, 1985, 1 page.
CAS Registry No. 138386-77-3 added on STN on Jan. 17, 1992.
CAS Registry No. 204851-25-2 added on STN on Apr. 30, 1998.
CAS Registry No. 215589-34-7 added on STN on Dec. 15, 1998.
CAS Registry No. 294668-01-2 added on STN on Oct. 11, 2000.
CAS Registry No. 313266-85-2 added on STN on Jan. 9, 2001.
CAS Registry No. 324526-73-0 added on STN on Feb. 27, 2001.
CAS Registry No. 342653-87-6 added on STN on Jun. 20, 2001.
CAS Registry No. 449780-94-3 added on STN on Sep. 12, 2002.
CAS Registry No. 449780-95-4 added on STN on Sep. 12, 2002.
CAS Registry No. 5468-85-9 added on STN on Nov. 16, 1984.
CAS Registry No. 70682-97-2 added on STN on Nov. 16, 1984.
CAS Registry No. 1004363-48-7 added on STN on Feb. 19, 2008.
CAS Registry No. 1011408-51-7 added on STN on Apr. 1, 2008.
CAS Registry No. 1135230-99-7 added on STN on Apr. 16, 2009.
CAS Registry No. 330663-16-6 added on STN on Apr. 10, 2001.
CAS Registry No. 374598-11-5 added on STN on Dec. 10, 2001.
Chebli et al. "The Anti-HIV Candidate Abx464 Dampens Intestinal Inflammation by Trigerring IL-22 Production in Activated Macrophages." Scientific Reports, vol. 7, No. 4860, pp. 1-11. 2017.
Oct. 26, 2021 Office Action issued in U.S. Appl. No. 17/113,369.
Oct. 29, 2021 Office Action issued in U.S. Appl. No. 16/994,954.
Feb. 6, 2018 Office Action issued in U.S. Appl. No. 15/326,755.
Jan. 3, 2019 Office Action issued in U.S. Appl. No. 15/326,755.
Jun. 8, 2018 Office Action issued in U.S. Appl. No. 15/326,755.
Nov. 14, 2019 English Translation of Office Action issue in Russian Patent Application No. 2017101407/04.
Jul. 19, 2021 Office Action issued in U.S. Appl. No. 16/994,954.
Mar. 24, 2020 International Search Report issued in International patent Application No. PCT/EP2019/086470.
May 23, 2019 European Search Report issued in European Patent Application No. 18306783.
U.S. Appl. No. 16/787,471, filed Feb. 11, 2020 in the name of Tazi et al.
U.S. Appl. No. 14/761,674, filed Jul. 17, 2015 in the name of Tazi et al.
U.S. Appl. No. 17/113,369, filed Dec. 7, 2020 in the name of Tazi et al.
Sep. 23, 2022 Office Action Issued In U.S. Appl. No. 17/113,369.
Sep. 28, 2022 Office Action Issued in U.S. Appl. No. 16/994,954.
Mar. 10, 2023 Office Action issued in U.S. Appl. No. 17/416,856.
Aberg, Judith A. "Aging, inflammation, and HIV infection." Topics in antiviral medicine 20.3 (2012): 101.
Gavegnano, C. et al. "Ruxolitinib and tofacitinib are potent and selective inhibitors of HIV-1 replication and virus reactivation in vitro." Antimicrobial Agents and Chemotherapy; vol. 58; No. 4; pp. 1977-1986; 2014.
Sep. 25, 2023 Office Action issued in U.S. Appl. No. 17/416,856.
English Translation of the Feb. 2, 2024 Office Action issued in Chinese Patent Application No. 201980092774.2.
Dan Wang et al., "Activation of PPAR? inhibits pro-inflammatory cytokines production by upregulation of miR-124 in vitro and in vivo", Biochemical and Biophysical Research Communications 486, (2017), pp. 726-731.
Nakamachi et al., "MicroRNA-124a Is a Key Regulator of Proliferation and Monocyte Chemoattractant Protein 1 Secretion in Fibroblast-like Synoviocytes From Patients With Rheumatoid Arthritis," Arthritis & Rheumatism, 2009, vol. 60, No. 5. p. 1294-1304.
Koukos et al., "MicroRNA-124 Regulates STAT3 Expression and is Downregulated in Colon Tissues of Pediatric Patients with Ulcerative Colitis," Gastroenterology, 2013.
CAS Registry No. 10562-04-6 added on STN on Nov. 16, 1984.
CAS Registry No. 208661-32-9 added on STN on Jul. 19, 1998.

(56) References Cited

OTHER PUBLICATIONS

U.S. Appl. No. 18/973,608, filed Dec. 9, 2024 in the name of Tazi et al.
Jun. 5, 2025 Non-Final Rejection received in U.S. Appl. No. 17/913,063.
Oct. 1, 2025 Office Action issued in U.S. Appl. No. 17/913,063.
J. August. "Veterinary Clinics of North America: Small Animal Practice", vol. 14, No. 5, Sep. 1984.
Li et al. "Nature Reviews Drug Discovery", vol. 19, Mar. 2020.

* cited by examiner

B

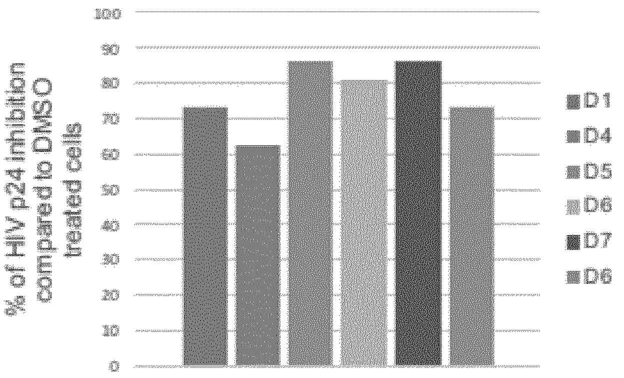

C

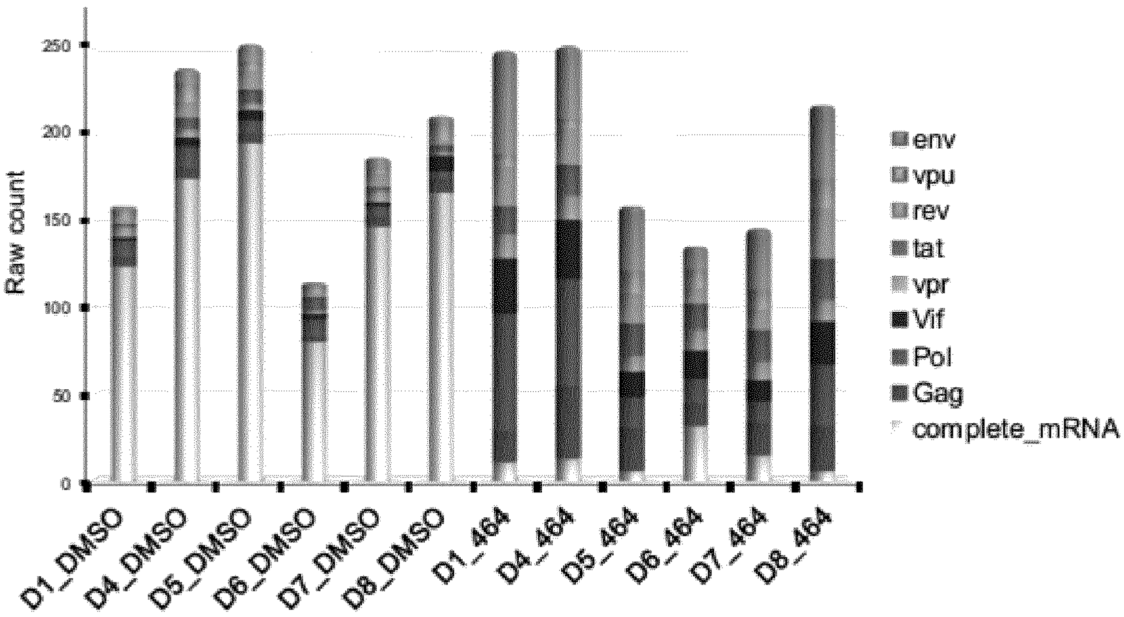

D

| | |
|---|---|
| New putative mRNA sequence | GGAAAATCTCTAGCAGTGGCGCCCGAACAGGGACTTGAAAGCGAAA GGAAAACCAGAGGAGCTCTCTCGACGCAGGACTCGGCTTGCTGAAG CGCGCACGGCAAGAGGCGAGGGGCGGCGACTGGAAGAAGCGGAG ACAGCGACGAAGACCTCCTCAGGACAGTCAGACTCATCAAAGTTCTC TATCAAAGCA (SEQ. ID. NO. 1) |
| Exon 1: 615-739 | GGAAAATCTCTAGCAGTGGCGCCCGAACAGGGACTTGAAAGCGAAA GGAAAACCAGAGGAGCTCTCTCGACGCAGGACTCGGCTTGCTGAAG CGCGCACGGCAAGAGGCGAGGGGCGGCGACTG (SEQ. ID. NO. 2) |
| Exon 2: 5976-6045 | GAAGAAGCGGAGACAGCGACGAAGACCTCCTCAGGACAGTCAGACT CATCAAAGTTCTCTATCAAAGCA (SEQ. ID. NO. 3) |

Figure 1B, C, D

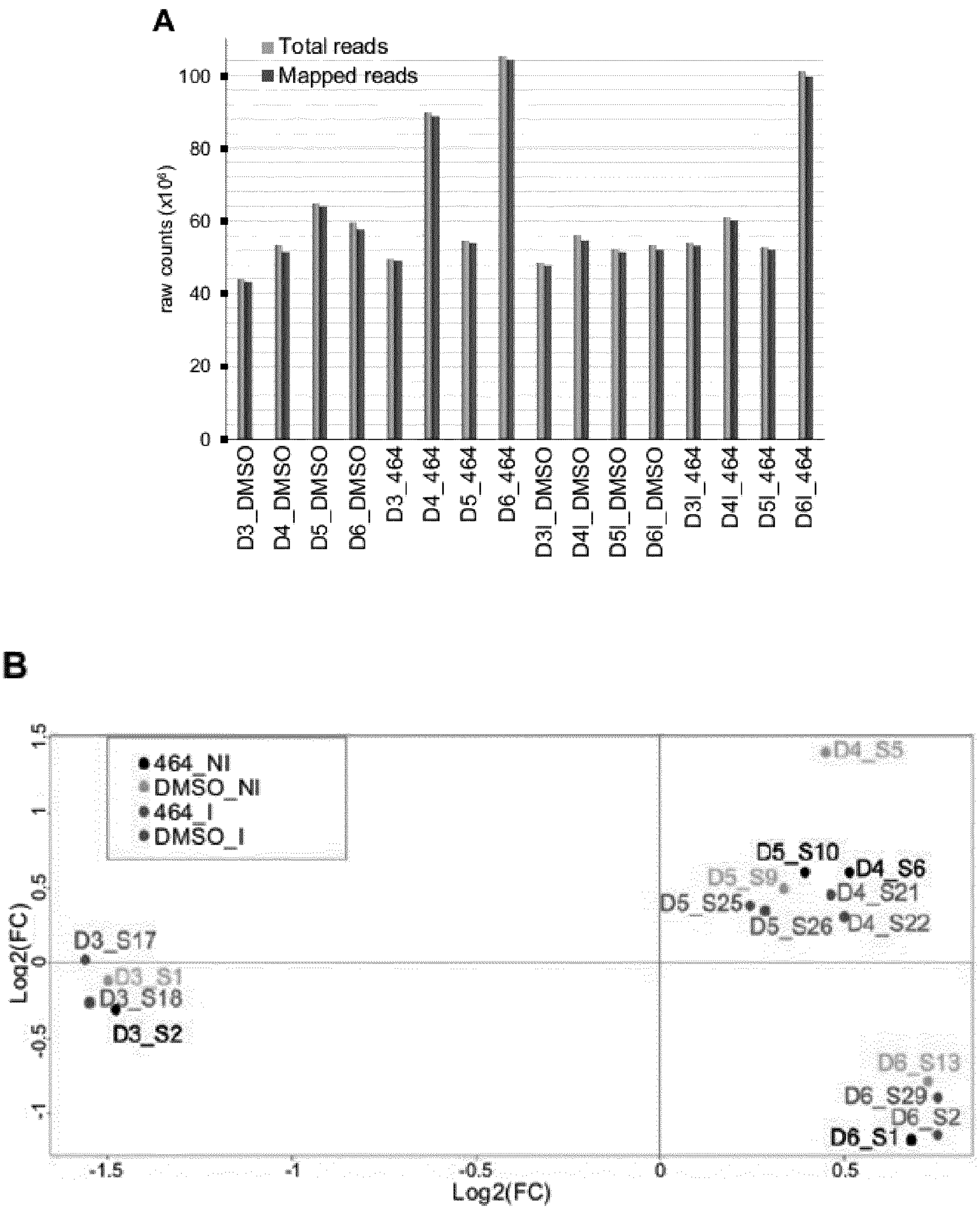
Figure 2A, B

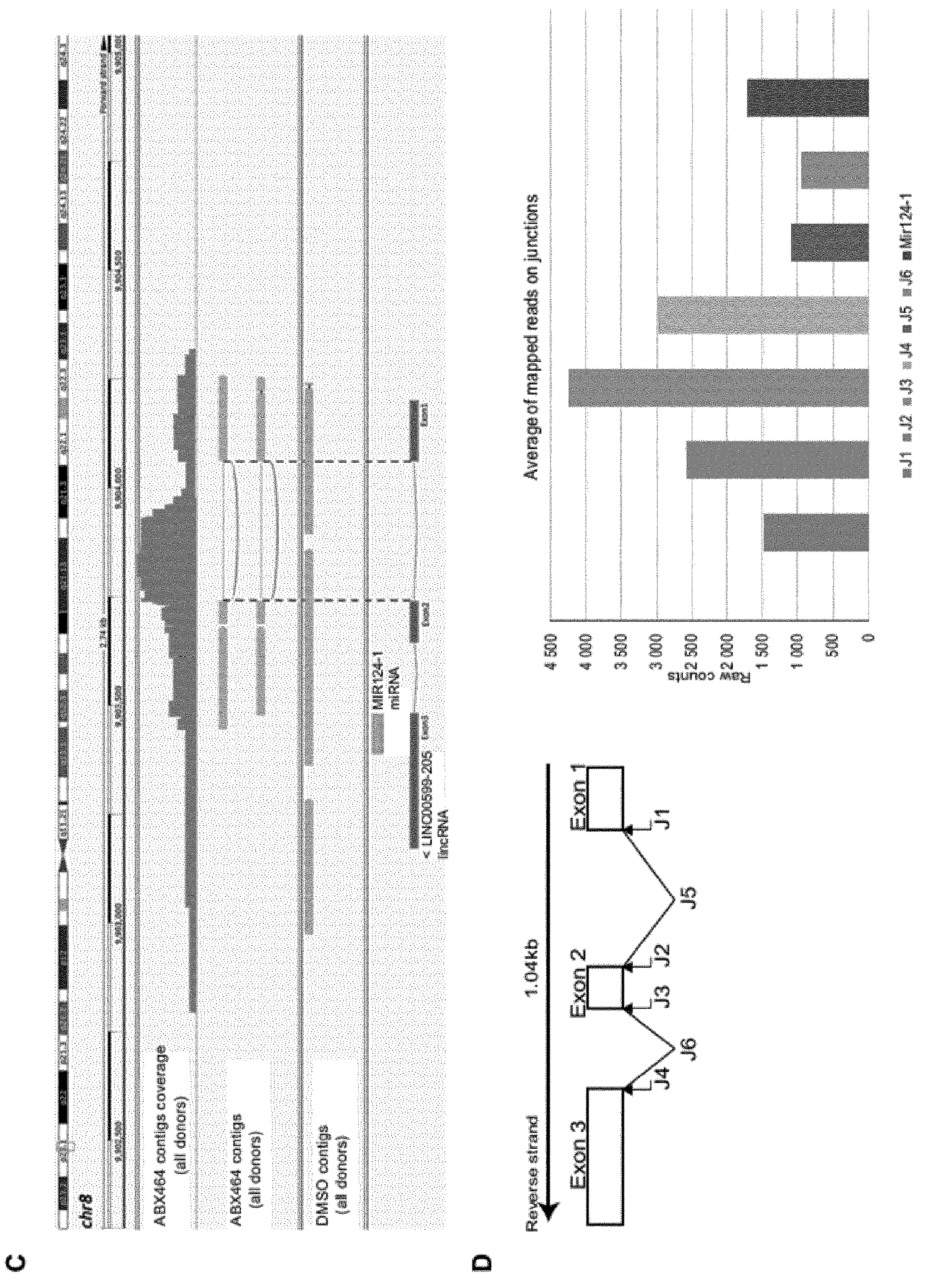
Figure 4C, D

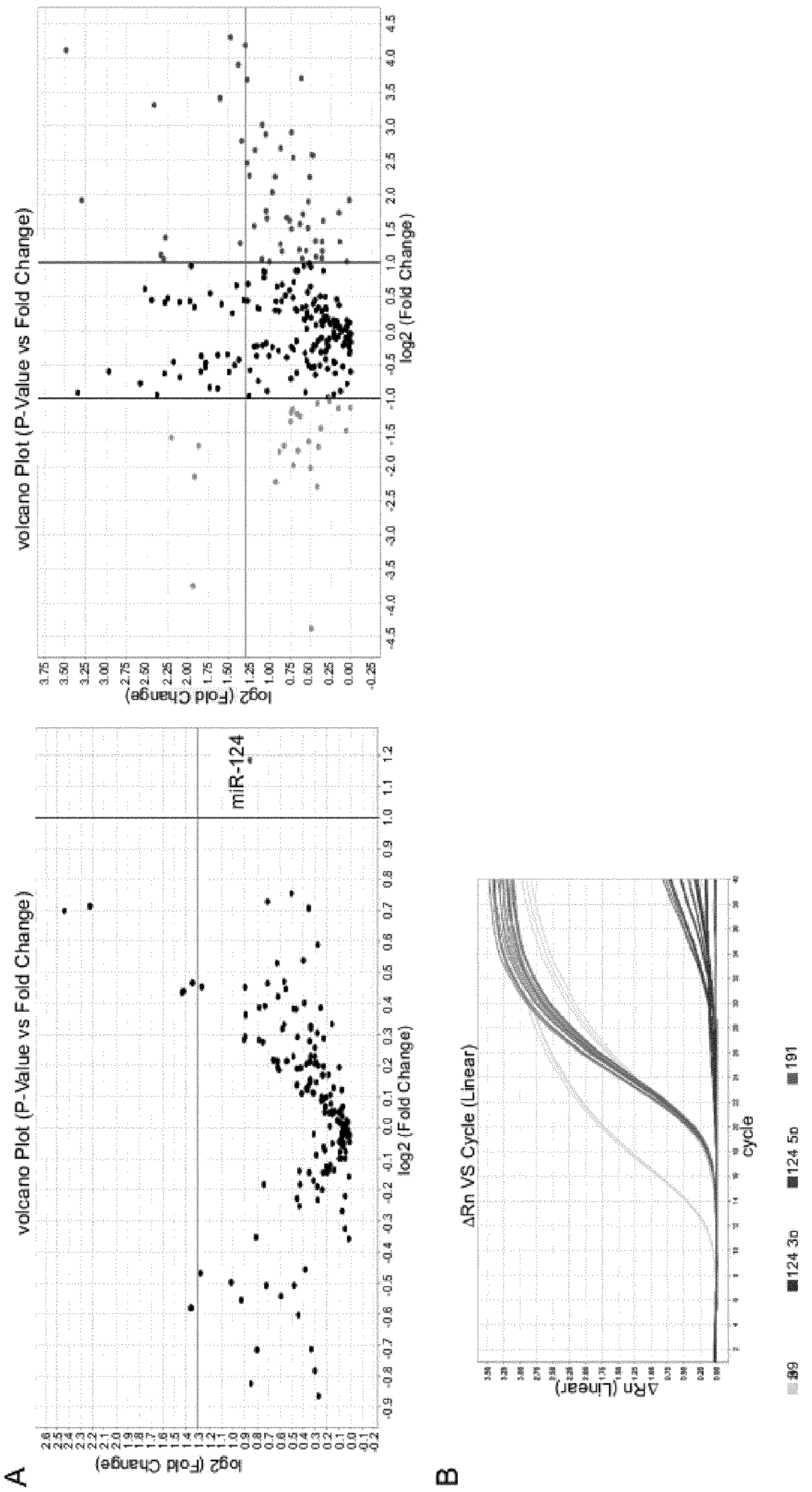
Figure 9A, B

SEQUENCE LISTING

<160> NUMBER OF SEQ ID NOS: 18

<210> SEQ ID NO 1
<211> LENGTH: 193
<212> TYPE: RNA
<213> ORGANISM: Homo sapiens
<220> FEATURE:
<223> OTHER INFORMATION: New putative mRNA sequence

<400> SEQUENCE: 1
ggaaaatctc tagcagtggc gcccgaacag ggacttgaaa gcgaaaggaa aaccagagga 60
gctctctcga cgcaggactc ggcttgctga agcgcgcacg gcaagaggcg aggggcggcg 120
actggaagaa gcggagacag cgacgaagac ctcctcagga cagtcagact catcaaagtt 180
ctctatcaaa gca 193

<210> SEQ ID NO 2
<211> LENGTH: 124
<212> TYPE: RNA
<213> ORGANISM: Homo sapiens
<220> FEATURE:
<223> OTHER INFORMATION: Exon 1: 615-739

<400> SEQUENCE: 2
ggaaaatctc tagcagtggc gcccgaacag ggacttgaaa gcgaaaggaa aaccagagga 60
gctctctcga cgcaggactc ggcttgctga agcgcgcacg gcaagaggcg aggggcggcg 120
actg 124

<210> SEQ ID NO 3
<211> LENGTH: 69
<212> TYPE: RNA
<213> ORGANISM: Homo sapiens
<220> FEATURE:
<223> OTHER INFORMATION: Exon 2: 5976-6045

<400> SEQUENCE: 3
gaagaagcgg agacagcgac gaagacctcc tcaggacagt cagactcatc aaagttctct 60
atcaaagca 69

<210> SEQ ID NO 4
<211> LENGTH: 23
<212> TYPE: RNA
<213> ORGANISM: Homo sapiens
<220> FEATURE:
<223> OTHER INFORMATION: Consensus 3'ss sequence

<400> SEQUENCE: 4
ugucccuuuu uuuuccacag cug 23

<210> SEQ ID NO 5
<211> LENGTH: 23
<212> TYPE: RNA
<213> ORGANISM: Homo sapiens
<220> FEATURE:
<223> OTHER INFORMATION: Exon1-Exon2 3'ss sequence

<400> SEQUENCE: 5
uccuccuuuc cuuuccucag gag 23

<210> SEQ ID NO 6
<211> LENGTH: 22
<212> TYPE: RNA
<213> ORGANISM: Homo sapiens

<220> FEATURE:
<223> OTHER INFORMATION: Exon2-Exon3 3'ss sequence

<400> SEQUENCE: 6
uccuccuuuc cuuccucagg ag 22

<210> SEQ ID NO 7
<211> LENGTH: 18
<212> TYPE: DNA
<213> ORGANISM: Artificial Sequence
<220> FEATURE:
<223> OTHER INFORMATION: Primer total lncRNA 599-205 Fwd

<400> SEQUENCE: 7
ccctccacca cttgggac 18

<210> SEQ ID NO 8
<211> LENGTH: 20
<212> TYPE: DNA
<213> ORGANISM: Artificial Sequence
<220> FEATURE:
<223> OTHER INFORMATION: Primer total lncRNA 599-205 Rev

<400> SEQUENCE: 8
gacctgggga ttcagccttc 20

<210> SEQ ID NO 9
<211> LENGTH: 22
<212> TYPE: DNA
<213> ORGANISM: Artificial Sequence
<220> FEATURE:
<223> OTHER INFORMATION: Primer unspliced lncRNA 599-205 Fwd

<400> SEQUENCE: 9
gaacaaagag cctttggaag ac 22

<210> SEQ ID NO 10
<211> LENGTH: 18
<212> TYPE: DNA
<213> ORGANISM: Artificial Sequence
<220> FEATURE:
<223> OTHER INFORMATION: Primer unspliced lncRNA 599-205 Rev

<400> SEQUENCE: 10
ggaagggacc acagcatc 18

<210> SEQ ID NO 11
<211> LENGTH: 19
<212> TYPE: DNA
<213> ORGANISM: Artificial Sequence
<220> FEATURE:
<223> OTHER INFORMATION: Primer spliced lncRNA 599-205 Fwd

<400> SEQUENCE: 11
cactcagcga tggaggaaa 19

<210> SEQ ID NO 12
<211> LENGTH: 25
<212> TYPE: DNA
<213> ORGANISM: Artificial Sequence
<220> FEATURE:
<223> OTHER INFORMATION: Primer spliced lncRNA 599-205 Rev

<400> SEQUENCE: 12
ccaatcacac agacaatgag ataac 25

<210> SEQ ID NO 13
<211> LENGTH: 22
<212> TYPE: DNA
<213> ORGANISM: Artificial Sequence
<220> FEATURE:
<223> OTHER INFORMATION: Primer internal control β-actin Fwd

<400> SEQUENCE: 13
gtgaaggtga cagcagtcgg tt 22

<210> SEQ ID NO 14
<211> LENGTH: 21
<212> TYPE: DNA
<213> ORGANISM: Artificial Sequence
<220> FEATURE:
<223> OTHER INFORMATION: Primer β-actin Rev

<400> SEQUENCE: 14
gaagtggggt ggcttttagg a 21

<210> SEQ ID NO 15
<211> LENGTH: 1164
<212> TYPE: RNA
<213> ORGANISM: Homo sapiens
<220> FEATURE:
<223> OTHER INFORMATION: lncRNA 0599-205

<400> SEQUENCE: 15
tcttcttcct ctctctctct ctctctctgt ctctctctct ctcgtctctc ttcctttccc 60
ccctccacca cttgggacct gagcgagagg actgcagcag gcgagttccg gaaggctgaa 120
tccccaggtc ccagccccgg accgcggcaa ctcgcccctg cggcacgccc ggcccggctg 180
cgcccccact cagcgatgga ggtaaagagg cggcggccgc gcgccctgcc ccggctgccg 240
ctgccgagtc cccgctgctc tccttgtcct tcgctctctt cttcctcctc ctagtcccct 300
tcagtttcct gggcgaagca gagggcgaca tgggtgggtg ggttgctgcg ctggggcgag 360
gtggggtcga tgttgttttt tcattgtctg gagctgcagg ggaggcgagg cgcggggaaa 420
ggggcgaggg gagccggggt aattaacacg ggggaggcac ccctccgtct cccacttcca 480
cccacacccc catccctcca ccccctccgc tttgcaggaa aaagcctgga tgcgaaagga 540
tgggggagaa caaagagcct ttggaagacg tcgctgttat ctcattgtct gtgtgattgg 600
gggagctgcg gcggggagga tgctgtggtc ccttcctccg gcgttcccca cccccatccc 660
tctccccgct gtcagtgcgc acgcacacgc gccgcttttt atttcttttt cctggttttc 720
ttattccatc ttctacccac ccctcttcct ttctttcacc tttccttcct tccttcctcc 780
tttccttcct caggagaaag gcctctctct ccgtgttcac agcggacctt gatttaaatg 840
tccatacaat taaggcacgc ggtgaatgcc aagaatgggg ctggctgagc accgtgggtc 900
ggcgagggcc cgccaaggaa ggagcgaccg accgagccag gcgccctccg cagacctccg 960
cgcagcggcc gcgggcgcga ggggaggggt ctggagctcc ctccggctgc ctgtcccgca 1020
ccggagcccg tggggtgggg aggtgtgcag cctgtgacag acaggggctt agagatgcaa 1080
acagactcag ggagagaaac agaagctgat tctgtgacag aagcagatct gtgcagcaca 1140
gatgcggtgt gcgtggggag gggg 1164

<210> SEQ ID NO 16
<211> LENGTH: 141
<212> TYPE: RNA
<213> ORGANISM: Homo sapiens -continued
<220> FEATURE:
<223> OTHER INFORMATION: Exon 1 lncRNA

<400> SEQUENCE: 16
ccctccacca cttgggacct gagcgagagg actgcagcag gcgagttccg gaaggctgaa 60
tccccaggtc ccagccccgg accgcggcaa ctcgcccctg cggcacgccc ggcccggctg 120
cgcccccact cagcgatgga g 141

<210> SEQ ID NO 17
<211> LENGTH: 93
<212> TYPE: RNA
<213> ORGANISM: Homo sapiens
<220> FEATURE:
<223> OTHER INFORMATION: Exon 2 lncRNA

<400> SEQUENCE: 17
gaaaaagcct ggatgcgaaa ggatggggga gaacaaagag cctttggaag acgtcgctgt 60
tatctcattg tctgtgtgat tgggggagct gcg 93

<210> SEQ ID NO 18
<211> LENGTH: 311
<212> TYPE: RNA
<213> ORGANISM: Homo sapiens
<220> FEATURE:
<223> OTHER INFORMATION: Exon 3 lncRNA

<400> SEQUENCE: 18
gagaaaggcc tctctctccg tgttcacagc ggaccttgat ttaaatgtcc atacaattaa 60
ggcacgcggt gaatgccaag aatggggctg gctgagcacc gtgggtcggc gagggcccgc 120
caaggaagga gcgaccgacc gagccaggcg ccctccgcag acctccgcgc agcggccgcg 180
ggcgcgaggg gaggggtctg gagctccctc cggctgcctg tcccgcaccg gagcccgtgg 240
ggtggggagg tgtgcagcct gtgacagaca ggggcttaga gatgcaaaca gactcaggga 300
gagaaacaga a 311

BIOMARKERS, AND USES IN TREATMENT OF VIRAL INFECTIONS, INFLAMMATIONS, OR CANCER

BACKGROUND OF THE INVENTION

A quinoline derivative, 8-chloro-N-(4-(trifluoromethoxy) phenyl)quinolin-2-amine (also known as "ABX464"), binds to the cap binding complex (CBC), a complex at the 5'-end of the pre-mRNA transcript that promotes the initial interaction with transcription and processing machinery. The CBC recruits several factors to m7G-modified transcripts to mediate processing events and is required for efficient cellular and viral pre-mRNA splicing. The interaction of CBC with the U1 snRNP at the 5' splice site of the first intron in the transcript and direct interaction of CBC with proteins in U4/U5/U6 particles enhances the formation of spliced mRNAs. Although CBC is not essential for viability in either yeast or humans, its deletion results in a reduction in the recruitment of several splicing factors to the nascent transcript, resulting in inhibition of cotranscriptional spliceosome assembly. The CBC complex has also been shown to affect biogenesis of microRNA (miRNA), miRNAs are transcribed by RNA pol II as primary (pri)-miRNAs, which carry the m7G cap. During nuclear and cytoplasmic processing events, the pri-miRNA loses the m7G cap, and the mature, 21-23-nucleotide-long miRNA is incorporated into RISC (RNA-induced silencing complex) to guide RNA silencing. Since a large fraction of miRNA genes are located in introns, the CBC complex may be involved in the interplay between the processing of intronic pre-miRNAs and pre-mRNAs. inhibits viral replication by affecting the biogenesis of viral RNA but its effect on cellular and viral RNA biogenesis has not been analyzed in detail. ABX464 will only act on viral replication once proviral DNA was integrated to cellular DNA. This is important as the viral genome, once integrated in infected cells, requires both activation and inhibition of precursor mRNA splicing. Successful infection and production of new infectious HIV particles requires the balanced expression of seven viral proteins (Rev, Tat, Nef, Vif, Vpr, Vpu and Env) that are produced by splicing of the HIV-1 primary 9 kilobases (kb) transcript; among these, the Tat and Rev factors are essential for viral gene expression at the transcriptional and posttranscriptional levels in infected cells. The HIV-1 primary transcript serves not only as genomic RNA for progeny virus but also as the mRNA that encodes the viral Gag and Gag-Pol proteins. While most cellular unspliced RNAs are retained in the nucleus, where they are degraded, nuclear export of the unspliced viral RNAs is facilitated by the Rev protein through binding to the Rev responsive element (RRE) and interaction with CRM1-dependent export machinery. Therefore, inefficient alternative splicing is required to maintain a balance between HIV gene expression and viral production. This balance is thought to be mediated by the HIV long terminal repeat (LTR) and the presence of suboptimal viral 5' and 3' splice sites (5' and 3' ss), which are positively regulated by regulatory sequences and their recognition by cognate trans-acting cellular factors. By binding the CBC complex. ABX464 has been shown to interfere with Rev-mediated export of unspliced RNA. However, the underlying mechanisms behind modulation of viral and cellular splicing and/or miRNA biogenesis by the binding of ABX464 to CBC are presently unknown.

ABX464 has shown strong anti-inflammatory effects in the DSS-model for inflammatory bowel disease (IBD), and effects in preventing HIV virus replication. ABX464 has also demonstrated safety and efficacy in a phase 2a proof-of-concept clinical trial in patients with ulcerative colitis. However, the effect of ABX464 on viral and cellular RNA biogenesis has not been quantified.

SUMMARY OF THE INVENTION

It has now been found that ABX464 changes viral RNA splicing but not cellular splicing, and induces splicing of a long noncoding RNA at miR-124 locus, which leads to upregulation of the anti-inflammatory miR 124. By "miR-124 locus", it is meant any one of the miR-124 locus, which includes miR-124-1 locus, miR-124-2 locus, miR-124-3 locus. Hence, the methods and uses involving miR-124 or one of its locus, as a biomarker, which are disclosed herein can be also, or further, applied to any one of the particular locus known to the skilled in the Art.

Accordingly, in one aspect, the present invention provides an in vitro or ex vivo use of a spliced viral RNA variant, as a biomarker of a viral infection, or of an efficacy of a therapeutic treatment of said viral infection. In some embodiments, the present invention provides a method of using a spliced viral RNA variant as a biomarker of a viral infection, or of an efficacy of a therapeutic treatment of said viral infection, which comprises measuring a presence or an expression level of a spliced viral RNA variant in a biological sample. In some embodiments, a treatment of a viral infection comprises administering a compound, or a pharmaceutically acceptable salt thereof, as described herein.

In another aspect, the present invention provides an in vitro or ex vivo use of a spliced long noncoding RNA at miR-124 locus, as a biomarker of an inflammatory disease, disorder, or condition, or a cancer, or of an efficacy of a therapeutic treatment of said inflammatory disease, disorder, or condition, or said cancer. In some embodiments, the present invention provides a method of using a spliced long noncoding RNA at miR-124 locus as a biomarker of an inflammatory disease, disorder, or condition, or a cancer, or of an efficacy of a therapeutic treatment of said inflammatory disease, disorder, or condition, or said cancer, which comprises measuring a presence or an expression level of a spliced long noncoding RNA at miR-124 locus in a biological sample. In some embodiments, a treatment of an inflammatory disease, disorder, or condition, or a cancer, comprises administering a compound, or a pharmaceutically acceptable salt thereof, as described herein.

In one aspect, the invention relates to an in vitro or ex vivo use of an HIV splice variant of SEQ. ID. No. 1, as a biomarker of an HIV infection, or of an efficacy of a therapeutic treatment of an HIV infection.

In one aspect, the invention relates to an in vitro or ex vivo use of an HIV splice variant of SEQ. ID. No. 1, as a biomarker for assessing biological effect of a compound on treating an HIV infection.

In one aspect, the invention relates to an in vitro or ex vivo use of an HIV splice variant of SEQ. ID. No. 1, as a biomarker for screening a compound or a vaccine in preventing and/or treating an HIV infection.

In one aspect, the invention relates to an in vitro or ex vivo use of a splicing variant lncRNA 0599-205 at the miR-124-1 locus, as a biomarker of an inflammatory disease, disorder, or condition, or a cancer, or of an efficacy of a therapeutic treatment of an inflammatory disease, disorder, or condition, or cancer.

In one aspect, the invention relates to an in vitro or ex vivo use of a splicing variant lncRNA 0599-205 at the miR-124-1 locus, as a biomarker for assessing biological effect of a compound or a medical device on treating an inflammatory disease, disorder, or condition, or a cancer.

In one aspect, the invention relates to an in vitro or ex vivo use of a splicing variant lncRNA 0599-205 at the miR-124-1 locus, as a biomarker for selecting a patient for a therapeutic treatment of an inflammatory disease, disorder, or condition, or a cancer.

In one aspect, the invention relates to an in vitro or ex vivo use of miR-124, as a biomarker of an inflammatory disease, disorder, or condition, or a cancer, or of an efficacy of the therapeutic treatment.

In one aspect, the invention relates to an in vitro or ex vivo use of miR-124, as a biomarker for selecting a patient for a therapeutic treatment of an inflammatory disease, disorder, or condition, or a cancer.

In one aspect of the in vitro or ex vivo uses as defined above, the therapeutic treatment comprises the administration of a compound of formula I, Ia, Ib, Ib', Ic, Id or IV, IVa, IVb, IVb', IVc, IVd, IV; such as ABX464, or a pharmaceutically acceptable salt thereof.

In one aspect of the in vitro or ex vivo uses as defined above, the compound is of formula I, Ia, Ib, Ib', Ic, Id or IV, IVa, IVb, IVb', IVc, IV; such as ABX464, or a pharmaceutically acceptable salt thereof.

In one aspect of the in vitro or ex vivo uses as defined above, the measured level of expression of said HIV splice variant of SEQ. ID. No. 1, or said splicing variant lncRNA 0599-205 at the miR-124-1 locus, or said miR-124 into an isolated biological sample is compared to a control reference value.

DETAILED DESCRIPTION OF CERTAIN EMBODIMENTS

Figure 1A:
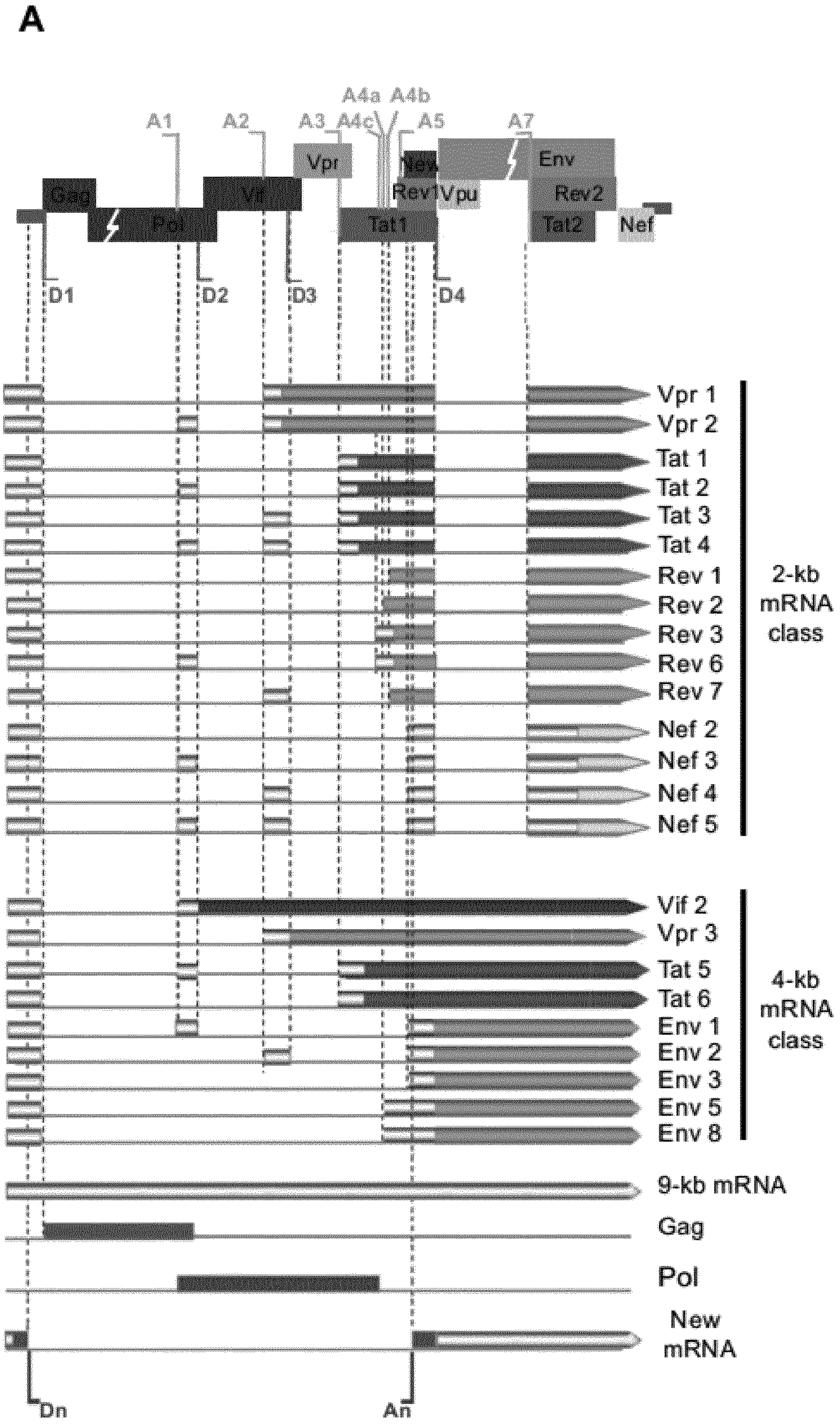
FIG. 1 depicts analysis of HIV splicing following ABX464 treatment. A. Organization of the HIV-1 genome and different mRNA splicing products. The 5' ss (D1-D4) and 3' ss (A1-A7) are indicated. ORFs of the coding exons of each mRNA product are indicated with a different color code indicating the corresponding encoded proteins of the HIV genome. The non-coding exons are boxed in gray. B. Inhibition of HIV-1 replication measured by p24 production in PBMCs from six donors. C. Quantification of HIV splicing events using RNA CaptureSeq in PBMCs from six different donors that were infected and untreated (DMSO) or treated with ABX464 for 6 days (464). Counts of spliced and unspliced contigs are shown. The different splicing products are colored as in A. D. Sequence of the new viral RNA generated by splicing.

1. Exemplary Embodiments of Biomarkers and Uses Thereof

It is now found that the effect of ABX464 in treating HIV infection and IBD are mediated through the same mechanism i.e. enhanced pre-mRNA splicing. ABX464 is found to not only enhance pre-mRNA splicing of HIV viral RNA to block HIV replication, but also to trigger the splicing of a long non-coding RNA which houses one of the loci for the anti-inflammatory miR-124 and thereby to increase the expression of the anti-inflammatory microRNA miR-124. Additionally, ABX464 is found to have no effects on pre-mRNA splicing of cellular genes. While ABX464 has no effect on pre-mRNA splicing of cellular genes, depletion of CBC complex by RNAi leads to accumulation of intron retention transcripts. These results imply that ABX464 did not inhibit the function of CBC in splicing but rather strengthens it under pathological condition like inflammation and HIV infection.

Viral Infections

In some embodiments, the present invention provides a method of using a spliced viral RNA variant as a biomarker of a viral infection, or of an efficacy of a therapeutic treatment of said viral infection, which comprises measuring a presence or an expression level of a spliced viral RNA variant in a biological sample.

In some embodiments, the present invention provides a method of assessing biological effect of a compound on treating a vial infection, which comprises measuring a presence or an expression level of a spliced viral RNA variant as a biomarker of the viral infection.

In some embodiments, the present invention provides a method of screening a compound or a vaccine in preventing and/or treating a viral infection, which comprises measuring a presence or an expression level of a spliced viral RNA variant as a biomarker of the viral infection.

In some embodiments, the present invention provides a method of treating a viral infection, which comprises measuring and/or monitoring a presence and/or an expression level of a spliced viral RNA variant as a biomarker of the viral infection.

In some embodiments, a viral infection is a viral infection which requires RNA splicing. In some embodiments, a viral infection requiring RNA splicing is a retroviral infection. In some embodiments, a retroviral infection is an infection of oncoviruses, lentiviruses, and/or spumaviruses.

As used herein, "oncoviruses" are associated with cancers and malignant infections. In some embodiments, an oncovirus is selected from leukemogenic viruses (such as the avian leukemia virus (ALV), the murine leukemia virus (MULV), also called Moloney virus, the feline leukemia virus (FELV), human leukemia viruses such as HTLV1 and HTLV2, the simian leukemia virus or STLV, the bovine leukemia virus or BLV, the primate type D oncoviruses, the type B oncoviruses which are inducers of mammary tumors, and oncoviruses which cause a rapid cancer (such as the Rous sarcoma virus or RSV).

As used herein, "spumaviruses" manifest fairly low specificity for a given cell type or a given species, and they are sometimes associated with immunosuppressive phenomena. In some embodiments, a spumaviruse is the simian foamy virus (or SFV).

As used herein, "lentiviruses" are responsible for slow progressing pathological conditions which very frequently involve immunosuppressive phenomena, including AIDS.

In some embodiments, a retroviral infection is an HIV and AIDS-related condition. In some embodiments, an HIV and AIDS-related condition is an AIDS-related or AIDS-comorbid inflammatory disorder or condition.

In some embodiments, a presence or an expression level of a spliced viral RNA variant is measured using RNA and/or DNA amplification, sequencing, isotopes, fluorescence, chromogenic enzymes, spectroscopy, spectrometry, immunoassay, or immuno-enzymatic assays.

As described herein, ABX464 is found to generate a new HIV splice variant in HIV infected cells (FIG. 1D):

```
                                        (SEQ. ID. No. 1)
GGAAAATCTCTAGCAGTGGCGCCCGAACAGGGACTTGAA

AGCGAAAGGAAAACCAGAGGAGCTCTCTCGACGCAGGAC

TCGGCTTGCTGAAGCGCGCACGGCAAGAGGCGAGGGGCG

GCGACTGGAAGAAGCGGAGACAGCGACGAAGACCTCCTC

AGGACAGTCAGACTCATCAAAGTTCTCTATCAAAGCA.
```

Accordingly, in some embodiments, a spliced viral RNA variant is an HIV splice variant as a biomarker of an HIV infection. In some embodiments, an HIV splice variant is of SEQ. ID. No. 1.

In some embodiments, the present invention provides a method of using an HIV splice variant of SEQ. ID. No. 1, as a biomarker of an HIV infection, or of an efficacy of a therapeutic treatment of an HIV infection, which comprises measuring a presence or an expression level of the HIV splice variant of SEQ. ID. No. 1 in a biological sample.

In some embodiments, a presence of the HIV splice variant of SEQ. ID. No. 1 in an isolated biological is indicative of an efficacy of a therapeutic treatment of an HIV infection.

In some embodiments, a measured expression level of the HIV splice variant of SEQ. ID. No. 1 in an isolated biological sample is compared to a measured expression level of the HIV splice variant of SEQ. ID. No. 1 in a previously isolated biological sample, and wherein an increase in expression level of the HIV splice variant of SEQ. ID. No. 1 is indicative of an efficacy of a therapeutic treatment of an HIV infection.

In some embodiments, the present invention provides a method of assessing biological effect of a compound on treating an HIV infection, which comprises measuring a presence or an expression level of the HIV splice variant of SEQ. ID. No. 1 as a biomarker of an HIV infection.

In some embodiments, the present invention provides a method of screening a compound or a vaccine in preventing and/or treating an HIV infection, which comprises measuring a presence or an expression level of the HIV splice variant of SEQ. ID. No. 1 as a biomarker of an HIV infection.

In some embodiments, the present invention provides a HIV splice variant comprising SEQ. ID. No. 1. In some embodiments, the present invention provides a composition comprising a HIV splice variant, which comprises SEQ. ID. No. 1. In some embodiments, the present invention provides a biological sample comprising a HIV splice variant, which comprises SEQ. ID. No. 1.

In some embodiments, the present invention provides a HIV splice variant which is the HIV splice variant of SEQ. ID. No. 1. In some embodiments, the present invention provides a composition comprising the HIV splice variant of SEQ. ID. No. 1. In some embodiments, the present invention provides a biological sample comprising the HIV splice variant of SEQ. ID. No. 1.

In some embodiments, the present invention provides a method of treating an HIV infection, which comprises measuring and/or monitoring a presence and/or expression level of the HIV splice variant of SEQ. ID. No. 1 in a patient. In some embodiments, a presence and/or expression level of the HIV splice variant of SEQ. ID. No. 1 is measured in a patient's biological sample. In some embodiments, a patient's biological sample is a blood sample. In some embodiments, a patient's biological sample is a tissue sample. In some embodiments, a method of the present invention for treating an HIV infection further comprises measuring and/or monitoring a presence and/or expression level of the HIV splice variant of SEQ. ID. No. 1 in a patient prior to administering a compound or a pharmaceutically acceptable salt or composition thereof as described herein. In some embodiments, a method of the present invention for treating an HIV infection further comprises measuring and/or monitoring a presence and/or expression level of the HIV splice variant of SEQ. ID. No. 1 in a patient during the course of a treatment with a compound or a pharmaceutically acceptable salt or composition thereof as described herein. In some embodiments, a method of the present invention for treating an HIV infection further comprises selecting a patient for a treatment with a compound or a pharmaceutically acceptable salt or composition thereof as described herein, by measuring and/or monitoring a presence and/or expression level of the HIV splice variant of SEQ. ID. No. 1 in the patient. In some embodiments, a method of the present invention for treating an HIV infection further comprises excluding a patient from a treatment with a compound or a pharmaceutically acceptable salt or composition thereof as described herein, by measuring and/or monitoring a presence and/or expression level of the HIV splice variant of SEQ. ID. No. 1 in the patient. In some embodiments, a method of the present invention for treating an HIV infection further comprises adjusting (such as increasing or decreasing) dosage regimen (such as dose amount and/or dose schedule) of a compound or a pharmaceutically acceptable salt or composition thereof as described herein to be administered to a patient, by measuring and/or monitoring a presence and/or expression level of the HIV splice variant of SEQ. ID. No. 1 in the patient. In some embodiments, a method of the present invention for treating an HIV infection further comprises pausing and/or stopping dosing a compound or a pharmaceutically acceptable salt or composition thereof as described herein, after a measured presence and/or expression level of the HIV splice variant of SEQ. ID. No. 1 reaches a level indicative a treatment can be paused and/or stopped (for example, when the expression level of the HIV splice variant plateaus).

In some embodiments, a method of the present invention for treating an HIV infection comprises comparing a measured expression level of the HIV splice variant of SEQ. ID. No. 1 in a patient to a previously measured expression level of the HIV splice variant of SEQ. ID. No. 1 in the patient.

In some embodiments, a method of the present invention for treating an HIV infection comprises measuring and/or monitoring a presence and/or expression level of an HIV splice variant of SEQ. ID. No. 1 in a patient to guide dose or monitor response to a treatment.

In some embodiments, a method of the present invention for treating an HIV infection comprises measuring and/or monitoring an HIV splice variant of SEQ. ID. No. 1 in a patient to guide therapy.

In some embodiments, a method of the present invention further comprises measuring pre-mRNA splicing of cellular genes in a patient or biological sample, wherein pre-mRNA splicing of cellular genes is not altered compared to a control sample. A control sample can be taken from various sources. In some embodiments, a control sample is taken from a patient prior to treatment or prior to the presence of a disease (such as an archival blood sample or tissue sample). In some embodiments, a control sample is taken from a set of normal, non-diseased members of a population. In some embodiments, a control sample is taken from a patient prior to treatment with a compound or a pharmaceutically acceptable salt or composition thereof as described herein. In some embodiments, a cell assay can be performed on a biological sample.

Inflammatory Diseases, Disorders, and Conditions, and Cancer

In some embodiments, the present invention provides a method of using miR-124 locus as a biomarker of an inflammatory disease, disorder, or condition, or a cancer, or of an efficacy of a therapeutic treatment of said inflammatory disease, disorder, or condition, or said cancer, which comprises measuring a presence or an expression level of miR-124 in a biological sample.

In some embodiments, the present invention provides a method of assessing biological effect of a compound or a medical device on treating an inflammatory disease, disorder, or condition, or a cancer, which comprises measuring a presence or an expression level of miR-124 as a biomarker of said inflammatory disease, disorder, or condition, or said cancer.

In some embodiments, the present invention provides a method of screening a compound or a medical device in treating an inflammatory disease, disorder, or condition, or a cancer, which comprises measuring a presence or an expression level of miR-124 as a biomarker of said inflammatory disease, disorder, or condition, or said cancer.

In some embodiments, the present invention provides a method of treating an inflammatory disease, disorder, or condition, or a cancer, which comprises measuring and/or monitoring a presence and/or an expression level of miR-124 as a biomarker of said inflammatory disease, disorder, or condition, or said cancer.

In some embodiments, the present invention provides a method of using a spliced long noncoding RNA at miR-124 locus as a biomarker of an inflammatory disease, disorder, or condition, or a cancer, or of an efficacy of a therapeutic treatment of said inflammatory disease, disorder, or condition, or said cancer, which comprises measuring a presence or an expression level of a spliced long noncoding RNA at miR-124 locus in a biological sample.

In some embodiments, the present invention provides a method of assessing biological effect of a compound or a medical device on treating an inflammatory disease, disorder, or condition, or a cancer, which comprises measuring a presence or an expression level of a spliced long noncoding RNA at miR-124 locus as a biomarker of said inflammatory disease, disorder, or condition, or said cancer.

In some embodiments, the present invention provides a method of screening a compound or a medical device in treating an inflammatory disease, disorder, or condition, or a cancer, which comprises measuring a presence or an expression level of a spliced long noncoding RNA at miR-124 locus as a biomarker of said inflammatory disease, disorder, or condition, or said cancer.

In some embodiments, the present invention provides a method of treating an inflammatory disease, disorder, or condition, or a cancer, which comprises measuring and/or monitoring a presence and/or an expression level of a spliced long noncoding RNA at miR-124 locus as a biomarker of said inflammatory disease, disorder, or condition, or said cancer.

In some embodiments, a spliced long noncoding RNA at miR-124 locus is at the miR-124-1 locus. In some embodiments, a spliced long noncoding RNA at miR-124 locus is at the miR-124-2 locus. In some embodiments, a spliced long noncoding RNA at miR-124 locus is at the miR-124-3 locus.

In some embodiments, a presence or an expression level of a spliced long noncoding RNA at miR-124 locus is measured using RNA and/or DNA amplification, sequencing, isotopes, fluorescence, chromogenic enzymes, spectroscopy, spectrometry, immunoassay, or immuno-enzymatic assays.

As described herein, ABX464 is found to induce a long noncoding RNA (lncRNA 0599-205) at the miR-124-1 locus (FIGS. 4 A and C). The long noncoding RNA referred herein, and throughout the specification, as «lncRNA0599-205 » or «LINC00599-205 », is derived from the region of the miR-124-1 locus ranging from position 9903000 to position 9904500 of chromosome 8 including the said miR-124-1 locus (FIGS. 4 A and C); in particular from position 9903107 to position 9904210. As a reference, the region of the sequence including transcript lncRNA 0599-205 is further referenced herein as SEQ ID No 15. The sequence of the three exons corresponding to the lncRNA0599-205 transcript, from 5' to 3', is further referenced herein, respectively, as SEQ ID No 16, as SEQ ID No 17 and as SEQ ID No 18. The sequence of the lncRNA 0599-205 transcript is further registered in the ENSEMBL database as: ENST00000521863.1.

Accordingly, in some embodiments, a spliced long noncoding RNA at miR-124 locus is lncRNA 0599-205 at the miR-124-1 locus, as a biomarker of an inflammatory disease, disorder, or condition, or a cancer.

In some embodiments, the present invention provides a method of using lncRNA 0599-205 at the miR-124-1 locus, as a biomarker of an inflammatory disease, disorder, or condition, or a cancer, or of an efficacy of a therapeutic treatment of an inflammatory disease, disorder, or condition, or a cancer, which comprises measuring a presence or an expression level of lncRNA 0599-205 at the miR-124-1 locus in a biological sample.

In some embodiments, a presence of lncRNA 0599-205 at the miR-124-1 locus in an isolated biological is indicative of an efficacy of a therapeutic treatment of an inflammatory disease, disorder, or condition, or a cancer.

In some embodiments, a measured expression level of lncRNA 0599-205 at the miR-124-1 locus in an isolated biological sample is compared to a measured expression level of lncRNA 0599-205 at the miR-124-1 locus in a previously isolated biological sample, and wherein an increase in expression level of lncRNA 0599-205 at the miR-124-1 locus is indicative of an efficacy of a therapeutic treatment of an inflammatory disease, disorder, or condition, or a cancer.

In some embodiments, the present invention provides a method of assessing biological effect of a compound on treating an inflammatory disease, disorder, or condition, or a cancer, which comprises measuring a presence or an expression level of lncRNA 0599-205 at the miR-124-1 locus as a biomarker of an inflammatory disease, disorder, or condition, or a cancer.

In some embodiments, the present invention provides a method of screening a compound in treating an inflammatory disease, disorder, or condition, or a cancer, which comprises measuring a presence or an expression level of lncRNA 0599-205 at the miR-124-1 locus as a biomarker of an inflammatory disease, disorder, or condition, or a cancer.

In some embodiments, a method of the present invention for treating an inflammatory disease, disorder or condition, or a cancer, further comprises measuring and/or monitoring a presence and/or level of lncRNA 0599-205 at the miR-124-1 locus in a patient. In some embodiments, a presence and/or level of lncRNA 0599-205 at the miR-124-1 locus is measured in a patient's biological sample. In some embodiments, a patient's biological sample is a blood sample. In some embodiments, a patient's biological sample is a tissue sample. In some embodiments, a method of the present invention for treating an inflammatory disease, disorder or condition, or a cancer, further comprises measuring and/or monitoring a presence and/or expression level of lncRNA 0599-205 at the miR-124-1 locus in a patient prior to administering a compound or a pharmaceutically acceptable salt or composition thereof as described herein. In some embodiments, a method of the present invention for treating an inflammatory disease, disorder or condition, or a cancer, further comprises measuring and/or monitoring a presence and/or expression level of lncRNA 0599-205 at the miR-124-1 locus in a patient during the course of a treatment with a compound or a pharmaceutically acceptable salt or composition thereof as described herein. In some embodiments, a method of the present invention for treating an inflammatory disease, disorder or condition, or a cancer, further comprises selecting a patient for a treatment with a compound or a pharmaceutically acceptable salt or composition thereof as described herein, by measuring and/or monitoring a presence and/or expression level of lncRNA 0599-205 at the miR-124-1 locus in the patient. In some embodiments, a method of the present invention for treating an inflammatory disease, disorder or condition, or a cancer, further comprises excluding a patient from a treatment with a compound or a pharmaceutically acceptable salt or composition thereof as described herein, by measuring and/or monitoring a presence and/or expression level of lncRNA 0599-205 at the miR-124-1 locus in the patient. In some embodiments, a method of the present invention for treating an inflammatory disease, disorder or condition, or a cancer, further comprises adjusting (such as increasing or decreasing) dosage regimen (such as dose amount and/or dose schedule) of a compound or a pharmaceutically acceptable salt or composition thereof as described herein to be administered to a patient, by measuring and/or monitoring a presence and/or expression level of lncRNA 0599-205 at the miR-124-1 locus in the patient.

In some embodiments, a method of the present invention for treating an inflammatory disease, disorder or condition, or a cancer, comprises comparing a measured expression level of lncRNA 0599-205 at the miR-124-1 locus in a patient to a control reference value. A control reference value to be used for comparing a measured expression level of lncRNA 0599-205 at the miR-124-1 locus in a patient is obtained from a control sample. A control sample can be taken from various sources. In some embodiments, a control sample is taken from a patient prior to treatment or prior to the presence of a disease (such as an archival blood sample or tissue sample). In some embodiments, a control sample is taken from a set of normal, non-diseased members of a population. In some embodiments, a control sample is taken from a patient prior to treatment with a compound or a pharmaceutically acceptable salt or composition thereof as described herein. In some embodiments, a cell assay can be performed on a biological sample.

In some embodiments, a modulated presence and/or expression level of lncRNA 0599-205 at the miR-124-1 locus in a patient compared to a control reference value indicates an inflammatory disease, disorder or condition, or a cancer. In some embodiments, a modulated presence and/or expression level of lncRNA 0599-205 at the miR-124-1 locus in a patient compared to a control reference value indicates an efficacy of a treatment with a compound or a pharmaceutically acceptable salt or composition thereof as described herein, which is administered to the patient. The terms “modulation” or “modulated presence and/or expression level” means the presence or expression level of a biomarker, for example, lncRNA 0599-205 at the miR-124-1 locus, is either induced or increased, or alternatively is suppressed or decreased.

In some embodiments, a measured reduced or suppressed presence, or a decreased expression level, of lncRNA 0599-205 at the miR-124-1 locus relative to a control reference value indicates an inflammatory disease, disorder or condition, or a cancer. In some embodiments, a measured induced or increased presence, or an increased expression level, of lncRNA 0599-205 at the miR-124-1 locus relative to a control reference value indicates an efficacy of a compound or a pharmaceutically acceptable salt or composition thereof as described herein. In some embodiments, a measured expression level of lncRNA 0599-205 at the miR-124-1 locus in a patient treated with a compound or a pharmaceutically acceptable salt or composition thereof as described herein is a two-fold, four-fold, six-fold, eight-fold, or ten-fold increase relative to a control reference value.

In some embodiments, a method of the present invention for treating an inflammatory disease, disorder or condition, or a cancer, comprises measuring and/or monitoring a presence and/or expression level of lncRNA 0599-205 at the miR-124-1 locus in a patient to guide dose or monitor response to a treatment.

In some embodiments, a method of the present invention for treating an inflammatory disease, disorder or condition, or a cancer, comprises measuring and/or monitoring lncRNA 0599-205 at the miR-124-1 locus in a patient to guide therapy.

In some embodiments, the present invention provides an algorithm that combines the level of lncRNA 0599-205 at the miR-124-1 locus and the level of a cytokine or another biomarker to monitor severity of an inflammatory disease, disorder, or condition, or a cancer, and/or to monitor efficacy of a treatment, including but not limited to a treatment as described herein. In some embodiments, a treatment method as described herein comprises using an algorithm that combines the level of lncRNA 0599-205 at the miR-124-1 locus and the level of a cytokine or another biomarker to monitor severity of an inflammatory disease, disorder, or condition, or a cancer, and/or to monitor efficacy of the treatment.

2. Definitions

The compounds of the invention may exist in the form of free bases or of addition salts with pharmaceutically acceptable acids. Suitable physiologically acceptable acid addition salts of compounds of the present invention include sulfate, hydrobromide, citrate, trifluoroacetate, ascorbate, hydrochloride, tartrate, triflate, maleate, mesylate, formate, acetate, fumarate and sulfonate, in particular alkylsufonate or arylsulfonate, and more particularly mesylate, triflate, edisylate, besylate and tosylate.

The compounds of the present invention and or salts thereof may form solvates or hydrates and the invention includes all such solvates and hydrates. The terms “hydrates” and “solvates” simply mean that the compounds according to the invention can be in the form of a hydrate or solvate, i.e. combined or associated with one or more water or solvent molecules. This is only a chemical characteristic of such compounds, which can be applied for all organic compounds of this type.

The compounds of the present invention can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

In the context of the present invention, the term:

“halogen” is understood to mean chlorine, fluorine, bromine, or iodine, and in particular denotes chlorine, fluorine or bromine, “$(C_1-C_5)$alkyl” as used herein respectively refers to $C_1-C_5$ normal, secondary or tertiary saturated hydrocarbon. Examples are, but are not limited to, methyl, ethyl, 1-propyl, 2-propyl, butyl, pentyl, “$(C_3-C_6)$cycloalkyl” as used herein respectively refers to cyclic saturated hydrocarbon. Examples are, but are not limited to cyclopropyl, cyclobutyl, cyclopentyl, cyclohexyl, “$(C_1-C_4)$alkoxy” as used herein respectively refers to O—$(C_1-C_4)$alkyl moiety, wherein alkyl is as defined above. Examples are, but are not limited to, methoxy, ethoxy, 1-propoxy, 2-propoxy, butoxy, “fluoroalkyl group” and “fluoroalkoxy group” refers respectively to alkyl group and alkoxy group as above-defined, said groups being substituted by at least one fluorine atom. Examples are perfluoroalkyl groups, such as trifluoromethyl or perfluoropropyl, “saturated 5- or 6-membered heterocycle” as used herein respectively refers to a saturated cycle comprising at least one heteroatom. Examples are, but are not limited to, morpholine, piperazine, thiomorpholine, piperidine, pyrrolidine.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases.

Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

3. Exemplary Embodiments of Treatment Methods

In one aspect, the present invention provides a method for treating a viral infection, or an inflammatory disease, disorder or condition, or a cancer, comprising administering to a patient in need thereof a compound of Formula (I):

(I)

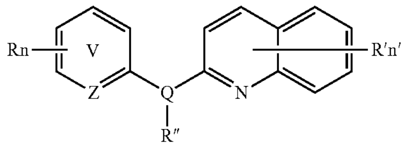

or a pharmaceutically acceptable salt thereof, wherein:

Z is C or N;

V is C or N;

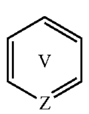

means an aromatic ring wherein V is C or N and when V is N, V is ortho, meta or para relative to Z;

each R is independently hydrogen, halogen, —CN, hydroxyl, $(C_1-C_3)$fluoroalkyl, $(C_1-C_3)$fluoroalkoxy, $(C_3-C_6)$cycloalkyl, $—NO_2$, $—NR_1R_2$, $(C_1-C_4)$alkoxy, phenoxy, $—NR_1—SO_2—NR_1R_2$, $—NR_1—SO_2—R_1$, $—NR_1—C(═O)—R_1$, $—NR_1—C(═O)—NR_1R_2$, $—SO_2—NR_1R_2$, $—SO_3H$, $—O—SO_2—OR_3$, $—O—P(═O)—(OR_3)(OR_4)$, $—O—CH_2—COOR_3$, $(C_1-C_3)$alkyl, said alkyl being optionally mono- or di-substituted by a hydroxyl group or a group of formula (IIa):

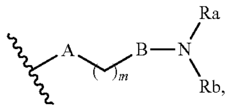

or a group of formula (IIIa):

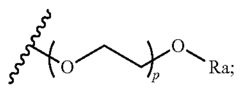

Q is N or O, provided that R" does not exist when Q is O;

each of $R_1$ and $R_2$ is independently hydrogen or $(C_1-C_3)$alkyl;

each of $R_3$ and $R_4$ is independently hydrogen, $Li^+$, $Na^+$, $K^+$, $N^+(Ra)_4$, or benzyl;

n is 1, 2 or 3;

n' is 1, 2 or 3;

each R' is independently hydrogen, $(C_1-C_3)$alkyl, hydroxyl, halogen, $—NO_2$, $—NR_1R_2$, morpholinyl, morpholino, N-methylpiperazinyl, $(C_1-C_3)$fluoroalkyl, $(C_1-C_4)$alkoxy, $—O—P(═O)—(OR_3)(OR_4)$, —CN, a group of formula (IIa):

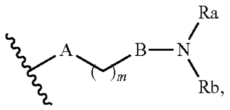

or a group of formula (IIIa):

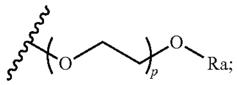

A is a covalent bond, oxygen, or NH;
B is a covalent bond or NH;
m is 1, 2, 3, 4 or 5;
p is 1, 2 or 3;
each of Ra and Rb is independently hydrogen, $(C_1\text{-}C_5)$alkyl, or $(C_3\text{-}C_6)$cycloalkyl, or
Ra and Rb form together with the nitrogen atom to which they are attached a saturated 5- or 6-membered heterocycle, said heterocycle being optionally substituted by one or more Ra, provided that when R' is a group (IIa) or (IIIa), n' may be 2 or 3 only if other R' groups are different from said group (IIa) or (IIIa); and
R" is hydrogen, $(C_1\text{-}C_4)$alkyl, or a group of formula (IIa) as defined above.

As defined generally above, Z is C or N.

In some embodiments, Z is C. In some embodiments, Z is N.

In some embodiments, Z is selected from those depicted in Tables 1-3, below.

As defined generally above, V is C or N.

In some embodiments, V is C. In some embodiments, V is N.

In some embodiments, V is selected from those depicted in Tables 1-3, below.

As defined generally above,

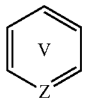

means an aromatic ring wherein V is C or N and when V is N, V is ortho, meta or para relative to Z.

In some embodiments,

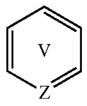

means an aromatic ring wherein V is C.

In some embodiments,

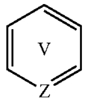

means an aromatic ring wherein V is N. and V is ortho, meta or para relative to Z. In some embodiments, V is N, and V is ortho relative to Z. In some embodiments, V is N, and V is meta relative to Z. In some embodiments, V is N, and V is para relative to Z.

In some embodiments,

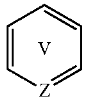

is phenyl. In some embodiments,

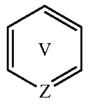

is pyridine. In some embodiments,

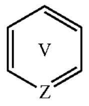

is pyridazine. In some embodiments,

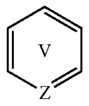

is pyrimidine. In some embodiments,

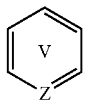

is pyrazine.

In some embodiments,

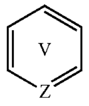

is selected from those depicted in Tables 1-3, below.

As described generally above, each R is independently hydrogen, halogen, —CN, hydroxyl, $(C_1\text{-}C_3)$fluoroalkyl, $(C_1\text{-}C_3)$fluoroalkoxy, $(C_3\text{-}C_6)$cycloalkyl, $—NO_2$, $—NR_1R_2$, $(C_1\text{-}C_4)$alkoxy, phenoxy, $—NR_1—SO_2—NR_1R_2$, $—NR_1—SO_2—R_1$, $—NR_1—C({=}O)—R_1$, $—NR_1—C({=}O)—NR_1R_2$, $—SO_2—NR_1R_2$, $—SO_3H$, $—O—SO_2—OR_3$, $—O—P({=}O)—(OR_3)(OR_4)$, $—O—CH_2—COOR_3$, or $(C_1\text{-}C_3)$alkyl, said alkyl being optionally mono- or di-substituted by a hydroxyl group.

In some embodiments, R is hydrogen. In some embodiments, R is halogen. In some embodiments, R is —CN. In some embodiments, R is hydroxyl. In some embodiments, R is $(C_1-C_3)$fluoroalkyl, said alkyl being optionally mono- or di-substituted by hydroxyl. In some embodiments, R is $(C_1-C_3)$fluoroalkoxy. In some embodiments, R is $(C_3-C_6)$ cycloalkyl. In some embodiments, R is —$NO_2$. In some embodiments, R is —$NR_1R_2$. In some embodiments, R is $(C_1-C_4)$alkoxy. In some embodiments. R is phenoxy. In some embodiments, R is —$NR_1$—$SO_2$—$NR_1R_2$. In some embodiments, R is —$NR_1$—$SO_2$—$R_1$. In some embodiments, R is —$NR_1$—C(=O)—$R_1$. In some embodiments. R is —$NR_1$—C(=O)—$NR_1R_2$. In some embodiments, R is —$SO_2$—$NR_1R_2$. In some embodiments, R is —$SO_3H$. In some embodiments, R is —O—$SO_2$—$OR_3$. In some embodiments, R is —O—P(=O)—$(OR_3)(OR_4)$. In some embodiments, R is —O—$CH_2$—$COOR_3$. In some embodiments, R is $(C_1-C_3)$alkyl, said alkyl being optionally mono- or di-substituted by hydroxyl.

In some embodiments, each R is independently halogen, $(C_1-C_3)$fluoroalkyl, $(C_1-C_3)$fluoroalkoxy, —$NR_1R_2$, $(C_1-C_4)$ alkoxy, or $(C_1-C_3)$alkyl.

In some embodiments, each R is independently hydrogen, methyl, methoxy, trifluoromethyl, trifluoromethoxy, amino, halogen, or —O—P(=O)—$(OR_3)(OR_4)$. In some embodiments, R is methyl. In some embodiments, R is methoxy. In some embodiments, R is trifluoromethyl. In some embodiments, R is trifluoromethoxy. In some embodiments, R is amino. In some embodiments, R is —O—P(=O)—$(OR_3)$ $(OR_4)$.

In some embodiments, each R is independently methyl, methoxy, trifluoromethyl, halogen, trifluoromethoxy, or amino.

In some embodiments, R is selected from those depicted in Tables 1-3, below.

As described generally above, Q is N or O, provided that R" does not exist when Q is O.

In some embodiments, Q is N. In some embodiments, Q is O, and R" does not exist.

In some embodiments, Q is selected from those depicted in Tables 1-3, below.

As described generally above, each of $R_1$ and $R_2$ is independently hydrogen or $(C_1-C_3)$alkyl.

In some embodiments, $R_1$ is hydrogen. In some embodiments, $R_1$ is $(C_1-C_3)$alkyl. In some embodiments, $R_2$ is hydrogen. In some embodiments. $R_2$ is $(C_1-C_3)$alkyl.

In some embodiments, each of $R_1$ and $R_2$ is independently selected from those depicted in Tables 1-3, below.

As described generally above, each of $R_3$ and $R_4$ is independently hydrogen. $Li^+$, $Na^+$, $K^+$, $N^+(Ra)_4$ or benzyl.

In some embodiments, $R_3$ is hydrogen. In some embodiments. $R_3$ is $Li^+$. In some embodiments, $R_3$ is $Na^+$. In some embodiments, $R_3$ is $K^+$. In some embodiments, $R_3$ is $N^+(Ra)_4$. In some embodiments, $R_3$ is benzyl. In some embodiments, $R_4$ is hydrogen. In some embodiments, $R_4$ is $Li^+$. In some embodiments, $R_4$ is $Na^+$. In some embodiments, $R_4$ is $K^+$. In some embodiments, $R_4$ is $N^+(Ra)_4$. In some embodiments, $R_4$ is benzyl.

In some embodiments, each of $R_3$ and $R_4$ is independently selected from those depicted in Tables 1-3, below.

As described generally above, n is 1, 2 or 3.

In some embodiments, n is 1 or 2. In some embodiments, n is 1. In some embodiments, n is 2. In some embodiments, n is 3.

In some embodiments, n is selected from those depicted in Tables 1-3, below.

As described generally above, n' is 1, 2 or 3.

In some embodiments, n' is 1 or 2. In some embodiments, n' is 1. In some embodiments, n' is 2. In some embodiments, n' is 3.

In some embodiments, n' is selected from those depicted in Tables 1-3, below.

As described generally above, each R' is independently hydrogen, $(C_1-C_3)$alkyl, hydroxyl, halogen, —$NO_2$, —$NR_1R_2$, morpholinyl, morpholino, N-methylpiperazinyl, $(C_1-C_3)$fluoroalkyl, $(C_1-C_4)$alkoxy, —O—P(=O)—$(OR_3)$ $(OR_4)$, —CN, a group of formula (IIa):

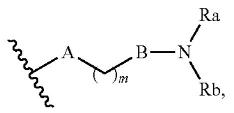

or a group of formula (IIIa):

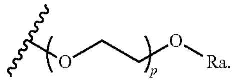

In some embodiments, R' is hydrogen. In some embodiments, R' is $(C_1-C_3)$alkyl. In some embodiments, R' is Hydroxyl. In some embodiments, R' is halogen. In some embodiments, R' is —$NO_2$. In some embodiments, R' is —$NR_1R_2$. In some embodiments, R' is morpholinyl. In some embodiments, R' is morpholino. In some embodiments, R' is N-methylpiperazinyl. In some embodiments, R' is $(C_1-C_3)$ fluoroalkyl. In some embodiments, R' is $(C_1-C_4)$alkoxy. In some embodiments, R' is —O—P(=O)—$(OR_3)(OR_4)$. In some embodiments, R' is —CN. In some embodiments, R' is a group of formula (IIa):

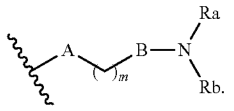

In some embodiments, R' is a group of formula (IIIa):

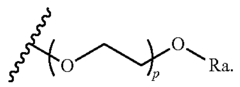

In some embodiments, R' is amino. In some embodiments, R' is methyl. In some embodiments, R' is a group of formula

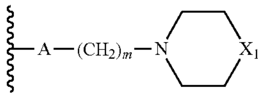

wherein A is O or NH, m is 2 or 3 and $X_1$ is O. $CH_2$ or N—$CH_3$, provided that when R' is such a group, n' is 1 or 2, and when n' is 2, the other R' group is different from said group.

In some embodiments, R' is a group of formula

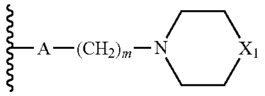

wherein A is O or NH, m is 2 and $X_1$ is O, $CH_2$ or N—$CH_3$, provided that when R' is such a group, n' is 1 or 2, and when n' is 2, the other R' group is different from said group.

In some embodiments, R' is a group of formula

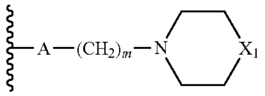

wherein A is O or NH, m is 3 and $X_1$ is O, $CH_2$ or N—$CH_3$, provided that when R' is such a group, n' is 1 or 2, and when n' is 2, the other R' group is different from said group.

In some embodiments, each R' is independently hydrogen, halogen, amino, methyl, —O—P(═O)—($OR_3$)($OR_4$), or a group of formula

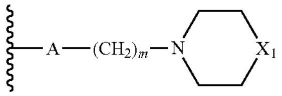

wherein A is O or NH, m is 2 or 3 and $X_1$ is O. $CH_2$ or N—$CH_3$, provided that when R' is such a group, n' is 1 or 2, and when n' is 2, the other R' group is different from said group.

In some embodiments, each R' is independently hydrogen, halogen, methyl, or a group of formula

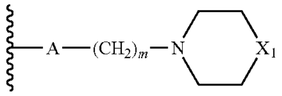

wherein A is O or NH, m is 2 and X, is O. $CH_2$ or N—$CH_3$, provided that when R' is such a group, n' is 1 or 2, and when n' is 2, the other R' group is different from said group.

In some embodiments, each R' is independently halogen, ($C_1$-$C_3$)alkyl, hydroxyl, —$NR_1R_2$, morpholinyl, morpholino, N-methylpiperazinyl, ($C_1$-$C_3$)fluoroalkyl, ($C_1$-$C_4$) alkoxy, or a group of formulas IIa or IIIa as described herein.

In some embodiments, R' is halogen or methyl.

In some embodiments, each R' is independently selected from those depicted in Tables 1-3, below.

As described generally above, A is a covalent bond, oxygen, or NH.

In some embodiments, A is a covalent bond. In some embodiments. A is oxygen. In some embodiments, A is NH.

In some embodiments, A is selected from those depicted in Tables 1-3, below.

As described generally above, B is a covalent bond or NH.

In some embodiments, B is a covalent bond. In some embodiments, B is NH.

In some embodiments, B is selected from those depicted in Tables 1-3, below.

As described generally above, m is 1, 2, 3, 4 or 5.

In some embodiments, m is 1. In some embodiments, m is 2. In some embodiments, m is 3. In some embodiments, m is 4. In some embodiments, m is 5.

In some embodiments, m is selected from those depicted in Tables 1-3, below.

As described generally above, p is 1, 2 or 3.

In some embodiments, p is 1. In some embodiments, p is 2. In some embodiments, p is 3. In some embodiments, p is 4. In some embodiments, p is 5.

In some embodiments, p is selected from those depicted in Tables 1-3, below.

As described generally above, each of Ra and Rb is independently hydrogen, ($C_1$-$C_5$)alkyl, or ($C_3$-$C_6$)cycloalkyl, or Ra and Rb form together with the nitrogen atom to which they are attached a saturated 5- or 6-membered heterocycle, said heterocycle being optionally substituted by one or more Ra, provided that when R' is a group (IIa) or (IIIa), n' may be 2 or 3 only if other R' groups are different from said group (IIa) or (IIIa).

In some embodiments, Ra is hydrogen. In some embodiments, Ra is ($C_1$-$C_5$)alkyl. In some embodiments, Ra is ($C_3$-$C_6$)cycloalkyl. In some embodiments, Rb is hydrogen. In some embodiments, Rb is ($C_1$-$C_5$)alkyl. In some embodiments, Rb is ($C_3$-$C_6$)cycloalkyl.

In some embodiments, Ra and Rb form together with the nitrogen atom to which they are attached a saturated 5- or 6-membered heterocycle, said heterocycle being optionally substituted by one or more Ra, provided that when R' is a group of formulas (IIa) or (IIIa), n' may be 2 or 3 only if other R' groups are different from said group of formulas (IIa) or (IIIa). In some embodiments, a saturated 5- or 6-membered heterocycle formed by Ra and Rb together with the nitrogen atom to which they are attached, as described above, optionally has an additional heteroatom selected from N, O and S.

In some embodiments, Ra and Rb form together with the nitrogen atom to which they are attached a saturated 5- or 6-membered heterocycle having an additional heteroatom selected from N, O and S, said heterocycle being substituted by one or more Ra, provided that when R' is a group of formulas (IIa) or (IIIa), n' may be 2 or 3 only if other R' groups are different from said group of formulas (IIa) or (IIIa).

In some embodiments, Ra and Rb form together with the nitrogen atom to which they are attached a saturated 5-membered heterocycle, provided that when R' is a group of formulas (IIa) or (IIIa), n' may be 2 or 3 only if other R' groups are different from said group of formulas (IIa) or (IIIa).

In some embodiments, Ra and Rb form together with the nitrogen atom to which they are attached a saturated 6-membered heterocycle, provided that when R' is a group of formulas (IIa) or (IIIa), n' may be 2 or 3 only if other R' groups are different from said group of formulas (IIa) or (IIIa).

In some embodiments, Ra and Rb form together with the nitrogen atom to which they are attached a saturated 5- or 6-membered heterocycle optionally having an additional heteroatom selected from N, O and S, said heterocycle being optionally substituted by one or more Ra, provided that when R' is a group (IIa) or (IIIa), n' may be 2 only if the other R' group is different from said group (IIa) or (IIIa).

In some embodiments, each of Ra and Rb is independently selected from those depicted in Tables 1-3, below.

As described generally above, R" is hydrogen, ($C_1$-$C_4$)alkyl, or a group of formula (IIa) as defined above.

In some embodiments, R" is hydrogen or ($C_1$-$C_4$)alkyl. In some embodiments, R" is hydrogen. In some embodiments, R" is ($C_1$-$C_4$)alkyl. In some embodiments, R" is a group of formula (IIa) as described herein.

In some embodiments, R" is a group of formula

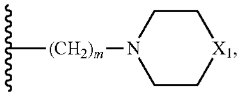

wherein m is 2 or 3, and $X_1$ is O, $CH_2$, or N—$CH_3$.

In some embodiments, R" is selected from those depicted in Tables 1-3, below.

In some embodiments, n is 1; n' is 1 or 2; R" is H; R is selected from methyl, methoxy, trifluoromethyl, halogen, trifluoromethoxy, and amino; and each R' is independently halogen, methyl, or a group

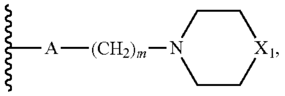

wherein A is O or NH, m is 2 or 3 and $X_1$ is O, $CH_2$ or N—$CH_3$, provided that when n' is 2, the other R' group is different from said group.

In some embodiments, n is 1; n' is 1; R" is H; R is selected from methyl, methoxy, trifluoromethyl, halogen, and trifluoromethoxy; and R' is halogen or methyl.

In some embodiments, the present invention provides a method for treating a viral infection, or an inflammatory disease, disorder or condition, or a cancer, comprising administering to a patient in need thereof a compound of formula (Ia):

(Ia)

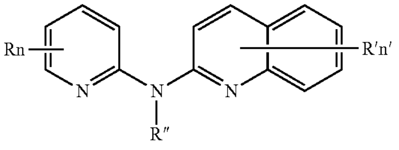

or a pharmaceutically acceptable salt thereof, wherein each of variables R, R', R", n, and n' is independently as defined above and described in embodiments herein, both singly and in combination.

In some embodiments, the present invention provides a method for treating a viral infection, or an inflammatory disease, disorder or condition, or a cancer, comprising administering to a patient in need thereof a compound of formula (Ib):

(Ib)

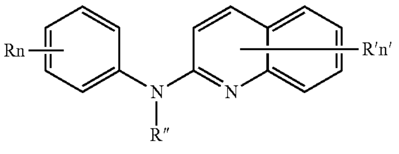

or a pharmaceutically acceptable salt thereof, wherein each of variables R, R', R", n, and n' is independently as defined above and described in embodiments herein, both singly and in combination.

In some embodiments, the present invention provides a method for treating a viral infection, or an inflammatory disease, disorder or condition, or a cancer, comprising administering to a patient in need thereof a compound of formula (Ic):

(Ic)

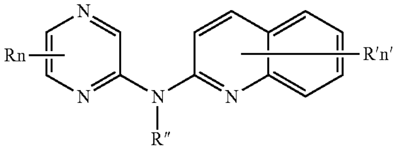

or a pharmaceutically acceptable salt thereof, wherein each of variables R, R', R", n, and n' is independently as defined above and described in embodiments herein, both singly and in combination.

In some embodiments, the present invention provides a method for treating a viral infection, or an inflammatory disease, disorder or condition, or a cancer, comprising administering to a patient in need thereof a compound of formula (Ib'):

(Ib')

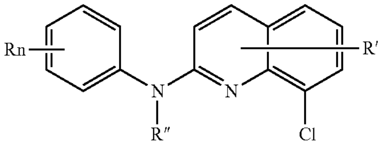

or a pharmaceutically acceptable salt thereof, wherein each of variables R, R', R", and n is independently as defined above and described in embodiments herein, both singly and in combination.

In some embodiments, the present invention provides a method for treating a viral infection, or an inflammatory disease, disorder or condition, or a cancer, comprising administering to a patient in need thereof a compound of formula (Ib), or a pharmaceutically acceptable salt thereof, wherein:

each R is independently halogen, ($C_1$-$C_3$)fluoroalkyl, ($C_1$-$C_3$)fluoroalkoxy, —$NR_1R_2$, ($C_1$-$C_4$)alkoxy, or ($C_1$-$C_3$)alkyl, said alkyl being optionally mono- or di-substituted by a hydroxyl group;

n is 1 or 2;

n' is 1 or 2;

each of $R_1$ and $R_2$ is independently hydrogen or ($C_1$-$C_3$)alkyl;

each of R' is independently halogen, ($C_1$-$C_3$)alkyl, hydroxyl, —$NR_1R_2$, morpholinyl, morpholino, N-methylpiperazinyl, ($C_1$-$C_3$)fluoroalkyl, ($C_1$-$C_4$)alkoxy, or a group of formulas (IIa) or (IIIa) as described herein;

A is a covalent bond, oxygen, or NH;

B is a covalent bond or NH;

m is 1, 2, 3, 4 or 5;

p is 1, 2 or 3;

each of Ra and Rb is independently hydrogen, ($C_1$-$C_5$)alkyl, or ($C_3$-$C_6$)cycloalkyl, or Ra and Rb form together with the nitrogen atom to which they are attached a saturated 5- or 6-membered heterocycle optionally having an additional heteroatom selected from N, O and S, said heterocycle being optionally substituted by one or more Ra, provided that when R' is a group (IIa) or (IIIa), n' may be 2 only if the other R' group is different from said group (IIa) or (IIIa); and R" is hydrogen or $(C_1-C_4)$alkyl.

In some embodiments, the present invention provides a method for treating a viral infection, or an inflammatory disease, disorder or condition, or a cancer, comprising administering to a patient in need thereof a compound of formula (Ib), or a pharmaceutically acceptable salt thereof, wherein each R' is independently hydrogen, halogen, $(C_1-C_3)$alkyl, or a $(C_1-C_4)$alkoxy group, said alkyl being optionally mono- or di-substituted by a hydroxyl group; R" is hydrogen or $(C_1-C_4)$alkyl; n is 1 or 2; n' is 1 or 2; when n is 1, R is $(C_1-C_3)$ fluoroalkoxy, $NR_1R_2$, or phenoxy, wherein each of $R_1$ and $R_2$ is independently $(C_1-C_3)$alkyl; and when n is 2, one of the two R groups is $(C_1-C_3)$ fluoroalkoxy and the other R group is $(C_1-C_3)$alkyl.

In some embodiments, the present invention provides a method for treating a viral infection, or an inflammatory disease, disorder or condition, or a cancer, comprising administering to a patient in need thereof a compound of formula (Ib), or a pharmaceutically acceptable salt thereof, wherein each R is independently $(C_1-C_3)$fluoroalkoxy; each R' is independently hydrogen, halogen, $(C_1-C_3)$alkyl, or $(C_1-C_4)$alkoxy; R" is hydrogen or $(C_1-C_4)$alkyl; n is 1; and n' is 1 or 2.

In some embodiments, the present invention provides a method for treating a viral infection, or an inflammatory disease, disorder or condition, or a cancer, comprising administering to a patient in need thereof a compound of formula (Ib'), or a pharmaceutically acceptable salt thereof, wherein each R is independently hydrogen, halogen, $(C_1-C_3)$alkyl, $—NR_1R_2$, $(C_1-C_3)$fluoroalkoxy, $—NO_2$, phenoxy, or $(C_1-C_4)$alkoxy, said alkyl being optionally mono- or di-substituted by a hydroxyl group; each of $R_1$ and $R_2$ is independently hydrogen or $(C_1-C_3)$alkyl; R' is hydrogen, halogen, $(C_1-C_3)$alkyl, or $(C_1-C_4)$alkoxy, with the proviso that R' is different from a methyl group at position 4 of the quinoline group; R" is hydrogen or $(C_1-C_4)$alkyl; n is 1, 2, or 3; and n' is 1 or 2.

In some embodiments, the present invention provides a method for treating a viral infection, or an inflammatory disease, disorder or condition, or a cancer, comprising administering to a patient in need thereof a compound of formula (Id):

(Id)

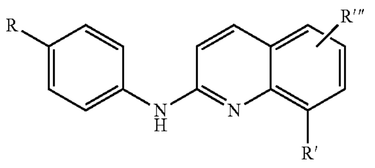

or a pharmaceutically acceptable salt thereof, wherein each of R and R' is independently as defined above and described in embodiments herein, both singly and in combination, and R''' is hydrogen or a group

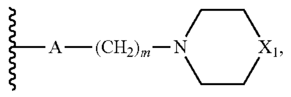

wherein A is O or NH, m is 2 or 3, and $X_1$ is O, $CH_2$ or $N—CH_3$.

In some embodiments, the present invention provides a method for treating a viral infection, or an inflammatory disease, disorder or condition, or a cancer, comprising administering to a patient in need thereof a compound of formula (Id), or a pharmaceutically acceptable salt thereof, wherein R is methyl, methoxy, trifluoromethyl, halogen, trifluoromethoxy, or amino; R' is halogen or methyl, and R''' is hydrogen or a group

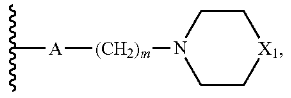

wherein A is O or NH, m is 2 or 3, and $X_1$ is O, $CH_2$ or $N—CH_3$.

In some embodiments, R''' is hydrogen. In some embodiments, R''' is a group

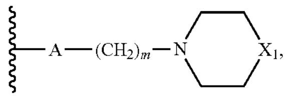

wherein A is O or NH, m is 2 or 3, and $X_1$ is O, $CH_2$ or $N—CH_3$. In some embodiments, R''' is a group

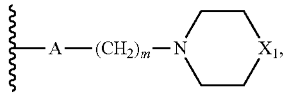

wherein A is O, m is 2 or 3, and $X_1$ is O, $CH_2$ or $N—CH_3$. In some embodiments, R''' is a group

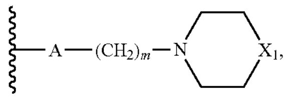

wherein A is NH, m is 2 or 3, and $X_1$ is O, $CH_2$ or $N—CH_3$.

In some embodiments, the present invention provides a method for treating a viral infection, or an inflammatory disease, disorder or condition, or a cancer, comprising administering to a patient in need thereof a compound of formula:

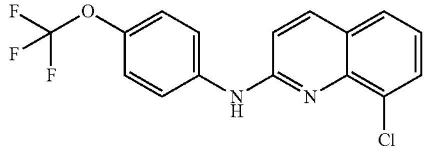 [SMILES: FC(F)(F)Oc1ccc(Nc2ccc3cccc(Cl)c3n2)cc1]

8-chloro-N-(4-(trifluoromethoxy)phenyl)quinolin-2-amine ("ABX464"), or a pharmaceutically acceptable salt thereof.

In some embodiments, the compound ABX464, or a pharmaceutically acceptable salt thereof, is under an amorphous form. In some embodiments, the compound ABX464, or a pharmaceutically acceptable salt thereof, is under a crystallized form. In some embodiments, a crystallized form of the compound ABX464, or a pharmaceutically acceptable salt thereof, has a melting point at 120.5° C. (±2° C.). In some embodiments, a crystallized form of the compound ABX464, or a pharmaceutically acceptable salt thereof, shows peaks in an x-ray powder diffractogram (XRPD) at angles 7.3, 14.6, 18.4, and 24.9. In some embodiments, a crystallized form of the compound ABX464, or a pharmaceutically acceptable salt thereof, shows one or more XRPD peaks at angles selected from 18.0, 24.2, 28.3, and 29.5. In some embodiments, a crystallized form of the compound ABX464, or a pharmaceutically acceptable salt thereof, shows one or more XRPD peaks at angles selected from 18.6, 22.3, 23.0, and 23.5.

In some embodiments, the present invention provides a method for treating a viral infection, or an inflammatory disease, disorder or condition, or a cancer, comprising administering to a patient in need thereof a compound selected from Table 1:

TABLE 1

(compounds of formula Ia as defined above)

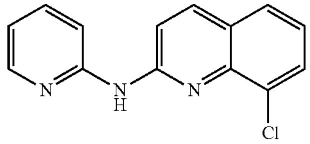 [SMILES: Clc1cccc2ccc(Nc3ccccn3)nc12]
1

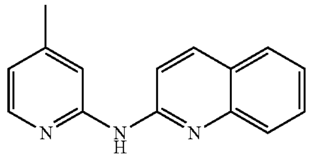 [SMILES: Cc1ccnc(Nc2ccc3ccccc3n2)c1]
2

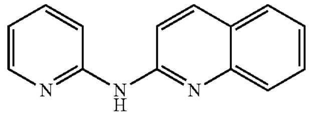 [SMILES: c1ccc(Nc2ccc3ccccc3n2)nc1]
3

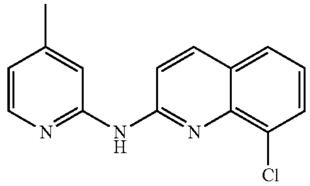 [SMILES: Cc1ccnc(Nc2ccc3cccc(Cl)c3n2)c1]
4

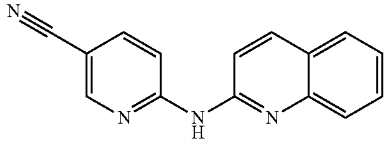 [SMILES: N#Cc1ccc(Nc2ccc3ccccc3n2)nc1]
5

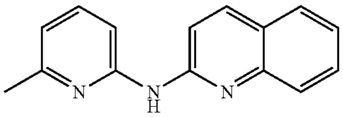 [SMILES: Cc1cccc(Nc2ccc3ccccc3n2)n1]
6

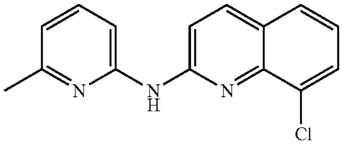 [SMILES: Cc1cccc(Nc2ccc3cccc(Cl)c3n2)n1]
7

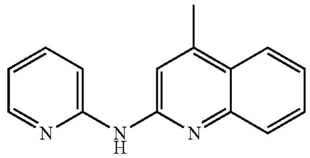 [SMILES: Cc1cc(Nc2ccccn2)nc2ccccc12]
8

TABLE 1-continued
(compounds of formula Ia as defined above)
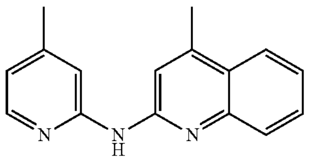
9
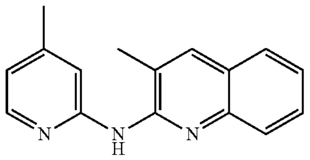 [SMILES: Cc1ccnc(Nc2nc3ccccc3cc2C)c1]
10
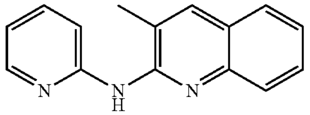 [SMILES: Cc1cc2ccccc2nc1Nc1ccccn1]
11
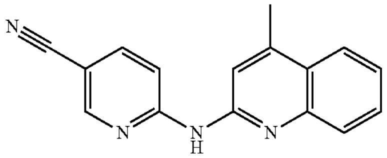 [SMILES: Cc1cc(Nc2ccc(C#N)cn2)nc2ccccc12]
12
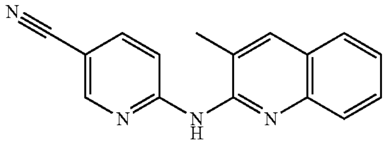 [SMILES: Cc1cc2ccccc2nc1Nc1ccc(C#N)cn1]
13
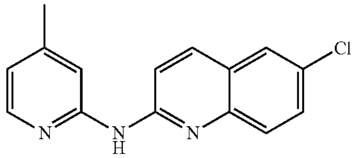 [SMILES: Cc1ccnc(Nc2ccc3cc(Cl)ccc3n2)c1]
14
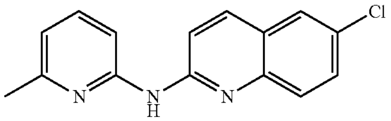 [SMILES: Cc1cccc(Nc2ccc3cc(Cl)ccc3n2)n1]
15
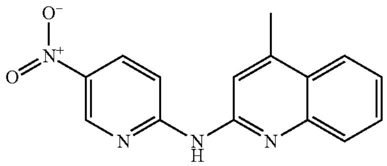 [SMILES: Cc1cc(Nc2ccc([N+](=O)[O-])cn2)nc2ccccc12]
16
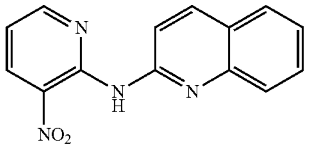 [SMILES: O=[N+]([O-])c1cccnc1Nc1ccc2ccccc2n1]
17

TABLE 1-continued
(compounds of formula Ia as defined above)
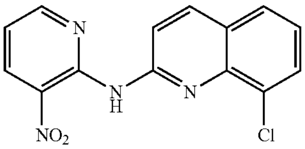 [SMILES: O=[N+]([O-])c1cccnc1Nc1ccc2cccc(Cl)c2n1]
18
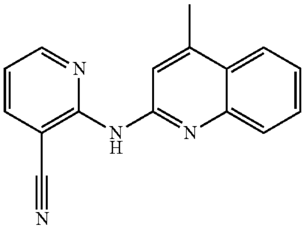 [SMILES: Cc1cc(Nc2ncccc2C#N)nc2ccccc12]
19
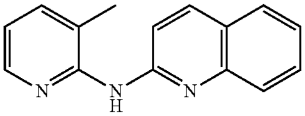 [SMILES: Cc1cccnc1Nc1ccc2ccccc2n1]
20
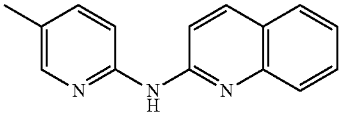 [SMILES: Cc1ccc(Nc2ccc3ccccc3n2)nc1]
21
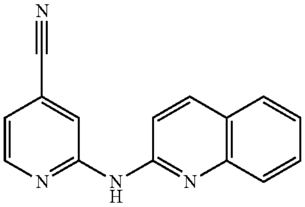 [SMILES: N#Cc1ccnc(Nc2ccc3ccccc3n2)c1]
22
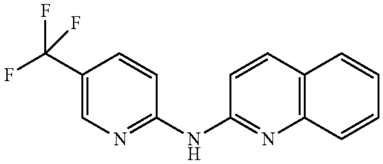 [SMILES: FC(F)(F)c1ccc(Nc2ccc3ccccc3n2)nc1]
23
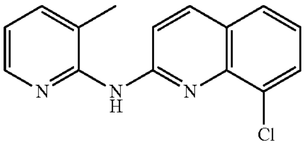 [SMILES: Cc1cccnc1Nc1ccc2cccc(Cl)c2n1]
24
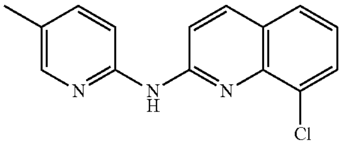 [SMILES: Cc1ccc(Nc2ccc3cccc(Cl)c3n2)nc1]
25
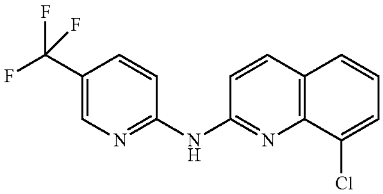 [SMILES: FC(F)(F)c1ccc(Nc2ccc3cccc(Cl)c3n2)nc1]
26

TABLE 1-continued
| (compounds of formula Ia as defined above) | |
|---|---|
| 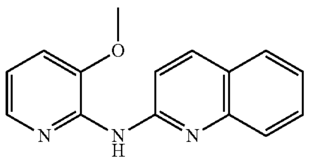 [SMILES: COc1cccnc1Nc1ccc2ccccc2n1] | 27 |
| 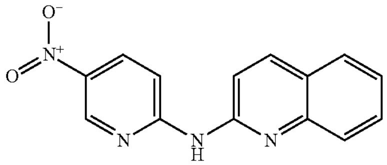 [SMILES: O=[N+]([O-])c1ccc(Nc2ccc3ccccc3n2)nc1] | 28 |
| 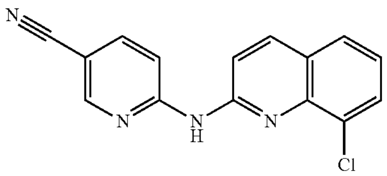 [SMILES: N#Cc1ccc(Nc2ccc3cccc(Cl)c3n2)nc1] | 29 |
| 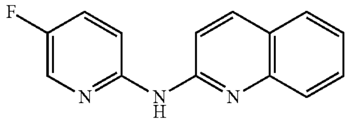 [SMILES: Fc1ccc(Nc2ccc3ccccc3n2)nc1] | 30 |
| 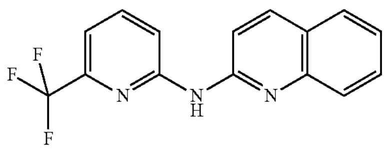 [SMILES: FC(F)(F)c1cccc(Nc2ccc3ccccc3n2)n1] | 31 |
| 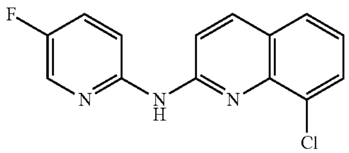 [SMILES: Fc1ccc(Nc2ccc3cccc(Cl)c3n2)nc1] | 32 |
| 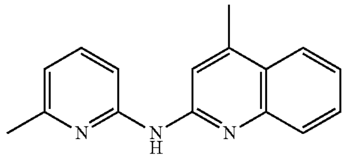 [SMILES: Cc1cccc(Nc2cc(C)c3ccccc3n2)n1] | 33 |
| 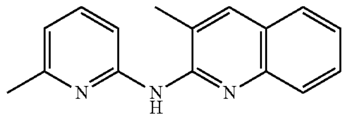 [SMILES: Cc1cccc(Nc2nc3ccccc3cc2C)n1] | 34 |
| 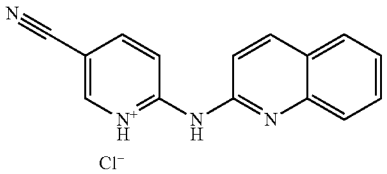 | 35 |

TABLE 1-continued
| (compounds of formula Ia as defined above) | |
|---|---|
| 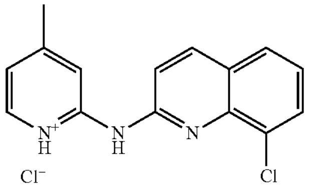 | 36 |
| 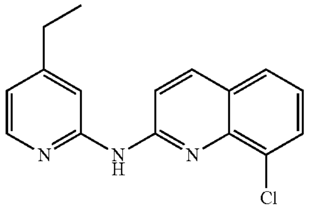 [SMILES: CCc1ccnc(Nc2ccc3cccc(Cl)c3n2)c1] | 37 |
| 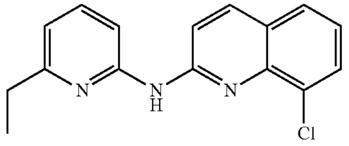 [SMILES: CCc1cccc(Nc2ccc3cccc(Cl)c3n2)n1] | 38 |
| 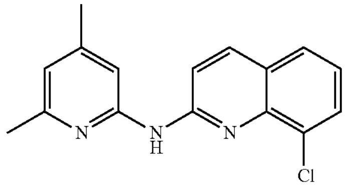 [SMILES: Cc1cc(C)nc(Nc2ccc3cccc(Cl)c3n2)c1] | 39 |
| 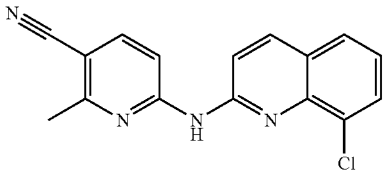 [SMILES: Cc1nc(Nc2ccc3cccc(Cl)c3n2)ccc1C#N] | 40 |
| 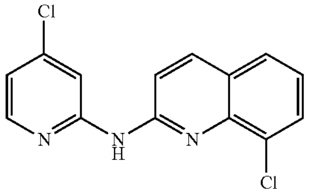 | 41 |
| 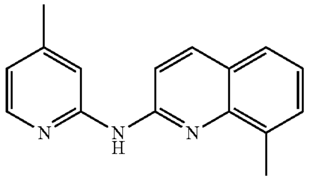 [SMILES: Cc1ccnc(Nc2ccc3cccc(C)c3n2)c1] | 42 |
| 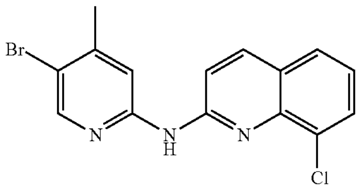 [SMILES: Cc1cc(Nc2ccc3cccc(Cl)c3n2)ncc1Br] | 43 |

TABLE 1-continued
(compounds of formula Ia as defined above)
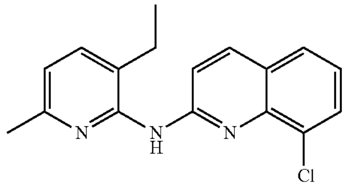 [SMILES: CCc1ccc(C)nc1Nc1ccc2cccc(Cl)c2n1]
44
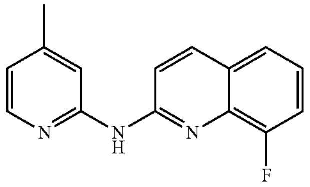 [SMILES: Cc1ccnc(Nc2ccc3cccc(F)c3n2)c1]
45
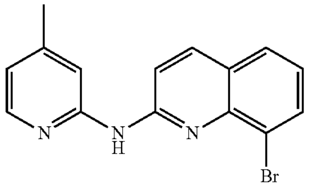 [SMILES: Cc1ccnc(Nc2ccc3cccc(Br)c3n2)c1]
46
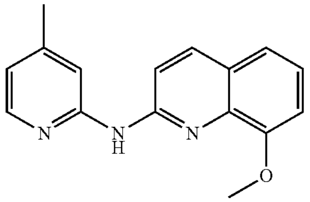 [SMILES: COc1cccc2ccc(Nc3cc(C)ccn3)nc12]
47
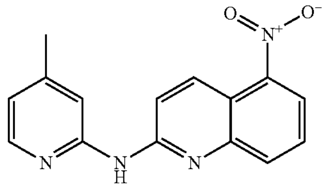 [SMILES: Cc1ccnc(Nc2ccc3c([N+](=O)[O-])cccc3n2)c1]
48
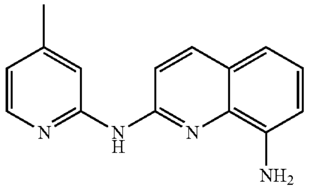 [SMILES: Cc1ccnc(Nc2ccc3cccc(N)c3n2)c1]
49
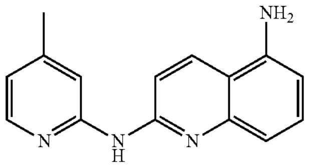 [SMILES: Cc1ccnc(Nc2ccc3c(N)cccc3n2)c1]
50
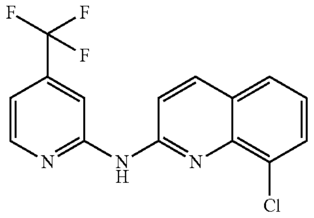 [SMILES: FC(F)(F)c1ccnc(Nc2ccc3cccc(Cl)c3n2)c1]
51

TABLE 1-continued
(compounds of formula Ia as defined above)
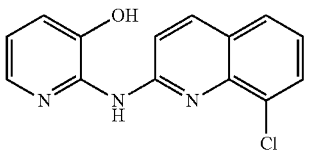 [SMILES: Oc1cccnc1Nc1ccc2cccc(Cl)c2n1]
52
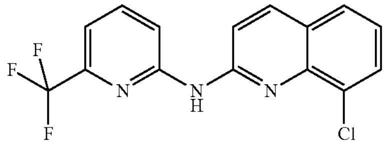 [SMILES: FC(F)(F)c1cccc(Nc2ccc3cccc(Cl)c3n2)n1]
53
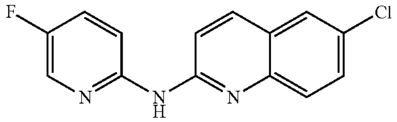 [SMILES: Fc1ccc(Nc2ccc3cc(Cl)ccc3n2)nc1]
54
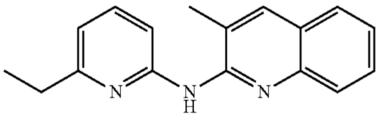 [SMILES: CCc1cccc(Nc2nc3ccccc3cc2C)n1]
55
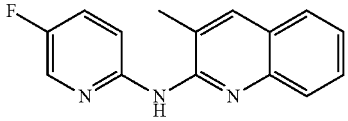 [SMILES: Cc1cc2ccccc2nc1Nc1ccc(F)cn1]
56
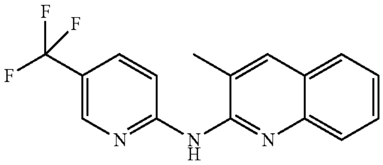 [SMILES: Cc1cc2ccccc2nc1Nc1ccc(C(F)(F)F)cn1]
57
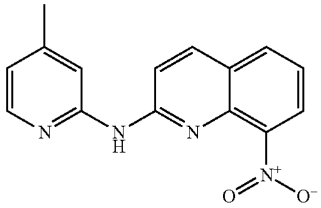 [SMILES: Cc1ccnc(Nc2ccc3cccc([N+](=O)[O-])c3n2)c1]
58
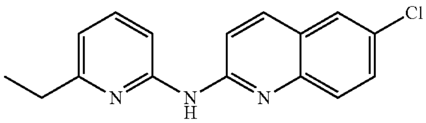 [SMILES: CCc1cccc(Nc2ccc3cc(Cl)ccc3n2)n1]
59
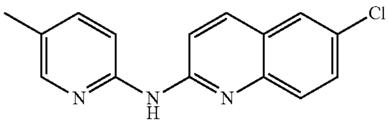 [SMILES: Cc1ccc(Nc2ccc3cc(Cl)ccc3n2)nc1]
60
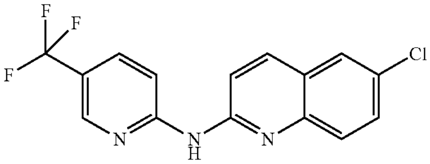 [SMILES: FC(F)(F)c1ccc(Nc2ccc3cc(Cl)ccc3n2)nc1]
61

TABLE 1-continued
(compounds of formula Ia as defined above)
62
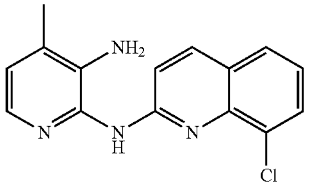 [SMILES: Cc1ccnc(Nc2ccc3cccc(Cl)c3n2)c1N]
63
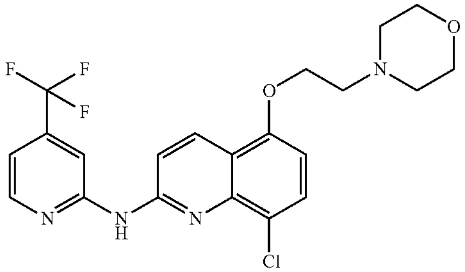 [SMILES: FC(F)(F)c1ccnc(Nc2ccc3c(OCCN4CCOCC4)ccc(Cl)c3n2)c1]
64
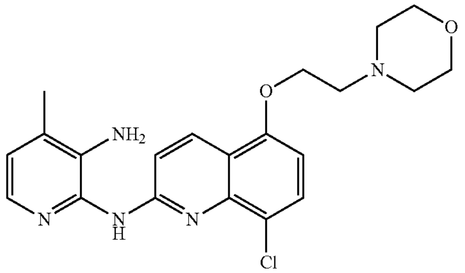 [SMILES: Cc1ccnc(Nc2ccc3c(OCCN4CCOCC4)ccc(Cl)c3n2)c1N]
65
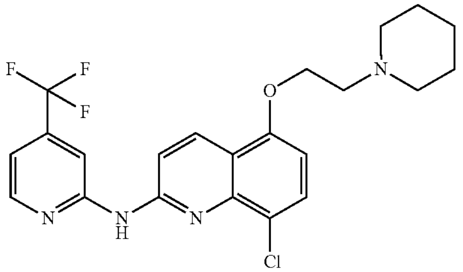 [SMILES: FC(F)(F)c1ccnc(Nc2ccc3c(OCCN4CCCCC4)ccc(Cl)c3n2)c1]
66
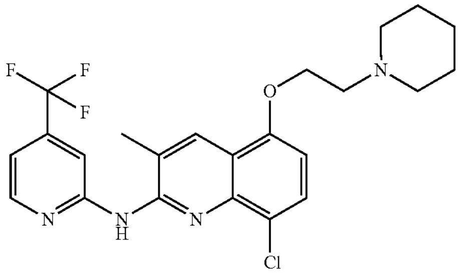 [SMILES: Cc1cc2c(OCCN3CCCCC3)ccc(Cl)c2nc1Nc1cc(C(F)(F)F)ccn1]
67
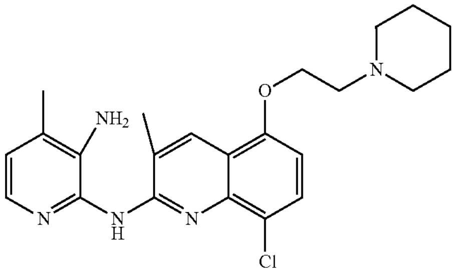 [SMILES: Cc1cc2c(OCCN3CCCCC3)ccc(Cl)c2nc1Nc1nccc(C)c1N]

TABLE 1-continued
(compounds of formula Ia as defined above)
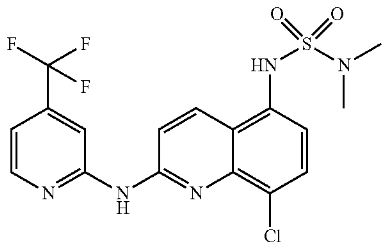 [SMILES: CN(C)S(=O)(=O)Nc1ccc(Cl)c2nc(Nc3cc(C(F)(F)F)ccn3)ccc12]
68
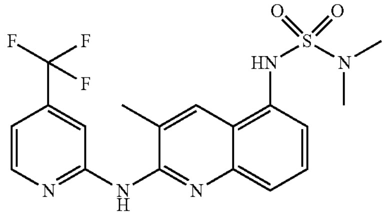 [SMILES: Cc1cc2c(NS(=O)(=O)N(C)C)cccc2nc1Nc1cc(C(F)(F)F)ccn1]
69
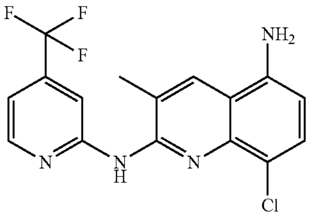 [SMILES: Cc1cc2c(N)ccc(Cl)c2nc1Nc1cc(C(F)(F)F)ccn1]
70
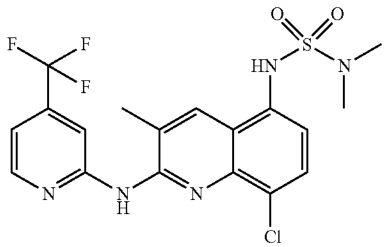 [SMILES: Cc1cc2c(NS(=O)(=O)N(C)C)ccc(Cl)c2nc1Nc1cc(C(F)(F)F)ccn1]
71
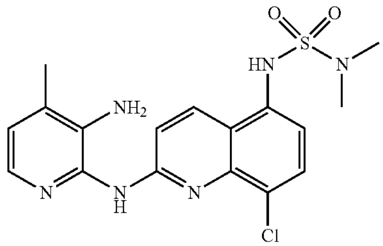 [SMILES: Cc1ccnc(Nc2ccc3c(NS(=O)(=O)N(C)C)ccc(Cl)c3n2)c1N]
72
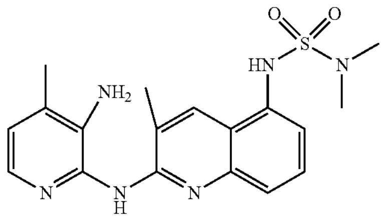 [SMILES: Cc1cc2c(NS(=O)(=O)N(C)C)cccc2nc1Nc1nccc(C)c1N]
73

TABLE 1-continued
(compounds of formula Ia as defined above)
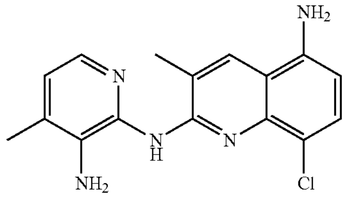 [SMILES: Cc1cc2c(N)ccc(Cl)c2nc1Nc1nccc(C)c1N]
74
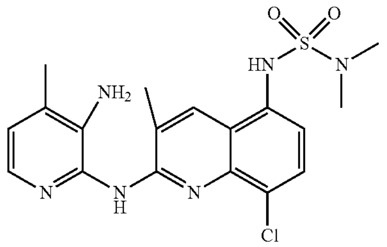 [SMILES: Cc1cc2c(NS(=O)(=O)N(C)C)ccc(Cl)c2nc1Nc1nccc(C)c1N]
75
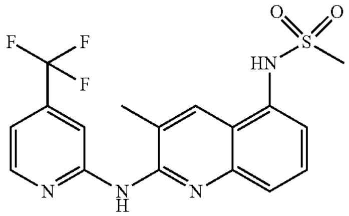 [SMILES: Cc1cc2c(NS(C)(=O)=O)cccc2nc1Nc1cc(C(F)(F)F)ccn1]
76
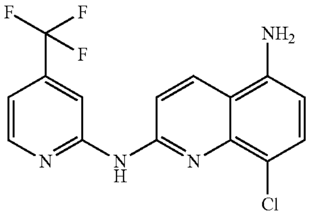 [SMILES: Nc1ccc(Cl)c2nc(Nc3cc(C(F)(F)F)ccn3)ccc12]
77
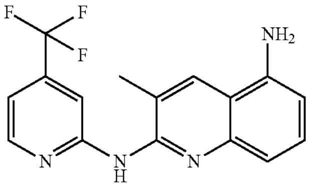 [SMILES: Cc1cc2c(N)cccc2nc1Nc1cc(C(F)(F)F)ccn1]
78
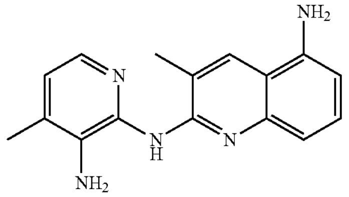 [SMILES: Cc1cc2c(N)cccc2nc1Nc1nccc(C)c1N]
79
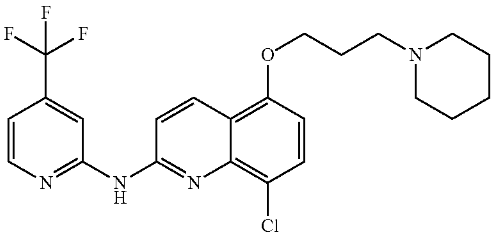 [SMILES: FC(F)(F)c1ccnc(Nc2ccc3c(OCCCN4CCCCC4)ccc(Cl)c3n2)c1]
80

TABLE 1-continued
| (compounds of formula Ia as defined above) | |
|---|---|
| 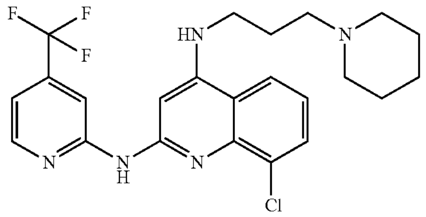 [SMILES: FC(F)(F)c1ccnc(Nc2cc(NCCCN3CCCCC3)c3cccc(Cl)c3n2)c1] | 81 |
| 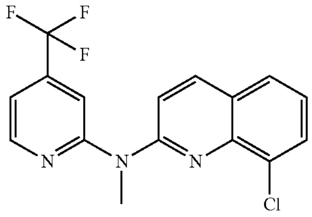 | 82 |
| 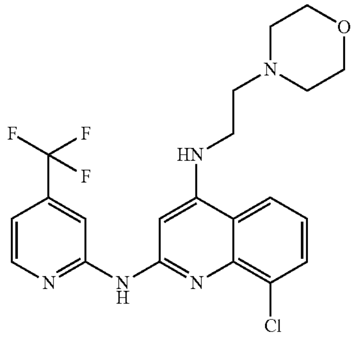 [SMILES: FC(F)(F)c1ccnc(Nc2cc(NCCN3CCOCC3)c3cccc(Cl)c3n2)c1] | 83 |
| 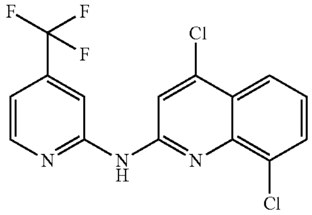 [SMILES: FC(F)(F)c1ccnc(Nc2cc(Cl)c3cccc(Cl)c3n2)c1] | 84 |
| 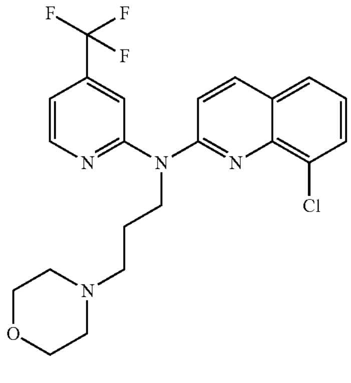 [SMILES: FC(F)(F)c1ccnc(N(CCCN2CCOCC2)c2ccc3cccc(Cl)c3n2)c1] | 85 |

TABLE 1-continued
(compounds of formula Ia as defined above)
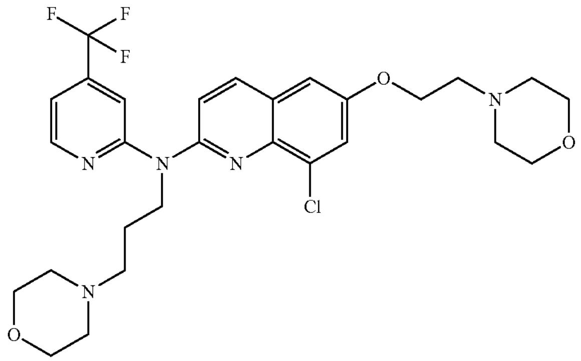 [SMILES: FC(F)(F)c1ccnc(N(CCCN2CCOCC2)c2ccc3cc(OCCN4CCOCC4)cc(Cl)c3n2)c1]
86
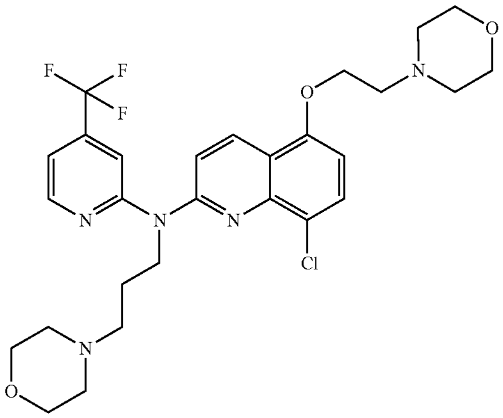 [SMILES: FC(F)(F)c1ccnc(N(CCCN2CCOCC2)c2ccc3c(OCCN4CCOCC4)ccc(Cl)c3n2)c1]
87
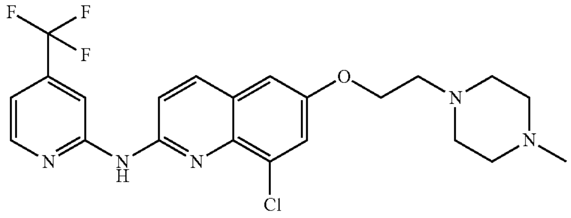 [SMILES: CN1CCN(CCOc2cc(Cl)c3nc(Nc4cc(C(F)(F)F)ccn4)ccc3c2)CC1]
88
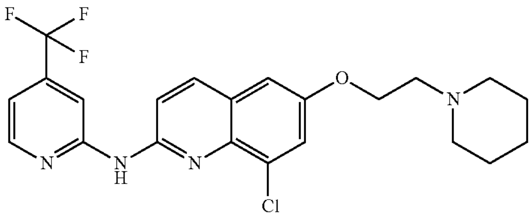 [SMILES: FC(F)(F)c1ccnc(Nc2ccc3cc(OCCN4CCCCC4)cc(Cl)c3n2)c1]
89
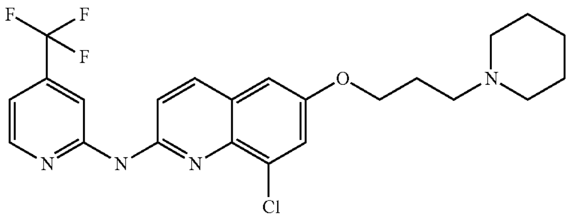 [SMILES: FC(F)(F)c1ccnc(Nc2ccc3cc(OCCCN4CCCCC4)cc(Cl)c3n2)c1]
90

TABLE 1-continued

| (compounds of formula Ia as defined above) | |
|---|---|
| 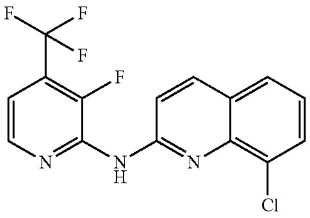 [SMILES: Fc1c(C(F)(F)F)ccnc1Nc1ccc2cccc(Cl)c2n1] | 91 |
| 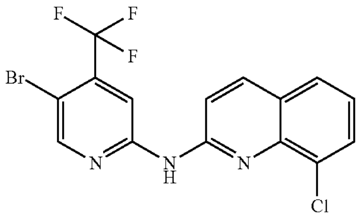 [SMILES: FC(F)(F)c1cc(Nc2ccc3cccc(Cl)c3n2)ncc1Br] | 92 |
| 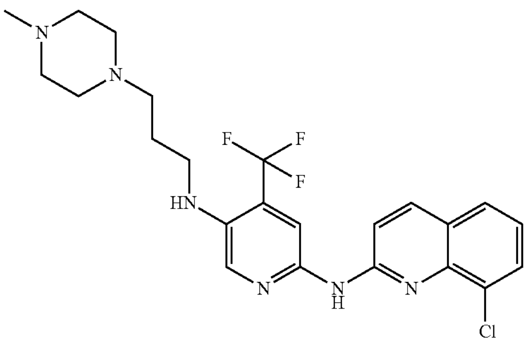 [SMILES: CN1CCN(CCCNc2cnc(Nc3ccc4cccc(Cl)c4n3)cc2C(F)(F)F)CC1] | 93 |
| 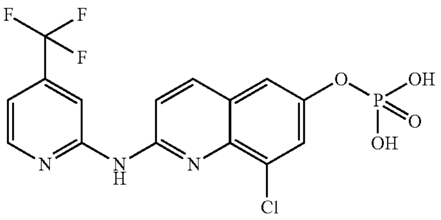 [SMILES: O=P(O)(O)Oc1cc(Cl)c2nc(Nc3cc(C(F)(F)F)ccn3)ccc2c1] | 94 |

or a pharmaceutically acceptable salt thereof.

In some embodiments, the present invention provides a method for treating a viral infection, or an inflammatory disease, disorder or condition, or a cancer, comprising administering to a patient in need thereof a compound selected from Table 2:

TABLE 2

| (compounds of formula (Ib) as defined above) | |
|---|---|
| 95 | 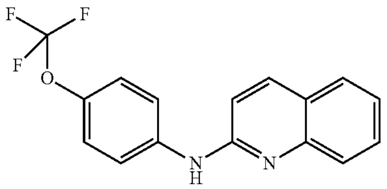 [SMILES: FC(F)(F)Oc1ccc(Nc2ccc3ccccc3n2)cc1] |

TABLE 2-continued
| (compounds of formula (Ib) as defined above) | |
|---|---|
| 96 | 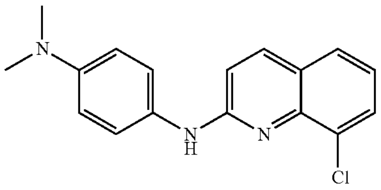 [SMILES: CN(C)c1ccc(Nc2ccc3cccc(Cl)c3n2)cc1] |
| 97 | 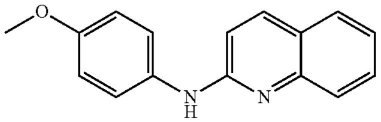 [SMILES: COc1ccc(Nc2ccc3ccccc3n2)cc1] |
| 98 | 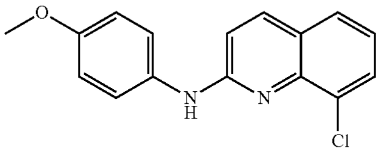 [SMILES: COc1ccc(Nc2ccc3cccc(Cl)c3n2)cc1] |
| 99 | 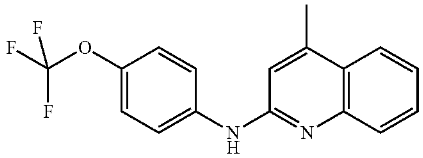 [SMILES: Cc1cc(Nc2ccc(OC(F)(F)F)cc2)nc2ccccc12] |
| 100 | 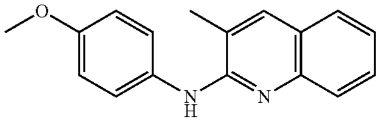 [SMILES: COc1ccc(Nc2nc3ccccc3cc2C)cc1] |
| 101 | 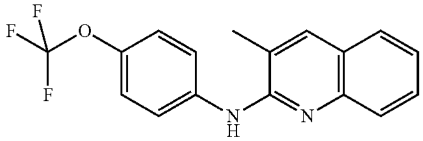 [SMILES: Cc1cc2ccccc2nc1Nc1ccc(OC(F)(F)F)cc1] |
| 102 | 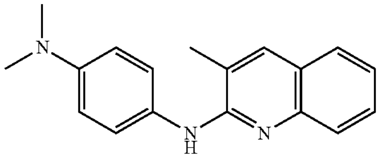 [SMILES: Cc1cc2ccccc2nc1Nc1ccc(N(C)C)cc1] |
| 103 | 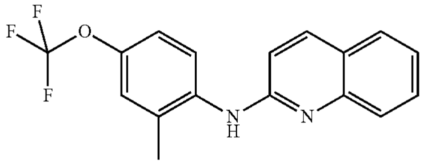 [SMILES: Cc1cc(OC(F)(F)F)ccc1Nc1ccc2ccccc2n1] |
| 104 | 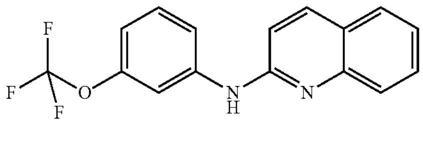 [SMILES: FC(F)(F)Oc1cccc(Nc2ccc3ccccc3n2)c1] |

TABLE 2-continued
(compounds of formula (Ib) as defined above)
105
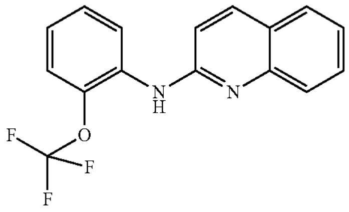 [SMILES: FC(F)(F)Oc1ccccc1Nc1ccc2ccccc2n1]
106
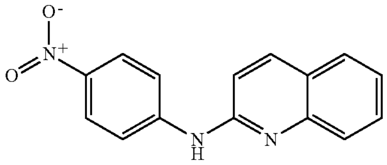
107
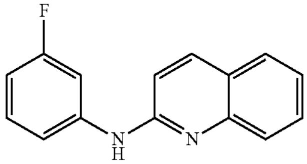 [SMILES: Fc1cccc(Nc2ccc3ccccc3n2)c1]
108
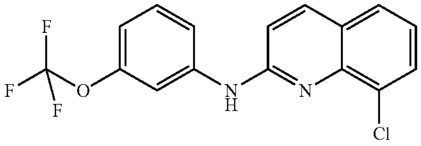 [SMILES: FC(F)(F)Oc1cccc(Nc2ccc3cccc(Cl)c3n2)c1]
109
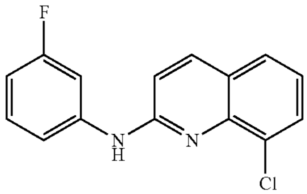 [SMILES: Fc1cccc(Nc2ccc3cccc(Cl)c3n2)c1]
110
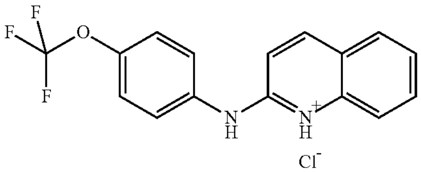 [SMILES: FC(F)(F)Oc1ccc(Nc2ccc3ccccc3n2)cc1 ; Cl]
111
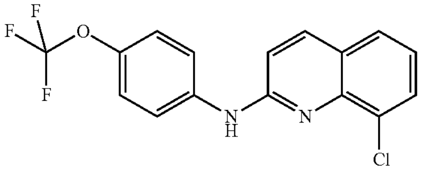
112
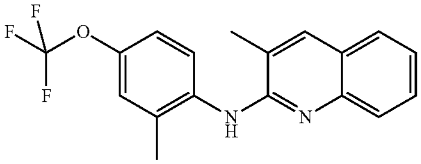 [SMILES: Cc1cc(OC(F)(F)F)ccc1Nc1nc2ccccc2cc1C]
113
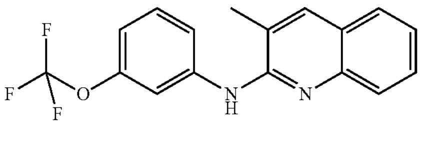 [SMILES: Cc1cc2ccccc2nc1Nc1cccc(OC(F)(F)F)c1]

TABLE 2-continued
| (compounds of formula (Ib) as defined above) | |
|---|---|
| 114 | 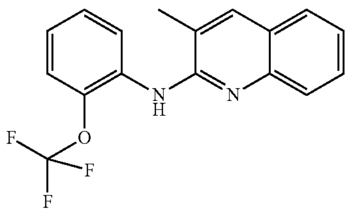 [SMILES: Cc1cc2ccccc2nc1Nc1ccccc1OC(F)(F)F] |
| 115 | 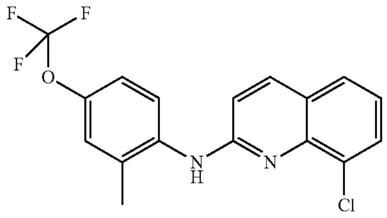 [SMILES: Cc1cc(OC(F)(F)F)ccc1Nc1ccc2cccc(Cl)c2n1] |
| 116 | 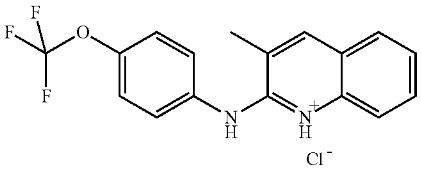 [SMILES: Cc1cc2ccccc2nc1Nc1ccc(OC(F)(F)F)cc1 ; Cl] |
| 117 | 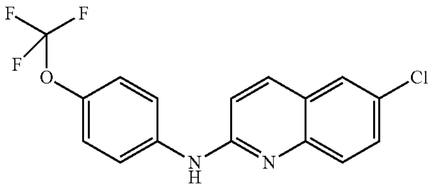 [SMILES: FC(F)(F)Oc1ccc(Nc2ccc3cc(Cl)ccc3n2)cc1] |
| 118 | 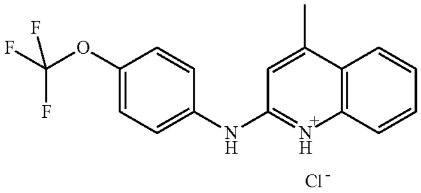 [SMILES: Cc1cc(Nc2ccc(OC(F)(F)F)cc2)nc2ccccc12 ; Cl] |
| 119 | 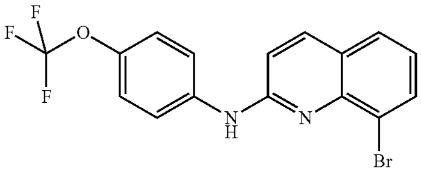 [SMILES: FC(F)(F)Oc1ccc(Nc2ccc3cccc(Br)c3n2)cc1] |
| 120 | 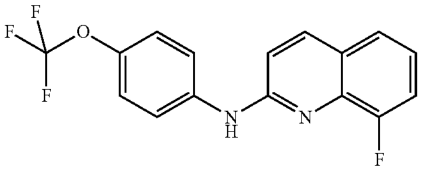 [SMILES: Fc1cccc2ccc(Nc3ccc(OC(F)(F)F)cc3)nc12] |
| 121 | 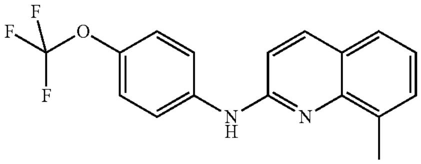 [SMILES: Cc1cccc2ccc(Nc3ccc(OC(F)(F)F)cc3)nc12] |

TABLE 2-continued
| (compounds of formula (Ib) as defined above) | |
|---|---|
| 122 | 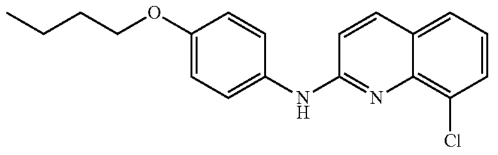 [SMILES: CCCCOc1ccc(Nc2ccc3cccc(Cl)c3n2)cc1] |
| 123 | 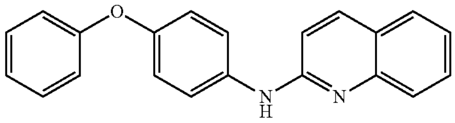 [SMILES: c1ccc(Oc2ccc(Nc3ccc4ccccc4n3)cc2)cc1] |
| 124 | 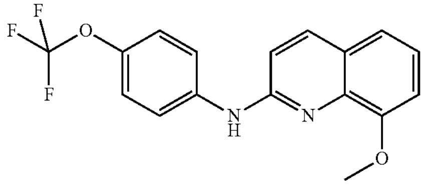 [SMILES: COc1cccc2ccc(Nc3ccc(OC(F)(F)F)cc3)nc12] |
| 125 | 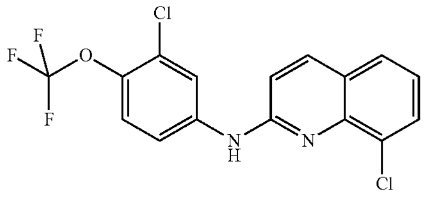 [SMILES: FC(F)(F)Oc1ccc(Nc2ccc3cccc(Cl)c3n2)cc1Cl] |
| 126 | 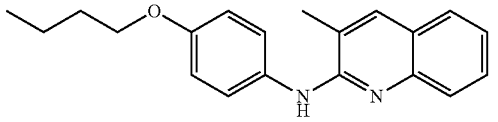 [SMILES: CCCCOc1ccc(Nc2nc3ccccc3cc2C)cc1] |
| 127 | 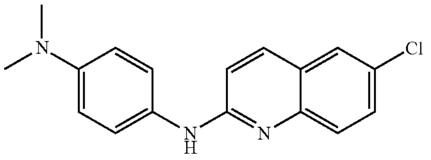 [SMILES: CN(C)c1ccc(Nc2ccc3cc(Cl)ccc3n2)cc1] |
| 128 | 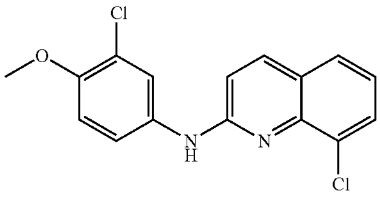 [SMILES: COc1ccc(Nc2ccc3cccc(Cl)c3n2)cc1Cl] |
| 129 | 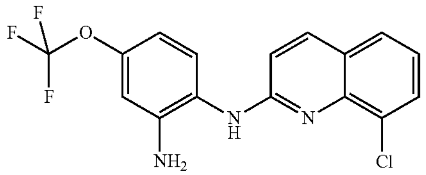 [SMILES: Nc1cc(OC(F)(F)F)ccc1Nc1ccc2cccc(Cl)c2n1] |

TABLE 2-continued
| (compounds of formula (Ib) as defined above) | |
|---|---|
| 130 | 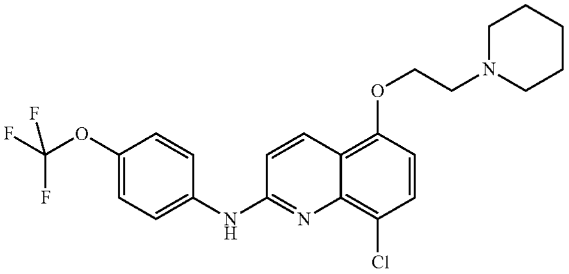 [SMILES: FC(F)(F)Oc1ccc(Nc2ccc3c(OCCN4CCCCC4)ccc(Cl)c3n2)cc1] |
| 131 | 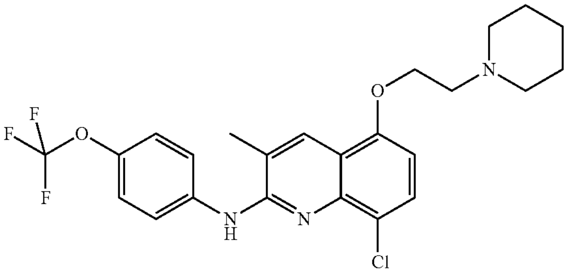 [SMILES: Cc1cc2c(OCCN3CCCCC3)ccc(Cl)c2nc1Nc1ccc(OC(F)(F)F)cc1] |
| 132 | 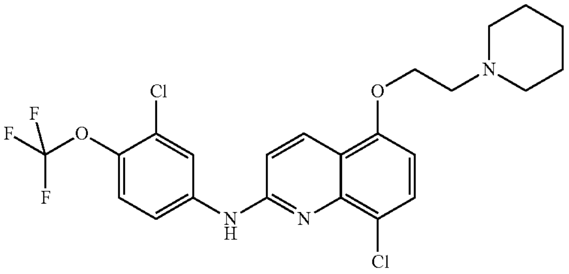 [SMILES: FC(F)(F)Oc1ccc(Nc2ccc3c(OCCN4CCCCC4)ccc(Cl)c3n2)cc1Cl] |
| 133 | 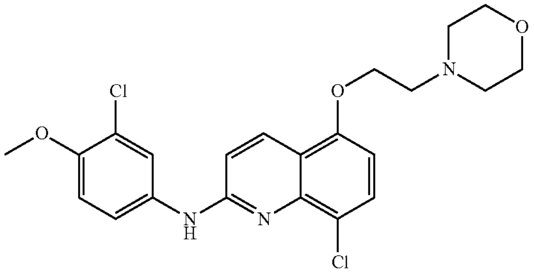 [SMILES: COc1ccc(Nc2ccc3c(OCCN4CCOCC4)ccc(Cl)c3n2)cc1Cl] |
| 134 | 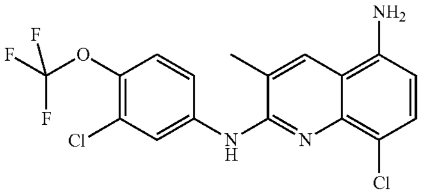 [SMILES: Cc1cc2c(N)ccc(Cl)c2nc1Nc1ccc(OC(F)(F)F)c(Cl)c1] |
| 135 | 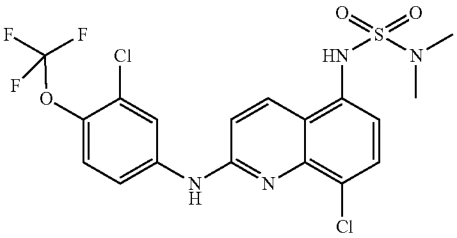 [SMILES: CN(C)S(=O)(=O)Nc1ccc(Cl)c2nc(Nc3ccc(OC(F)(F)F)c(Cl)c3)ccc12] |

TABLE 2-continued
| (compounds of formula (Ib) as defined above) | |
|---|---|
| 136 | 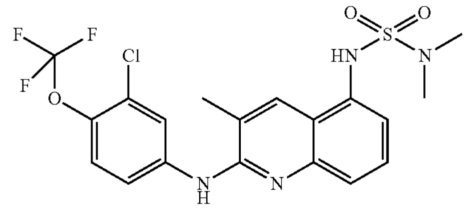 [SMILES: Cc1cc2c(NS(=O)(=O)N(C)C)cccc2nc1Nc1ccc(OC(F)(F)F)c(Cl)c1] |
| 137 | 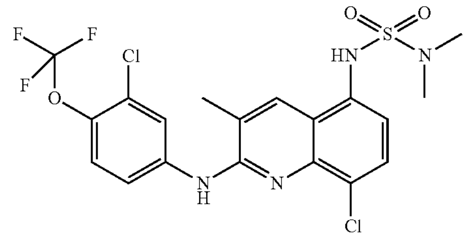 [SMILES: Cc1cc2c(NS(=O)(=O)N(C)C)ccc(Cl)c2nc1Nc1ccc(OC(F)(F)F)c(Cl)c1] |
| 138 | 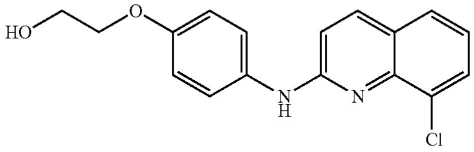 [SMILES: OCCOc1ccc(Nc2ccc3cccc(Cl)c3n2)cc1] |
| 139 | 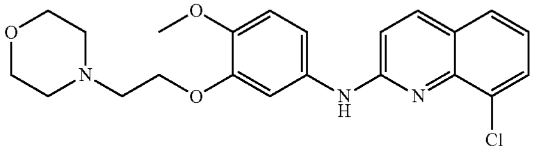 [SMILES: COc1ccc(Nc2ccc3cccc(Cl)c3n2)cc1OCCN1CCOCC1] |
| 140 | 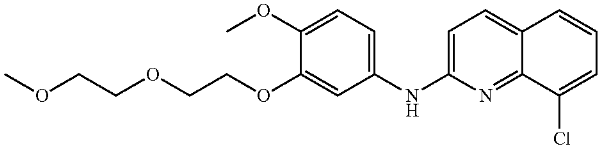 [SMILES: COCCOCCOc1cc(Nc2ccc3cccc(Cl)c3n2)ccc1OC] |
| 141 | 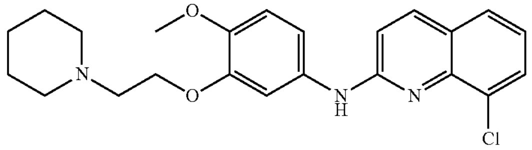 [SMILES: COc1ccc(Nc2ccc3cccc(Cl)c3n2)cc1OCCN1CCCCC1] |
| 142 | 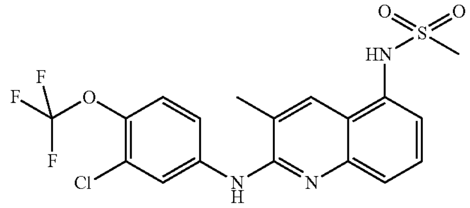 [SMILES: Cc1cc2c(NS(C)(=O)=O)cccc2nc1Nc1ccc(OC(F)(F)F)c(Cl)c1] |
| 143 | 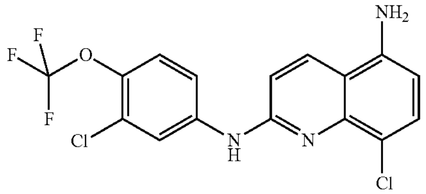 [SMILES: Nc1ccc(Cl)c2nc(Nc3ccc(OC(F)(F)F)c(Cl)c3)ccc12] |

TABLE 2-continued
(compounds of formula (Ib) as defined above)
144
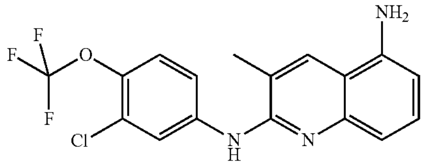 [SMILES: Cc1cc2c(N)cccc2nc1Nc1ccc(OC(F)(F)F)c(Cl)c1]
145
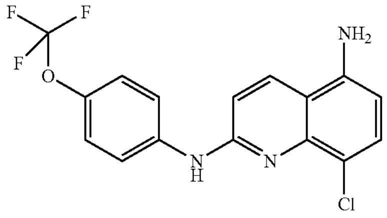 [SMILES: Nc1ccc(Cl)c2nc(Nc3ccc(OC(F)(F)F)cc3)ccc12]
146
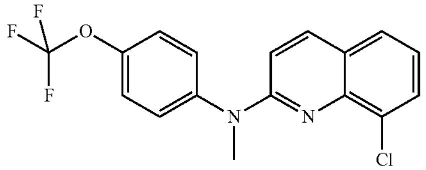 [SMILES: CN(c1ccc(OC(F)(F)F)cc1)c1ccc2cccc(Cl)c2n1]
147
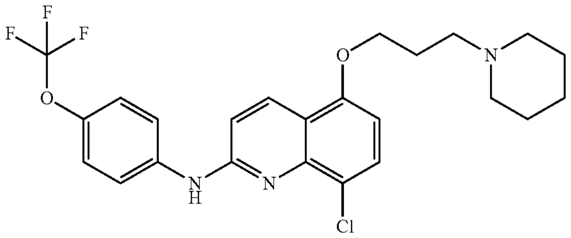 [SMILES: FC(F)(F)Oc1ccc(Nc2ccc3c(OCCCN4CCCCC4)ccc(Cl)c3n2)cc1]
148
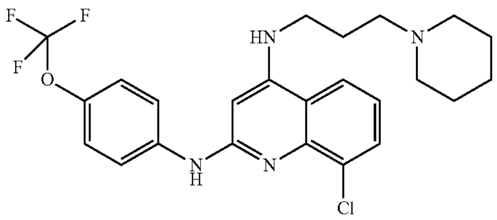 [SMILES: FC(F)(F)Oc1ccc(Nc2cc(NCCCN3CCCCC3)c3cccc(Cl)c3n2)cc1]
149
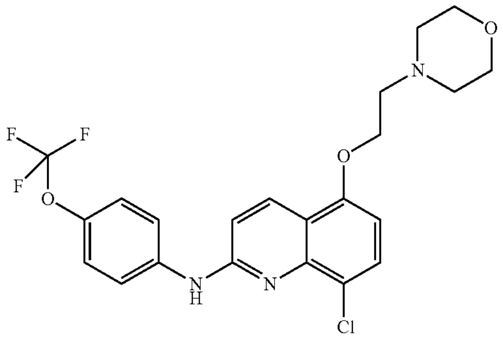 [SMILES: FC(F)(F)Oc1ccc(Nc2ccc3c(OCCN4CCOCC4)ccc(Cl)c3n2)cc1]
150
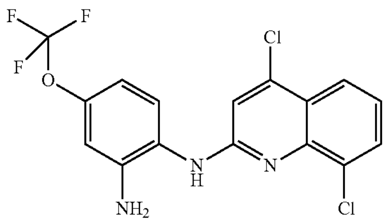 [SMILES: Nc1cc(OC(F)(F)F)ccc1Nc1cc(Cl)c2cccc(Cl)c2n1]

TABLE 2-continued
(compounds of formula (Ib) as defined above)
151
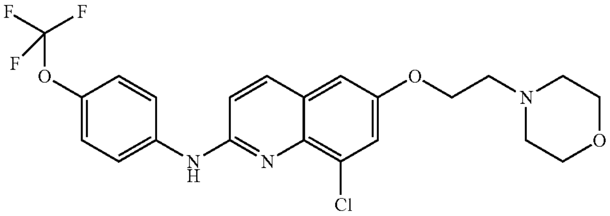 [SMILES: FC(F)(F)Oc1ccc(Nc2ccc3cc(OCCN4CCOCC4)cc(Cl)c3n2)cc1]
152
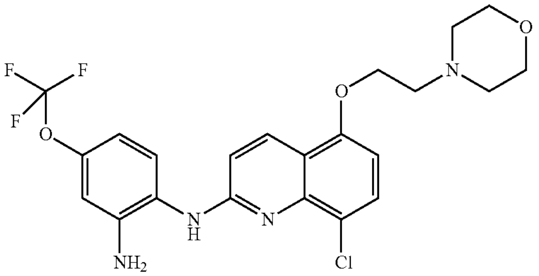 [SMILES: Nc1cc(OC(F)(F)F)ccc1Nc1ccc2c(OCCN3CCOCC3)ccc(Cl)c2n1]
153
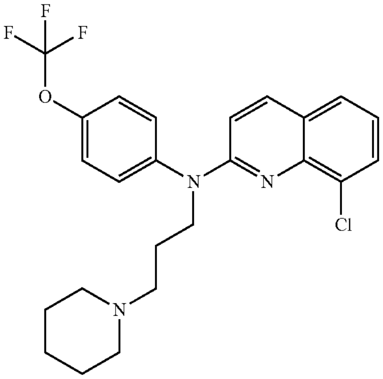 [SMILES: FC(F)(F)Oc1ccc(N(CCCN2CCCCC2)c2ccc3cccc(Cl)c3n2)cc1]
154
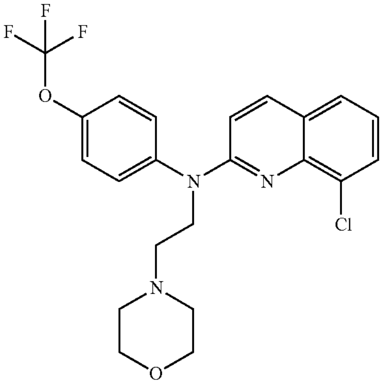 [SMILES: FC(F)(F)Oc1ccc(N(CCN2CCOCC2)c2ccc3cccc(Cl)c3n2)cc1]

TABLE 2-continued
| (compounds of formula (Ib) as defined above) | |
|---|---|
| 155 | 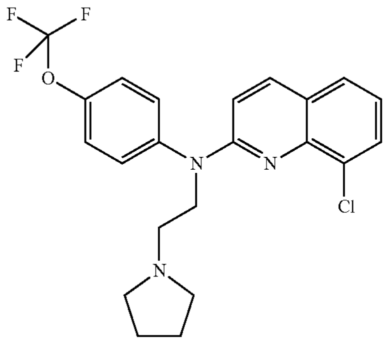 [SMILES: FC(F)(F)Oc1ccc(N(CCN2CCCC2)c2ccc3cccc(Cl)c3n2)cc1] |
| 156 | 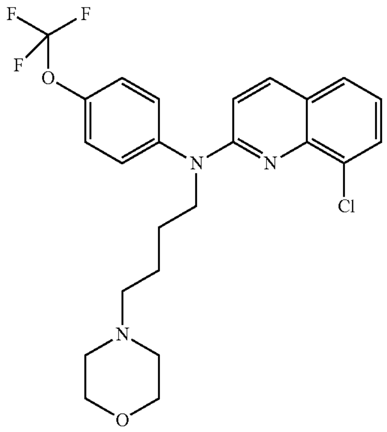 [SMILES: FC(F)(F)Oc1ccc(N(CCCCN2CCOCC2)c2ccc3cccc(Cl)c3n2)cc1] |
| 157 | 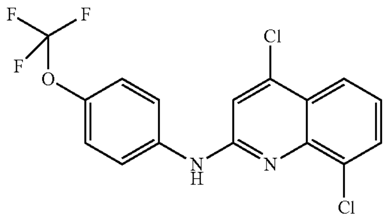 [SMILES: FC(F)(F)Oc1ccc(Nc2cc(Cl)c3cccc(Cl)c3n2)cc1] |
| 158 | 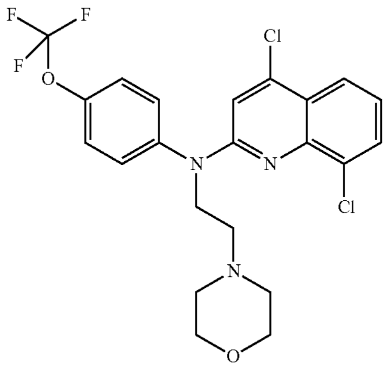 [SMILES: FC(F)(F)Oc1ccc(N(CCN2CCOCC2)c2cc(Cl)c3cccc(Cl)c3n2)cc1] |

TABLE 2-continued
| (compounds of formula (Ib) as defined above) | |
|---|---|
| 159 | 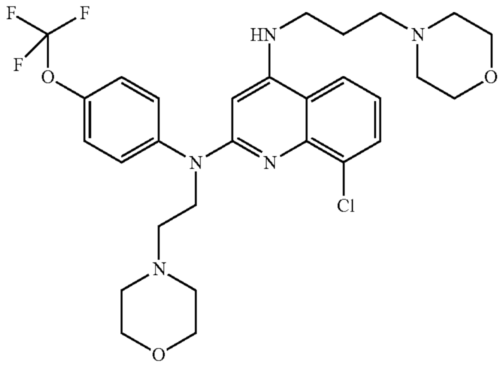 [SMILES: FC(F)(F)Oc1ccc(N(CCN2CCOCC2)c2cc(NCCCN3CCOCC3)c3cccc(Cl)c3n2)cc1] |
| 160 | 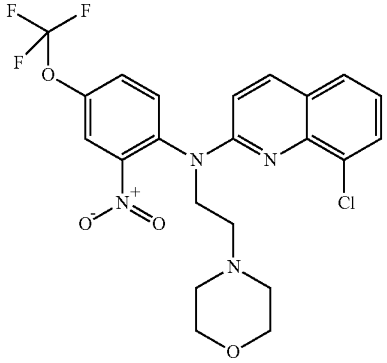 |
| 161 | 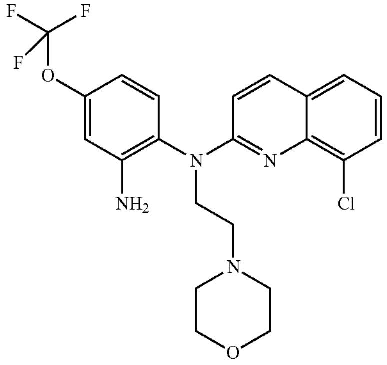 [SMILES: Nc1cc(OC(F)(F)F)ccc1N(CCN1CCOCC1)c1ccc2cccc(Cl)c2n1] |
| 162 | 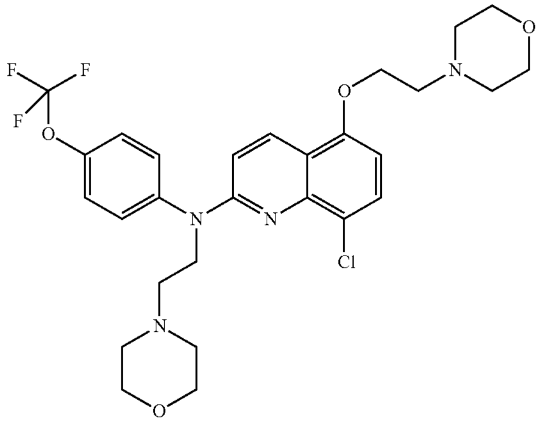 [SMILES: FC(F)(F)Oc1ccc(N(CCN2CCOCC2)c2ccc3c(OCCN4CCOCC4)ccc(Cl)c3n2)cc1] |

TABLE 2-continued
| (compounds of formula (Ib) as defined above) | |
|---|---|
| 163 | 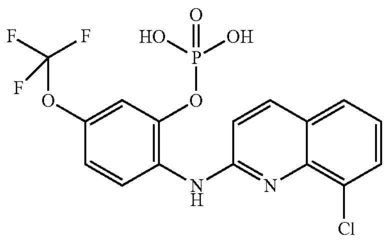 [SMILES: O=P(O)(O)Oc1cc(OC(F)(F)F)ccc1Nc1ccc2cccc(Cl)c2n1] |
| 164 | 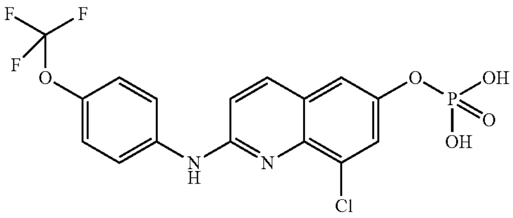 [SMILES: O=P(O)(O)Oc1cc(Cl)c2nc(Nc3ccc(OC(F)(F)F)cc3)ccc2c1] |
| 95 | 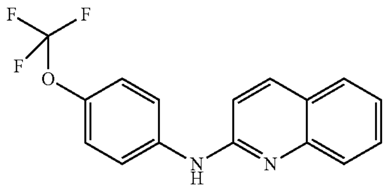 [SMILES: FC(F)(F)Oc1ccc(Nc2ccc3ccccc3n2)cc1] |
| 96 | 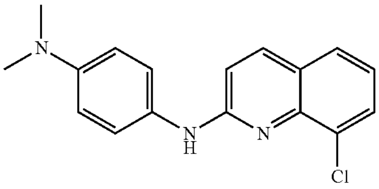 [SMILES: CN(C)c1ccc(Nc2ccc3cccc(Cl)c3n2)cc1] |
| 97 | 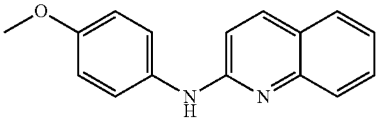 [SMILES: COc1ccc(Nc2ccc3ccccc3n2)cc1] |
| 98 | 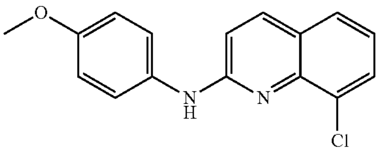 [SMILES: COc1ccc(Nc2ccc3cccc(Cl)c3n2)cc1] |
| 99 | 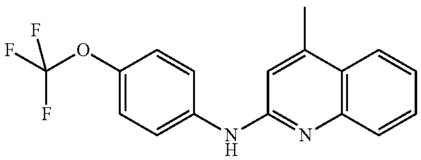 [SMILES: Cc1cc(Nc2ccc(OC(F)(F)F)cc2)nc2ccccc12] |
| 100 | 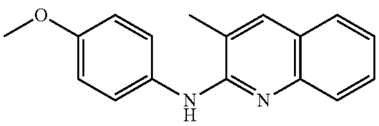 [SMILES: COc1ccc(Nc2nc3ccccc3cc2C)cc1] |

TABLE 2-continued
| (compounds of formula (Ib) as defined above) | |
|---|---|
| 101 | 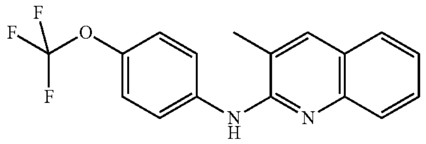 [SMILES: Cc1cc2ccccc2nc1Nc1ccc(OC(F)(F)F)cc1] |
| 102 | 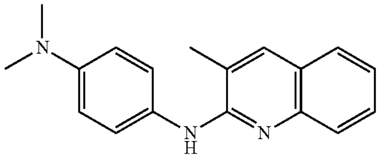 [SMILES: Cc1cc2ccccc2nc1Nc1ccc(N(C)C)cc1] |
| 103 | 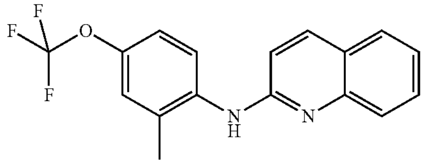 [SMILES: Cc1cc(OC(F)(F)F)ccc1Nc1ccc2ccccc2n1] |
| 104 | 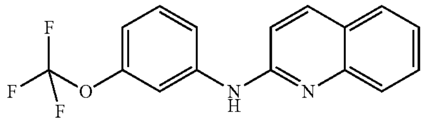 [SMILES: FC(F)(F)Oc1cccc(Nc2ccc3ccccc3n2)c1] |
| 105 | 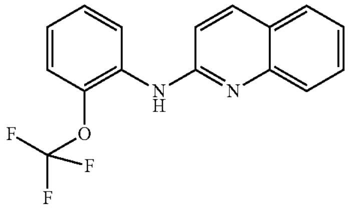 [SMILES: FC(F)(F)Oc1ccccc1Nc1ccc2ccccc2n1] |
| 106 | 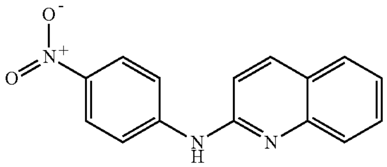 |
| 107 | 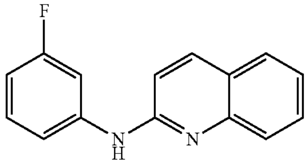 [SMILES: Fc1cccc(Nc2ccc3ccccc3n2)c1] |
| 108 | 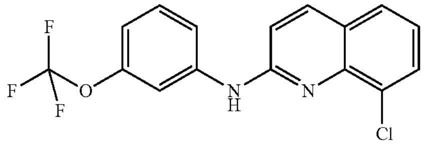 [SMILES: FC(F)(F)Oc1cccc(Nc2ccc3cccc(Cl)c3n2)c1] |
| 109 | 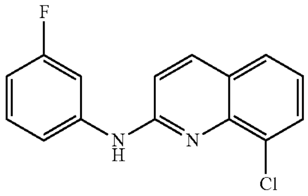 [SMILES: Fc1cccc(Nc2ccc3cccc(Cl)c3n2)c1] |

TABLE 2-continued
| (compounds of formula (Ib) as defined above) | |
|---|---|
| 110 | 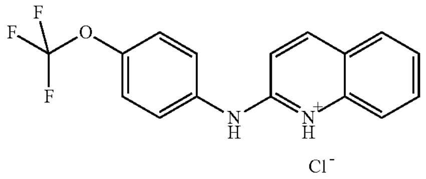 [SMILES: FC(F)(F)Oc1ccc(Nc2ccc3ccccc3n2)cc1 ; Cl] |
| 111 | 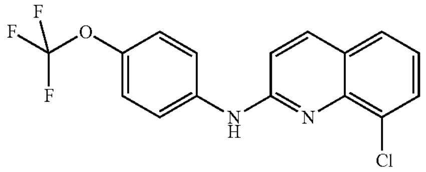 |
| 112 | 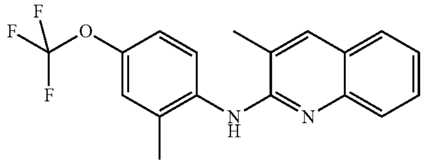 [SMILES: Cc1cc(OC(F)(F)F)ccc1Nc1nc2ccccc2cc1C] |
| 113 | 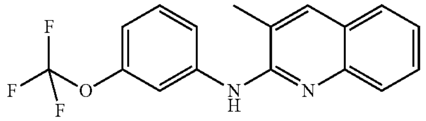 [SMILES: Cc1cc2ccccc2nc1Nc1cccc(OC(F)(F)F)c1] |
| 114 | 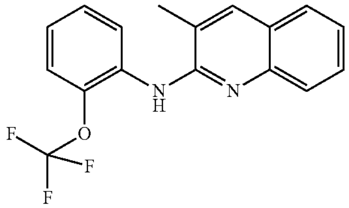 [SMILES: Cc1cc2ccccc2nc1Nc1ccccc1OC(F)(F)F] |
| 115 | 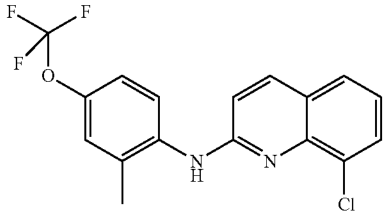 [SMILES: Cc1cc(OC(F)(F)F)ccc1Nc1ccc2cccc(Cl)c2n1] |
| 116 | 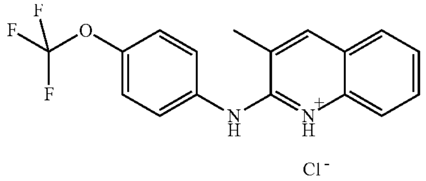 [SMILES: Cc1cc2ccccc2nc1Nc1ccc(OC(F)(F)F)cc1 ; Cl] |
| 117 | 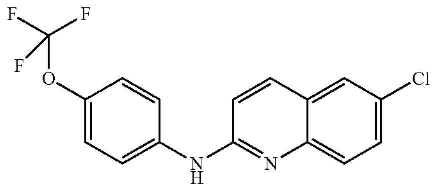 [SMILES: FC(F)(F)Oc1ccc(Nc2ccc3cc(Cl)ccc3n2)cc1] |

TABLE 2-continued
(compounds of formula (Ib) as defined above)
118
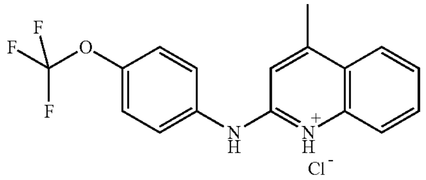 [SMILES: Cc1cc(Nc2ccc(OC(F)(F)F)cc2)nc2ccccc12 ; Cl]
119
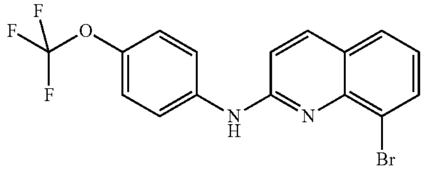 [SMILES: FC(F)(F)Oc1ccc(Nc2ccc3cccc(Br)c3n2)cc1]
120
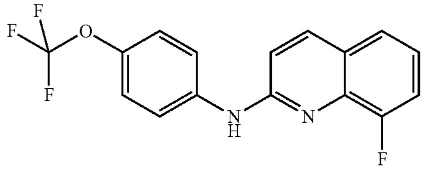 [SMILES: Fc1cccc2ccc(Nc3ccc(OC(F)(F)F)cc3)nc12]
121
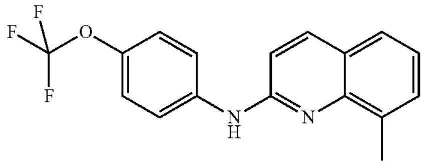 [SMILES: Cc1cccc2ccc(Nc3ccc(OC(F)(F)F)cc3)nc12]
122
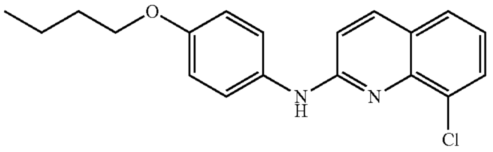 [SMILES: CCCCOc1ccc(Nc2ccc3cccc(Cl)c3n2)cc1]
123
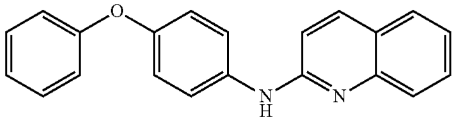 [SMILES: c1ccc(Oc2ccc(Nc3ccc4ccccc4n3)cc2)cc1]
124
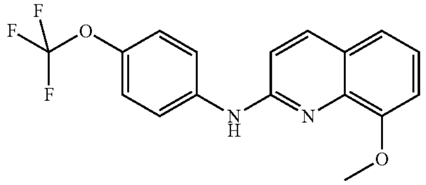 [SMILES: COc1cccc2ccc(Nc3ccc(OC(F)(F)F)cc3)nc12]
125
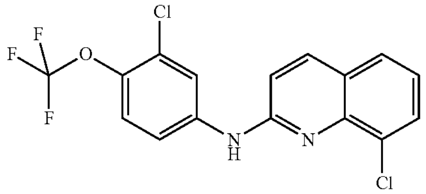 [SMILES: FC(F)(F)Oc1ccc(Nc2ccc3cccc(Cl)c3n2)cc1Cl]
126
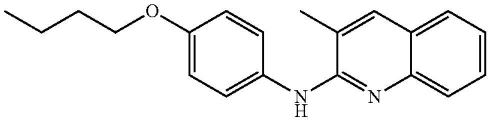 [SMILES: CCCCOc1ccc(Nc2nc3ccccc3cc2C)cc1]

TABLE 2-continued
(compounds of formula (Ib) as defined above)
127
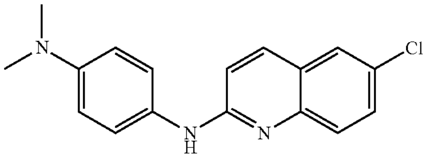 [SMILES: CN(C)c1ccc(Nc2ccc3cc(Cl)ccc3n2)cc1]
128
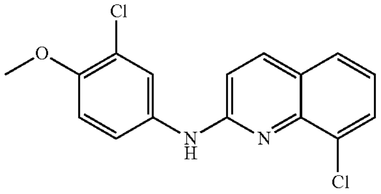 [SMILES: COc1ccc(Nc2ccc3cccc(Cl)c3n2)cc1Cl]
129
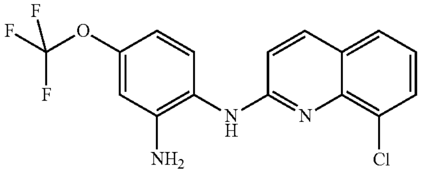 [SMILES: Nc1cc(OC(F)(F)F)ccc1Nc1ccc2cccc(Cl)c2n1]
130
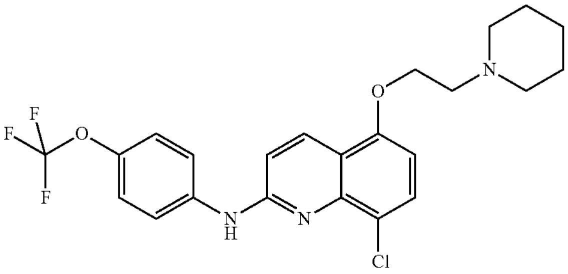 [SMILES: FC(F)(F)Oc1ccc(Nc2ccc3c(OCCN4CCCCC4)ccc(Cl)c3n2)cc1]
131
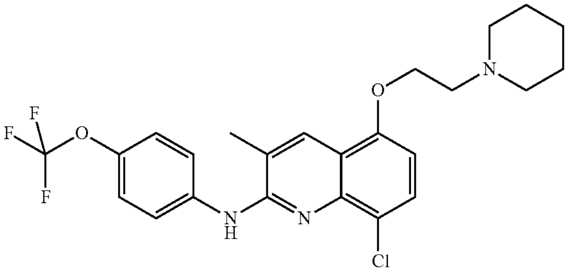 [SMILES: Cc1cc2c(OCCN3CCCCC3)ccc(Cl)c2nc1Nc1ccc(OC(F)(F)F)cc1]
132
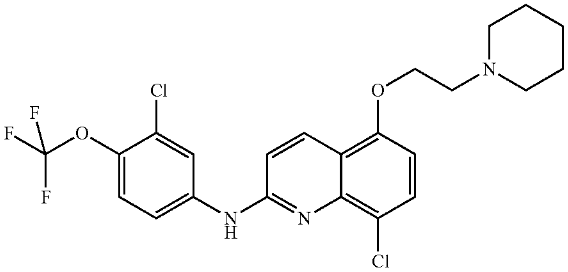 [SMILES: FC(F)(F)Oc1ccc(Nc2ccc3c(OCCN4CCCCC4)ccc(Cl)c3n2)cc1Cl]

TABLE 2-continued
(compounds of formula (Ib) as defined above)
133
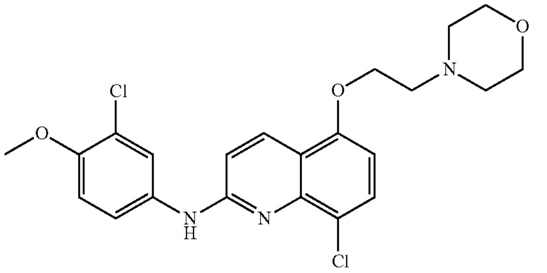 [SMILES: COc1ccc(Nc2ccc3c(OCCN4CCOCC4)ccc(Cl)c3n2)cc1Cl]
134
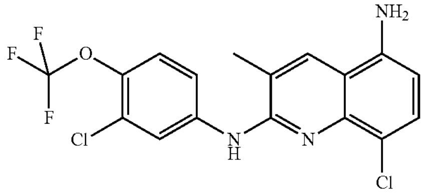
135
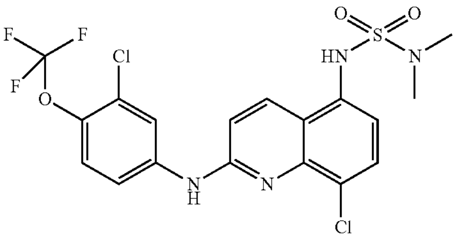 [SMILES: CN(C)S(=O)(=O)Nc1ccc(Cl)c2nc(Nc3ccc(OC(F)(F)F)c(Cl)c3)ccc12]
136
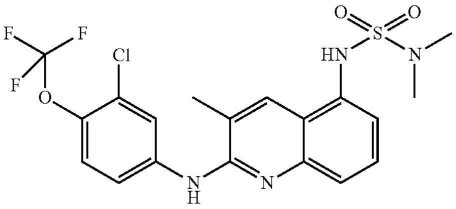 [SMILES: Cc1cc2c(NS(=O)(=O)N(C)C)cccc2nc1Nc1ccc(OC(F)(F)F)c(Cl)c1]
137
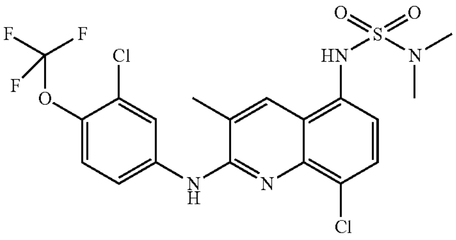 [SMILES: Cc1cc2c(NS(=O)(=O)N(C)C)ccc(Cl)c2nc1Nc1ccc(OC(F)(F)F)c(Cl)c1]
138
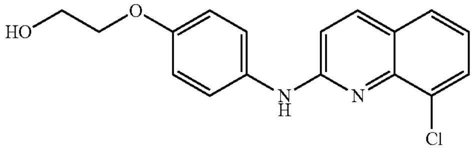 [SMILES: OCCOc1ccc(Nc2ccc3cccc(Cl)c3n2)cc1]
139
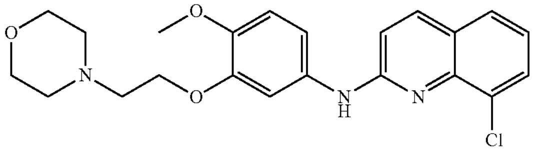 [SMILES: COc1ccc(Nc2ccc3cccc(Cl)c3n2)cc1OCCN1CCOCC1]

TABLE 2-continued
(compounds of formula (Ib) as defined above)
140
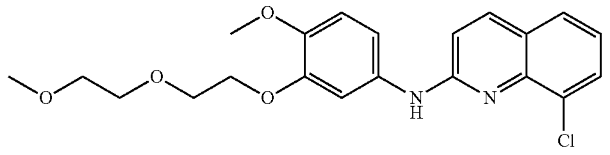 [SMILES: COCCOCCOc1cc(Nc2ccc3cccc(Cl)c3n2)ccc1OC]
141
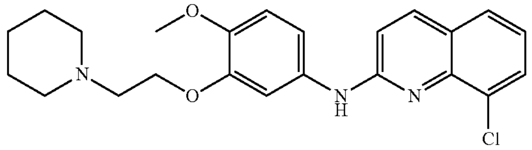 [SMILES: COc1ccc(Nc2ccc3cccc(Cl)c3n2)cc1OCCN1CCCCC1]
142
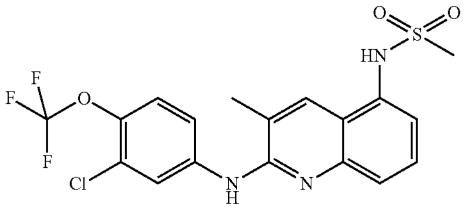 [SMILES: Cc1cc2c(NS(C)(=O)=O)cccc2nc1Nc1ccc(OC(F)(F)F)c(Cl)c1]
143
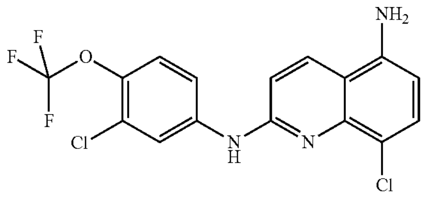 [SMILES: Nc1ccc(Cl)c2nc(Nc3ccc(OC(F)(F)F)c(Cl)c3)ccc12]
144
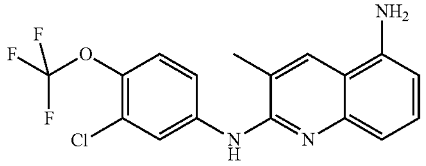 [SMILES: Cc1cc2c(N)cccc2nc1Nc1ccc(OC(F)(F)F)c(Cl)c1]
145
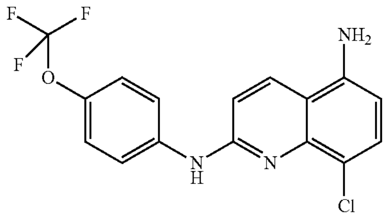 [SMILES: Nc1ccc(Cl)c2nc(Nc3ccc(OC(F)(F)F)cc3)ccc12]
146
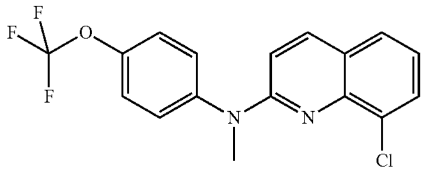
147
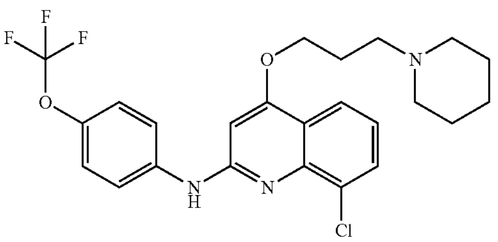 [SMILES: FC(F)(F)Oc1ccc(Nc2cc(OCCCN3CCCCC3)c3cccc(Cl)c3n2)cc1]

TABLE 2-continued
(compounds of formula (Ib) as defined above)
148
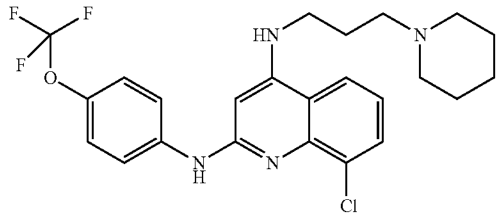 [SMILES: FC(F)(F)Oc1ccc(Nc2cc(NCCCN3CCCCC3)c3cccc(Cl)c3n2)cc1]
149
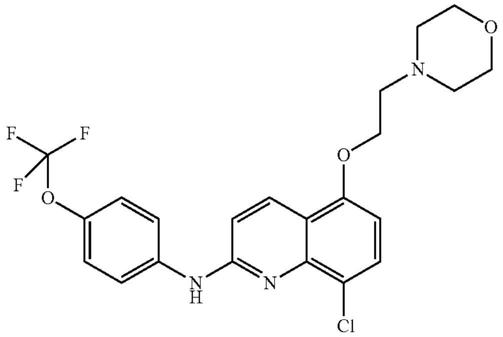 [SMILES: FC(F)(F)Oc1ccc(Nc2ccc3c(OCCN4CCOCC4)ccc(Cl)c3n2)cc1]
150
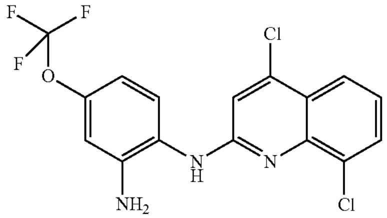 [SMILES: Nc1cc(OC(F)(F)F)ccc1Nc1cc(Cl)c2cccc(Cl)c2n1]
151
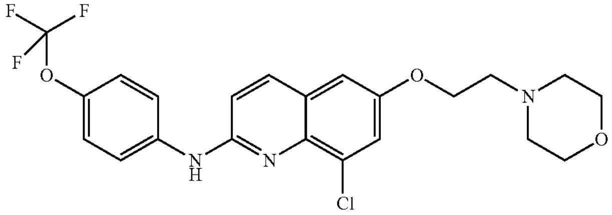 [SMILES: FC(F)(F)Oc1ccc(Nc2ccc3cc(OCCN4CCOCC4)cc(Cl)c3n2)cc1]
152
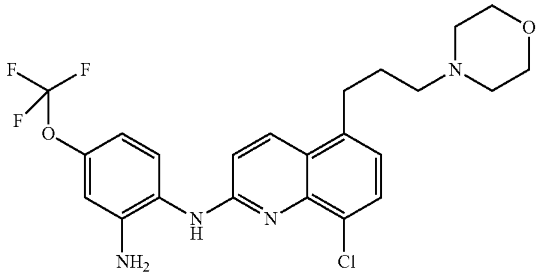 [SMILES: Nc1cc(OC(F)(F)F)ccc1Nc1ccc2c(CCCN3CCOCC3)ccc(Cl)c2n1]

TABLE 2-continued
| (compounds of formula (Ib) as defined above) | |
|---|---|
| 153 | 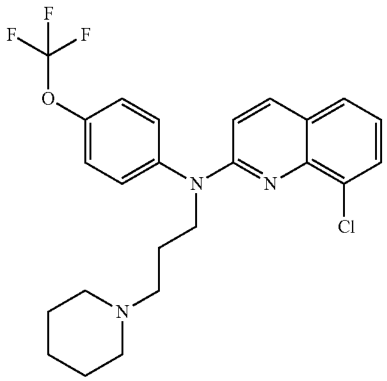 [SMILES: FC(F)(F)Oc1ccc(N(CCCN2CCCCC2)c2ccc3cccc(Cl)c3n2)cc1] |
| 154 | 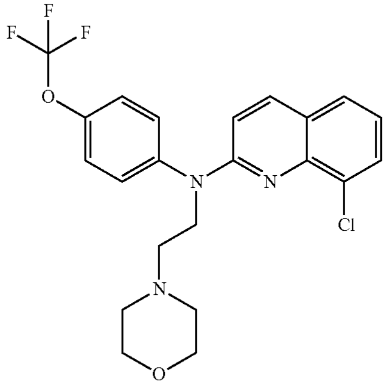 [SMILES: FC(F)(F)Oc1ccc(N(CCN2CCOCC2)c2ccc3cccc(Cl)c3n2)cc1] |
| 155 | 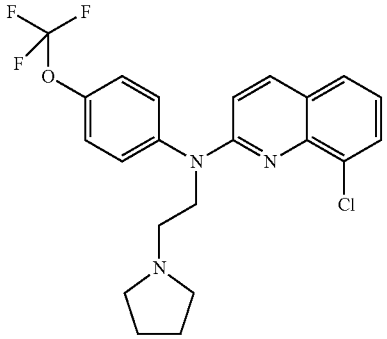 [SMILES: FC(F)(F)Oc1ccc(N(CCN2CCCC2)c2ccc3cccc(Cl)c3n2)cc1] |
| 156 | 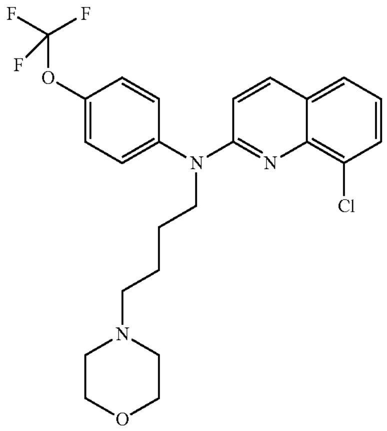 [SMILES: FC(F)(F)Oc1ccc(N(CCCCN2CCOCC2)c2ccc3cccc(Cl)c3n2)cc1] |

TABLE 2-continued
| (compounds of formula (Ib) as defined above) | |
|---|---|
| 157 | 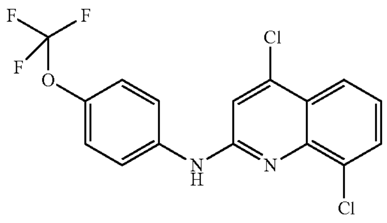 [SMILES: FC(F)(F)Oc1ccc(Nc2cc(Cl)c3cccc(Cl)c3n2)cc1] |
| 158 | 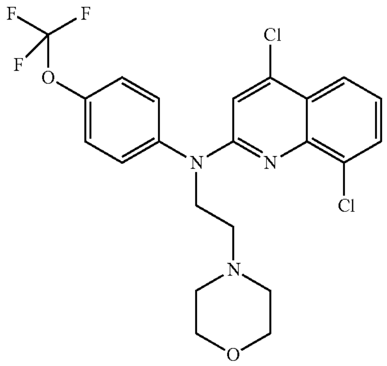 [SMILES: FC(F)(F)Oc1ccc(N(CCN2CCOCC2)c2cc(Cl)c3cccc(Cl)c3n2)cc1] |
| 159 | 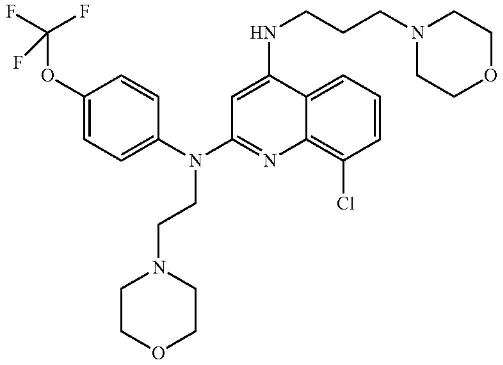 [SMILES: FC(F)(F)Oc1ccc(N(CCN2CCOCC2)c2cc(NCCCN3CCOCC3)c3cccc(Cl)c3n2)cc1] |
| 160 | 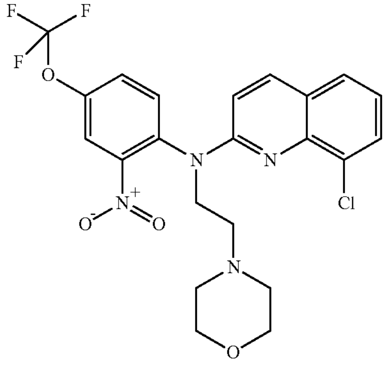 |

TABLE 2-continued
| (compounds of formula (Ib) as defined above) | |
|---|---|
| 161 | 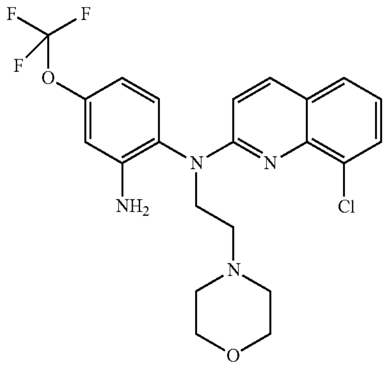 [SMILES: Nc1cc(OC(F)(F)F)ccc1N(CCN1CCOCC1)c1ccc2cccc(Cl)c2n1] |
| 162 | 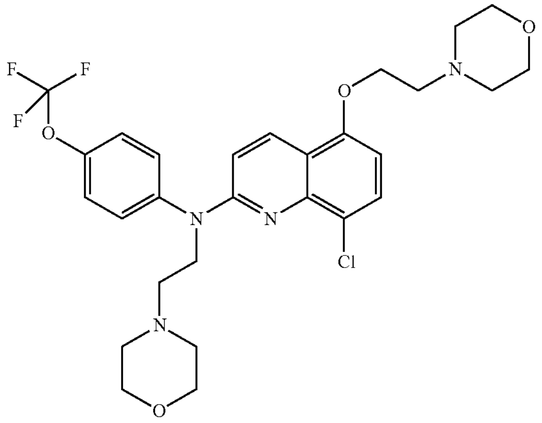 [SMILES: FC(F)(F)Oc1ccc(N(CCN2CCOCC2)c2ccc3c(OCCN4CCOCC4)ccc(Cl)c3n2)cc1] |
| 163 | 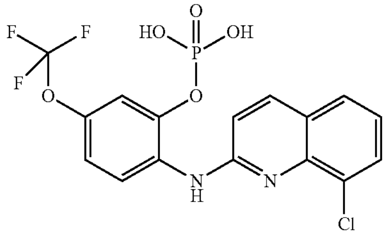 [SMILES: O=P(O)(O)Oc1cc(OC(F)(F)F)ccc1Nc1ccc2cccc(Cl)c2n1] |
| 164 | 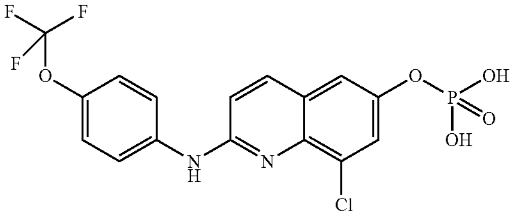 [SMILES: O=P(O)(O)Oc1cc(Cl)c2nc(Nc3ccc(OC(F)(F)F)cc3)ccc2c1] |
or a pharmaceutically acceptable salt thereof.

In some embodiments, the present invention provides a method for treating a viral infection, or an inflammatory disease, disorder or condition, or a cancer, comprising administering to a patient in need thereof a compound selected from Table 3:

TABLE 3

| (compounds of formula (I) other that compounds (Ia) and (Ib)) | |
|---|---|
| 165 | 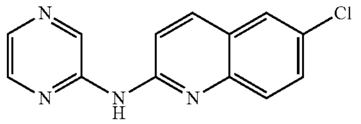 [SMILES: Clc1ccc2nc(Nc3cnccn3)ccc2c1] |
| 166 | 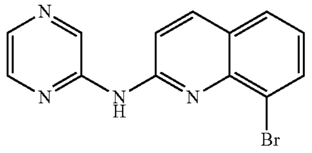 [SMILES: Brc1cccc2ccc(Nc3cnccn3)nc12] |
| 167 | 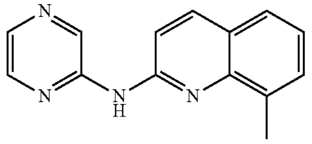 [SMILES: Cc1cccc2ccc(Nc3cnccn3)nc12] |
| 168 | 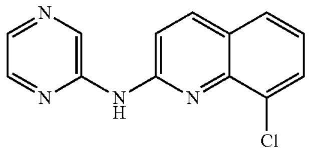 [SMILES: Clc1cccc2ccc(Nc3cnccn3)nc12] |
| 169 | 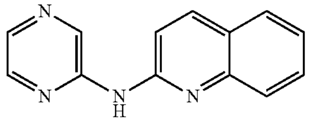 [SMILES: c1ccc2nc(Nc3cnccn3)ccc2c1] |
| 170 | 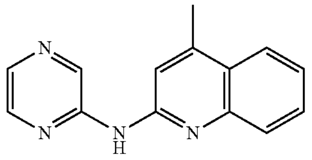 [SMILES: Cc1cc(Nc2cnccn2)nc2ccccc12] |
| 171 | 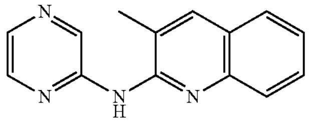 [SMILES: Cc1cc2ccccc2nc1Nc1cnccn1] |
| 172 | 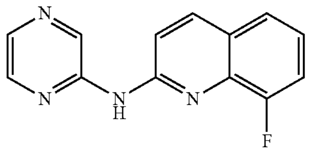 [SMILES: Fc1cccc2ccc(Nc3cnccn3)nc12] |
| 173 | 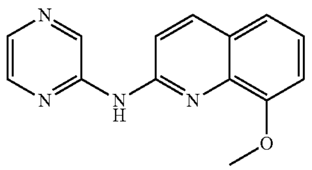 [SMILES: COc1cccc2ccc(Nc3cnccn3)nc12] |

TABLE 3-continued

| (compounds of formula (I) other that compounds (Ia) and (Ib)) | |
|---|---|
| 174 | 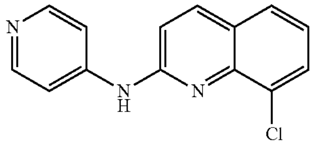 [SMILES: Clc1cccc2ccc(Nc3ccncc3)nc12] |
| 175 | 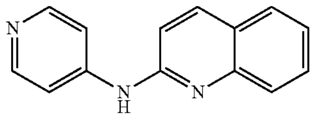 [SMILES: c1ccc2nc(Nc3ccncc3)ccc2c1] |
| 176 | 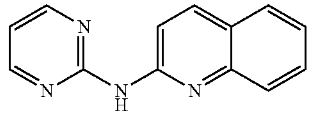 [SMILES: c1cnc(Nc2ccc3ccccc3n2)nc1] |
| 177 | 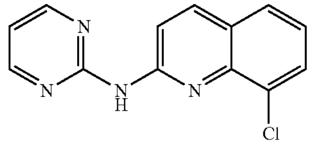 [SMILES: Clc1cccc2ccc(Nc3ncccn3)nc12] |
| 178 | 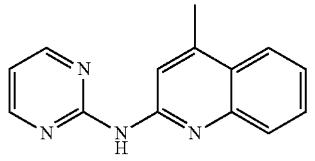 [SMILES: Cc1cc(Nc2ncccn2)nc2ccccc12] |
| 179 | 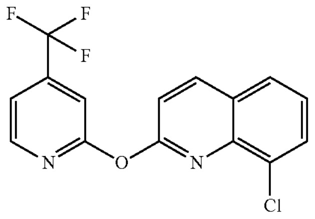 [SMILES: FC(F)(F)c1ccnc(Oc2ccc3cccc(Cl)c3n2)c1] |
| 180 | 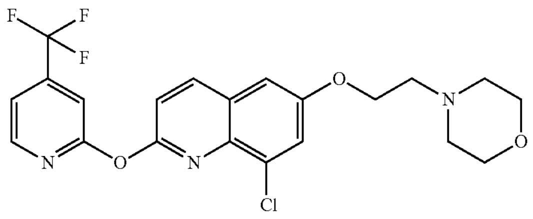 [SMILES: FC(F)(F)c1ccnc(Oc2ccc3cc(OCCN4CCOCC4)cc(Cl)c3n2)c1] |
| 181 | 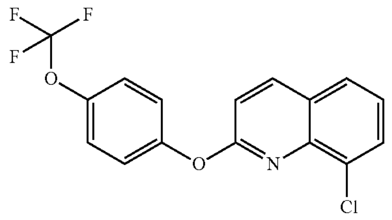 [SMILES: FC(F)(F)Oc1ccc(Oc2ccc3cccc(Cl)c3n2)cc1] |

TABLE 3-continued

| (compounds of formula (I) other that compounds (Ia) and (Ib)) | |
|---|---|
| 182 | 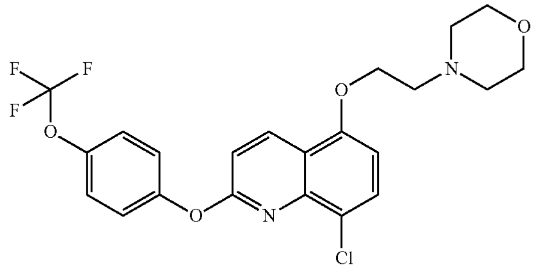 [SMILES: FC(F)(F)Oc1ccc(Oc2ccc3c(OCCN4CCOCC4)ccc(Cl)c3n2)cc1] |
| 183 | 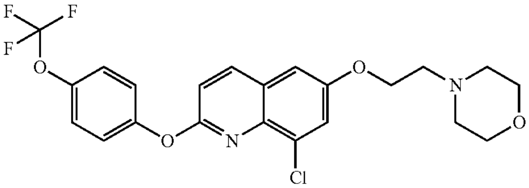 [SMILES: FC(F)(F)Oc1ccc(Oc2ccc3cc(OCCN4CCOCC4)cc(Cl)c3n2)cc1] |

or a pharmaceutically acceptable salt thereof.

In some embodiments, a compound described herein is in a salt form selected from sulfate, hydrobromide, citrate, trifluoroacetate, ascorbate, hydrochloride, tartrate, triflate, maleate, mesylate, formate, acetate, fumarate, and sulfonate. In some embodiments, a compound described herein is in salt form as alkylsufonate or arylsulfonate. In some embodiments, a compound described herein is in salt form as mesylate, triflate, edisylate, besylate and tosylate.

In one aspect, the present invention provides a method for treating a viral infection, or an inflammatory disease, disorder or condition, or a cancer, comprising administering to a patient in need thereof a metabolite of a compound described herein. In some embodiments, a metabolite of a compound described herein is a N-glucuronide metabolite.

In some embodiments, the present invention provides a method for treating a viral infection, or an inflammatory disease, disorder or condition, or a cancer, comprising administering to a patient in need thereof a compound of formula (IV):

(IV)

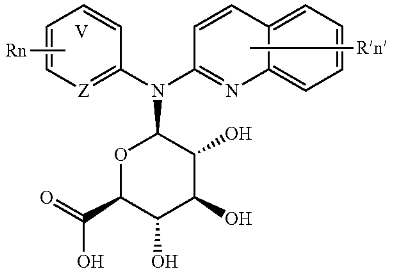

or a pharmaceutically acceptable salt thereof, wherein each of variables V, Z, R, R', n, and n' is as defined above and described in embodiments herein, both singly or in combination.

In some embodiments, the present invention provides a method for treating a viral infection, or an inflammatory disease, disorder or condition, or a cancer, comprising administering to a patient in need thereof a compound of formula (IVa):

(IVa)

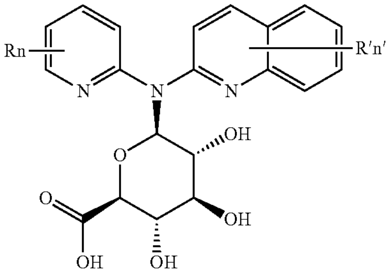

or a pharmaceutically acceptable salt thereof, wherein each of variables R, R', n, and n' is independently as defined above and described in embodiments herein, both singly and in combination.

In some embodiments, the present invention provides a method for treating a viral infection, or an inflammatory disease, disorder or condition, or a cancer, comprising administering to a patient in need thereof a compound of formula (IVb):

(IVb)

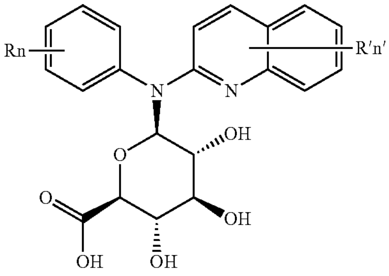

or a pharmaceutically acceptable salt thereof, wherein each of variables R, R', n, and n' is independently as defined above and described in embodiments herein, both singly and in combination.

In some embodiments, the present invention provides a method for treating a viral infection, or an inflammatory disease, disorder or condition, or a cancer, comprising administering to a patient in need thereof a compound of formula (IVc):

(IVc)

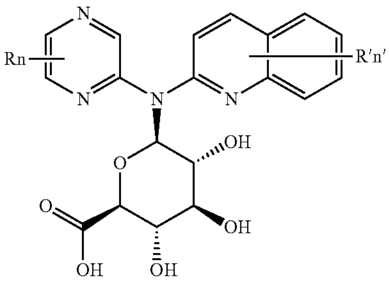

or a pharmaceutically acceptable salt thereof, wherein each of variables R, R', n, and n' is independently as defined above and described in embodiments herein, both singly and in combination.

In some embodiments, the present invention provides a method for treating a viral infection, or an inflammatory disease, disorder or condition, or a cancer, comprising administering to a patient in need thereof a compound of formula (IVb'):

(IVb')

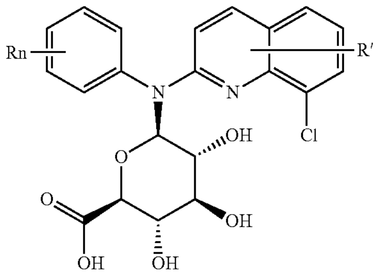

or a pharmaceutically acceptable salt thereof, wherein each of variables R, R', and n is independently as defined above and described in embodiments herein, both singly and in combination.

In some embodiments, the present invention provides a method for treating a viral infection, or an inflammatory disease, disorder or condition, or a cancer, comprising administering to a patient in need thereof a compound of formula (IVd):

(IVd)

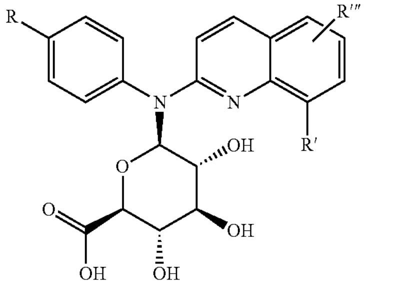

or a pharmaceutically acceptable salt thereof, wherein each of variables R, R', R''' is independently as defined above and described in embodiments herein, both singly and in combination.

In some embodiments, the present invention provides a method for treating a viral infection, or an inflammatory disease, disorder or condition, or a cancer, comprising administering to a patient in need thereof a compound of formula:

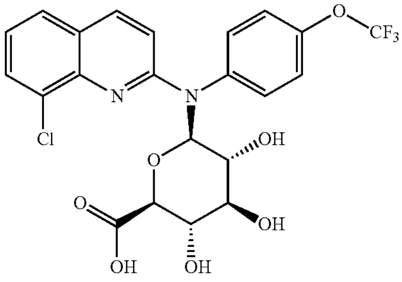 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

or a pharmaceutically acceptable salt thereof.

In some embodiments, a method of the present invention comprises measuring a level of a compound or a pharmaceutically acceptable salt thereof as described herein, or a metabolite thereof, in a patient. In some embodiments, a level of a compound or a pharmaceutically acceptable salt thereof as described herein, or a metabolite thereof, is measured in a patient's biological sample. In some embodiments, a patient's biological sample is a blood, plasma, and/or serum sample. In some embodiments, a method of the present invention comprises measuring a level of a compound of formula (I), (Ia), (Ib), (Ib'), (Ic), and (Id), or pharmaceutically acceptable salts thereof, in a patient. In some embodiments, a method of the present invention comprises measuring a level of a compound of formulas (IV), (IVa), (IVb), (IVb') (IV), and (IVd), or pharmaceutically acceptable salts thereof, in a patient. In some embodiments, a method of the present invention comprises measuring a total level of compounds of formulas (I) and (IV), or pharmaceutically acceptable salts thereof, in a patient. In some embodiments, a method of the present invention comprises measuring a total level of compounds of formulas (I) and (IV), or pharmaceutically acceptable salts thereof, in a patient. In some embodiments, a method of the present invention comprises measuring a total level of compounds of formulas (Ia) and (IVa), or pharmaceutically acceptable salts thereof, in a patient. In some embodiments, a method of the present invention comprises measuring a total level of compounds of formulas (Ib) and (IVb), or pharmaceutically acceptable salts thereof, in a patient. In some embodiments, a method of the present invention comprises measuring a total level of compounds of formulas (Ib') and (IVb'), or pharmaceutically acceptable salts thereof, in a patient. In some embodiments, a method of the present invention comprises measuring a total level of compounds of formulas (Ic) and (IVc), or pharmaceutically acceptable salts thereof, in a patient. In some embodiments, a method of the present invention comprises measuring a total level of compounds of formulas (Id) and (IVd), or pharmaceutically acceptable salts thereof, in a patient.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an active metabolite or residue thereof.

A "biological sample" suitable for the present invention can be a biological fluid, such as a blood, a plasma, or a serum, a saliva, an interstitial fluid, or an urine sample; a cell sample, such as a cell culture, a cell line, or a PBMC sample, a tissue biopsy, such as an oral tissue, a gastrointestinal tissue, a skin, an oral mucosa sample, or a plurality of samples from a clinical trial. A biological sample can be a crude sample, or can be purified to various degrees prior to storage, processing, or measurement. In some embodiments, a biological sample is selected from the group consisting of a biological tissue sample, a whole blood sample, a swab sample, a plasma sample, a serum sample, a saliva sample, a vaginal fluid sample, a sperm sample, a pharyngeal fluid sample, a bronchial fluid sample, a fecal fluid sample, a cerebrospinal fluid sample, a lacrymal fluid sample and a tissue culture supernatant sample.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water. Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for treatment of a viral infection, or an inflammatory disease, disorder or condition, or a cancer.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, the present invention provides a method for treating an inflammatory disease, disorder or condition, or a cancer, comprising administering to a patient in need thereof a compound or composition as described herein.

The compounds and compositions, according to the method of the present invention, may be administered using any amount and any route of administration effective for treating or lessening the severity of a disease or disorder, or one or more symptoms thereof, as described herein. The exact amount required will vary from subject to subject, depending on the species, age, and general condition of the subject, the severity of the disease or condition, the particular agent, its mode of administration, and the like. Compounds as described herein are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds as described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Inflammatory Diseases, Disorders or Conditions

Compounds as described herein are useful in the treatment of inflammatory or obstructive airways diseases, resulting, for example, in reduction of tissue damage, airways inflammation, bronchial hyperreactivity, remodeling or disease progression. In some embodiments, an inflammatory disease, disorder, or condition is inflammatory or obstructive airways diseases including, but not limited to, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Compounds as described herein are useful in the treatment of heteroimmune diseases. In some embodiments, an inflammatory disease, disorder, or condition is heteroimmune diseases including, but not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to "morning dipping". "Morning dipping" is a recognized asthmatic syndrome, common to a substantial percentage of asthmatics and characterised by asthma attack, e.g. between the hours of about 4 to 6 am, i.e. at a time normally substantially distant form any previously administered symptomatic asthma therapy.

In some embodiments, an inflammatory disease, disorder, or condition is selected from acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. In some embodiments, an inflammatory disease, disorder, or condition is bronchitis, wherein the bronchitis is of whatever type or genesis including, but not limited to, acute, arachidic, catarrhal, croupus, chronic or phthinoid bronchitis. In some embodiments, an inflammatory disease, disorder, or condition is pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

In some embodiments, an inflammatory disease, disorder, or condition is an eosinophil related disorder, e.g. eosinophilia. In some embodiments, an eosinophil related disorder is an eosinophil related disorder of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds as described herein are also useful in the treatment of inflammatory or allergic conditions of the skin. In some embodiments, an inflammatory or allergic condition of the skin is selected from psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

In some embodiments, an inflammatory disease, disorder, or condition is a disease or condition having an inflammatory component, for example, diseases and conditions of the eye such as ocular allergy, conjunctivitis, keratoconjunctivitis sicca, uveitis and vernal conjunctivitis, diseases and conditions affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca, uveitis, and vernal keratoconjunctivitis, interstitial lung fibrosis, psoriatic arthritis, systemic juvenile idiopathic arthritis, cryopyrin-associated periodic syndrome, Muckle-Wells syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, intestinal failure, hyperchlolesterolemia, heart disease, chronic heart failure, mesothelioma, anhidrotic ecodermal dysplasia, Behcet's disease, incontinentia pigmenti, Paget's disease, acute or chronic pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments, an inflammatory disease, disorder, or condition is acute or chronic graft rejection in kidney, liver, heart, pulmonary transplantation, or graft versus-host disease in bone marrow graft.

In some embodiments, an inflammatory disease, disorder, or condition is an inflammatory disease, disorder, or condition of the skin. In some embodiments, an inflammatory disease, disorder, or condition of the skin is selected from contact dermatitis, atopic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, and other inflammatory or allergic conditions of the skin.

In some embodiments, an inflammatory disease, disorder, or condition is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin Associated Periodic Syndrome (CAPS), Muckle-Wells syndrome, and osteoarthritis.

In some embodiments, an inflammatory disease, disorder, or condition is a TH17 mediated disease. In some embodiments, a TH17 mediated disease is selected from Systemic lupus erythematosus, Multiple sclerosis, and inflammatory bowel disease (including Crohn's disease or ulcerative colitis).

In some embodiments, an inflammatory disease, disorder, or condition is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

In some embodiments, an inflammatory disease, disorder, or condition is associated with transplantation. In some embodiments, an inflammatory disease, disorder, or condition is associated with organ transplantation, organ transplant rejection, and/or graft versus host disease.

In some embodiments, an inflammatory disease, disorder, or condition is an autoimmune disorder. In some embodiments an autoimmune disorder is type 1 diabetes, systemic lupus erythematosus, multiple sclerosis, psoriasis, Behçet's disease, POEMS syndrome, Crohn's disease, ulcerative colitis, ankylosing spondylitis, axial spondyloarthritis, primary biliary cirrhosis, autoimmune hepatitis, or inflammatory bowel disease.

In some embodiments, an inflammatory disease, disorder, or condition is an inflammatory disorder. In some embodiments, an inflammatory disorder is rheumatoid arthritis, asthma, chronic obstructive pulmonary disease, psoriasis, hepatomegaly, Crohn's disease, ulcerative colitis, ankylosing spondylitis, axial spondyloarthritis, primary biliary cirrhosis, polymyalgia rheumatica, giant cell arteritis, or inflammatory bowel disease.

In some embodiments, the present invention provides a method for treating an inflammatory disease, disorder, or condition in the pancreas. In some embodiments, an inflammatory disease, disorder, or condition in the pancreas is selected from diabetes type-1, diabetes type-2, acute and chronic pancreatitis.

In some embodiments, the present invention provides a method for treating an inflammatory disease, disorder, or condition in the kidney. In some embodiments, an inflammatory disease, disorder, or condition in the kidney is selected from glomerulosclerosis, glomerulonephritis, nephritis, acute kidney injury, Berger's disease, Goodpasture's syndrome, Wegener's granulomatosis, and kidney transplant acute or chronic rejection.

In some embodiments, the present invention provides a method for treating an inflammatory disease, disorder, or condition in the liver. In some embodiments, an inflammatory disease, disorder, or condition in the liver is selected from nonalcoholic steatohepatitis (NASH), non-alcoholic fatty liver disease (NAFLD), cholestatic liver disease, sclerosing cholangitis, and liver transplant acute or chronic rejection.

In some embodiments, the present invention provides a method for treating an inflammatory disease, disorder, or condition in the lung. In some embodiments, an inflammatory disease, disorder, or condition in the lung is selected from chronic obstructive pulmonary disease (COPD), asthma, pulmonary fibrosis, pulmonary hypertension, sarcoidosis, and lung transplant acute or chronic rejection.

In some embodiments, the present invention provides a method for treating an inflammatory disease, disorder, or condition in the skin. In some embodiments, an inflammatory disease, disorder, or condition in the skin is selected from contact dermatitits, atopic dermatitis, psoriasis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, acnea, keloid scar, and other inflammatory or allergic conditions of the skin.

In some embodiments, the present invention provides a method for treating an inflammatory disease, disorder, or condition in the vessel/blood. In some embodiments, an inflammatory disease, disorder, or condition in the vessel/blood is selected from Behcet's disease, vasculitis, sepsis, tumor angiogenesis, atherosclerosis, proliferative vascular disease, and restenosis.

In some embodiments, the present invention provides a method for treating an inflammatory disease, disorder, or condition in the eye. In some embodiments, an inflammatory disease, disorder, or condition in the eye is selected from conjunctivitis, scleritis, episcleritis, panuveitis, choroiditis, chorioretinitis, neuroretinitis, uveitis, orbital inflammatory disease, and optical neuritis.

In some embodiments, the present invention provides a method for treating an inflammatory disease, disorder, or condition in the central or peripheral nervous system. In some embodiments, an inflammatory disease, disorder, or condition in the central or peripheral nervous system is selected from non-viral and viral encephalitis and meningitis, depression, neuropathic pain, including chronic pain, traumatic brain injury, including stroke. Alzheimer disease, Parkinson disease, Myelitis, Charcot-Marie-Tooth disease type 1 (including CMT1A and CMT1B), Multiple sclerosis, Amyotrophic lateral sclerosis (ALS), Creutzfeldt-Jakob disease, demyelinating polyneuropathy and peripheral neuropathy.

In some embodiments, the present invention provides a method for treating an autoimmune disease, disorder, or condition. In some embodiments, an autoimmune disease, disorder, or condition is selected from Lupus, including in the skin and kidney, Guillain-Barre syndrome, Myasthenia gravis, Hashimoto's thyroiditis, idiopathic purpura, aplastic anemia, Graves disease, and Myocarditis.

In some embodiments, the present invention provides a method for treating an inflammatory disease, disorder, or condition in the intestine. In some embodiments, an inflammatory disease, disorder, or condition in the intestine is selected from intestinal failure, Ulcerative colitis, and Crohn's disease.

In some embodiments, the present invention provides a method for treating an inflammatory disease, disorder, or condition in the reproductive system. In some embodiments, an inflammatory disease, disorder, or condition in the reproductive system is selected from endometriosis, uterine fibroma, prostate dysplasia or growth, and cervix dysplasia.

In some embodiments, the present invention provides a method for treating an inflammatory disease, disorder, or condition in the bone and/or joints. In some embodiments, an inflammatory disease, disorder, or condition in the bone and/or joints is selected from juvenile idiopathic arthritis, psoriatic arthritis, periodontitis, and hand, foot, ankle, knee, hip, shoulder, elbow or spine arthritis and/or demineralization.

In some embodiments, the present invention provides a method for treating an AIDS-related or AIDS-comorbid inflammatory disorder or condition.

Combination Therapies of Inflammatory Diseases, Disorders or Conditions

Depending upon the particular condition, or disease, to be treated, additional therapeutic agents, which are normally administered to treat that condition, may be administered in combination with compounds and compositions as described herein. As used herein, additional therapeutic agents that are normally administered to treat a particular disease, or condition, are known as "appropriate for the disease, or condition, being treated."

In certain embodiments, the present invention provides a method for treating an inflammatory disease, disorder, or condition, comprising administering to a patient in need thereof a compound or composition as described herein in combination with another therapeutic agent.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The combination may result in an additive, or in a synergistic effect, where lower doses of one or both of the compound may be used to obtain a similar efficacy, or where the same doses may result in a significantly improved efficacy.

In some embodiments, the present invention provides a composition comprising a compound as described herein and one or more additional therapeutic agents. The therapeutic agent may be administered together with a compound as described herein, or may be administered prior to or following administration of a compound as described herein. Suitable therapeutic agents are described in further detail below. In certain embodiments, a compound as described herein may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In certain embodiments, a compound as described herein may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In some embodiments, the present invention provides a method of treating an inflammatory disease, disorder or condition by administering to a patient in need thereof a compound as described herein and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®, Neoral®), tacrolimus, sirolimus, mycophenolate, leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), anti-T cell antibodies such as Thymoglobulin, IV Immunoglobulins (IVIg), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®%), inhaled corticosteroids such as beclomethasone dipropionate (Beclovent®, Qvar®), and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), anti-IL36 agents such as BI655130, Dihydroorotate dehydrogenase inhibitors such as IMU-838, anti-OX40 agents such as KHK-4083, microbiome agents such as RBX2660, SER-287, Narrow spectrum kinase inhibitors such as TOP-1288, anti-CD40 agents such as BI-655064 and FFP-104, guanylate cyclase agonists such as dolcanatide, sphingosine kinase inhibitors such as opaganib, anti-IL-12/IL-23 agents such as AK-101, Ubiquitin protein ligase complex inhibitors such as BBT-401, sphingosine receptors modulators such as BMS-986166, P38MAPK/PDE4 inhibitors such as CBS-3595, CCR9 antagonists such as CCX-507, FimH antagonists such as EB-8018, HIF-PH inhibitors such as FG-6874, HIF-1$\alpha$ stabilizer such as GB-004. MAP3K8 protein inhibitors such as GS-4875. LAG-3 antibodies such as GSK-2831781, RIP2 kinase inhibitors such as GSK-2983559, Farnesoid X receptor agonist such as MET-409, CCK2 antagonists such as PNB-001, IL-23 Receptor antagonists such as PTG-200, Purinergic P2X7 receptor antagonists such as SGM-1019, PDE4 inhibitors such as Apremilast, ICAM-1 inhibitors such as alicaforsen sodium, Anti-IL23 agents such as guselkumab, brazikumab and mirikizumab, ant-IL-15 agents such as AMG-714, TYK-2 inhibitors such as BMS-986165, NK Cells activators such as CNDO-201, RIP-1 kinase inhibitors such as GSK-2982772, anti-NKGD2 agents such as JNJ-4500. CXCL-10 antibodies such as JT-02, IL-22 receptor agonists such as RG-7880. GATA-3 antagonists such as SB-012 and Colony-stimulating factor-1 receptor inhibitors such as edicotinib or any combination(s) thereof.

In another embodiment, the present invention provides a method of treating gout comprising administering to a patient in need thereof a compound as described herein and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a compound as described herein and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound as described herein and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a compound as described herein and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound as described herein and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound as described herein and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®) anticholinergic agents such as ipratropium bromide (Atrovent®) and tiotropium (Spiriva®), inhaled corticosteroids such as prednisone, prednisolone, beclomethasone dipropionate (Beclovent®3, Qvar®), and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound as described herein and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®.

In some embodiments, the present invention provides a method of treating HIV comprising administering to a patient in need thereof a compound as described herein and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In some embodiments, the present invention provides a method of treating organ transplant rejection or graft vs. host disease comprising administering to a patient in need thereof a compound as described herein and one or more additional therapeutic agents selected from a steroid, cyclosporin, FK506, rapamycin, a hedgehog signaling inhibitor, a BTK inhibitor, a JAK/pan-JAK inhibitor, a TYK2 inhibitor, a PI3K inhibitor, and a SYK inhibitor.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zatirlukast; PDE4 inhibitors such cilomilast (Ariflo® GlaxoSmithKline), Roflumilast (Byk Gulden). V-11294A (Napp), BAY19-8004 (Bayer), SCH-351591 (Schering-Plough), Arofylline (Almirall Prodesfarma), PD189659/PD168787 (ParkeDavis), AWD-12-281 (Asta Medica), CDC-801 (Celgene), SeICID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined." and related terms refer to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both a compound as described herein and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Cancers

Cancer includes, in one embodiment, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, the cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, the cancer is acoustic neuroma, astrocytoma (e.g. Grade I—Pilocytic Astrocytoma, Grade II—Low-grade Astrocytoma, Grade III—Anaplastic Astrocytoma, or Grade IV Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (JPA), medulloblastoma, optic nerve glioma, pineal tumor, primitive neuroectodermal tumors (PNET), or rhabdoid tumor. In some embodiments, the patient is an adult human. In some embodiments, the patient is a child or pediatric patient.

Cancer includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the cancer is selected from hepatocellular carcinoma, ovarian cancer, ovarian epithelial cancer, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical adenoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from hepatocellular carcinoma (HCC), hepatoblastoma, colon cancer, rectal cancer, ovarian cancer, ovarian epithelial cancer, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical adenoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, a cancer is a solid tumor, such as a sarcoma, carcinoma, or lymphoma. Solid tumors generally comprise an abnormal mass of tissue that typically does not include cysts or liquid areas. In some embodiments, the cancer is selected from renal cell carcinoma, or kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN);

salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from renal cell carcinoma, hepatocellular carcinoma (HCC), hepatoblastoma, colorectal carcinoma, colorectal cancer, colon cancer, rectal cancer, anal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, chondrosarcoma, anaplastic thyroid cancer, adrenocortical carcinoma, pancreatic cancer, pancreatic ductal carcinoma, pancreatic adenocarcinoma, glioma, brain cancer, neurofibromatosis-1 associated malignant peripheral nerve sheath tumors (MPNST), Waldenstrom's macroglobulinemia, or medulloblastoma.

In some embodiments, the cancer is selected from hepatocellular carcinoma (HCC), hepatoblastoma, colon cancer, rectal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical carcinoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

In some embodiments, a cancer is a viral-associated cancer, including human immunodeficiency virus (HIV) associated solid tumors, human papilloma virus (HPV)-16 positive incurable solid tumors, and adult T-cell leukemia, which is caused by human T-cell leukemia virus type 1 (HTLV-1) and is a highly aggressive form of CD4+ T-cell leukemia characterized by clonal integration of HTLV-1 in leukemic cells (See https://clinicaltrials.gov/ct2/show/study/NCT02631746); as well as virus-associated tumors in gastric cancer, nasopharyngeal carcinoma, cervical cancer, vaginal cancer, vulvar cancer, squamous cell carcinoma of the head and neck, and Merkel cell carcinoma. (See https://clinicaltrials.gov/ct2/show/study/NCT02488759; see also https://clinicaltrials.gov/ct2/show/study/NCT0240886; https://clinicaltrials.gov/ct2/show/NCT02426892)

In some embodiments, a cancer is melanoma cancer. In some embodiments, a cancer is breast cancer. In some embodiments, a cancer is lung cancer. In some embodiments, a cancer is small cell lung cancer (SCLC). In some embodiments, a cancer is non-small cell lung cancer (NSCLC).

In some embodiments, a cancer is treated by arresting further growth of the tumor. In some embodiments, a cancer is treated by reducing the size (e.g., volume or mass) of the tumor by at least 5%, 10%, 25%, 50%, 75%, 90% or 99% relative to the size of the tumor prior to treatment. In some embodiments, a cancer is treated by reducing the quantity of the tumor in the patient by at least 5%, 10%, 25%, 50%, 75%, 90% or 99% relative to the quantity of the tumor prior to treatment.

Combination Therapies of Cancers

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

One or more other therapeutic agent may be administered separately from a compound or composition of the invention, as part of a multiple dosage regimen. Alternatively, one or more other therapeutic agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and a compound or composition of the invention are administered as a multiple dosage regimen within greater than 24 hours apart.

As used herein, the term "combination," "combined," and related terms refers to the simultaneous or sequential administration of therapeutic agents in accordance with this invention. For example, a compound of the present invention may be administered with one or more other therapeutic agent simultaneously or sequentially in separate unit dosage forms or together in a single unit dosage form. Accordingly, the present invention provides a single unit dosage form comprising a compound of the current invention, one or more other therapeutic agent, and a pharmaceutically acceptable carrier, adjuvant, or vehicle.

The amount of a compound of the invention and one or more other therapeutic agent (in those compositions which comprise an additional therapeutic agent as described above) that may be combined with the carrier materials to produce a single dosage form will vary depending upon the host treated and the particular mode of administration. Preferably, a composition of the invention should be formulated so that a dosage of between 0.01-100 mg/kg body weight/day of a compound of the invention can be administered.

In those compositions which comprise one or more other therapeutic agent, the one or more other therapeutic agent and a compound of the invention may act synergistically. Therefore, the amount of the one or more other therapeutic agent in such compositions may be less than that required in a monotherapy utilizing only that therapeutic agent. In such compositions a dosage of between 0.01-1,000 μg/kg body weight/day of the one or more other therapeutic agent can be administered.

The amount of one or more other therapeutic agent present in the compositions of this invention may be no more than the amount that would normally be administered in a composition comprising that therapeutic agent as the only active agent. Preferably the amount of one or more other therapeutic agent in the presently disclosed compositions will range from about 50% to 100% of the amount normally present in a composition comprising that agent as the only therapeutically active agent. In some embodiments, one or more other therapeutic agent is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is approved for dosing per the FDA label insert.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by precoating the device with a pharmaceutically acceptable composition comprising a kinase inhibitor. Implantable devices coated with a compound of this invention are another embodiment of the present invention.

Exemplary Other Therapeutic Agents

In some embodiments, one or more other therapeutic agent is a Poly ADP ribose polymerase (PARP) inhibitor. In some embodiments, a PARP inhibitor is selected from olaparib (Lynparza®, AstraZeneca); rucaparib (Rubraca®, Clovis Oncology); niraparib (Zejula®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (Zolinza®, Merck); romidepsin (Istodax®, Celgene); panobinostat (Farydak®, Novartis); belinostat (Beleodaq®, Spectrum Pharmaceuticals); entinostat (SNDX-275, Syndax Pharmaceuticals) (NCT00866333); and chidamide (Epidaza®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (Ibrance®, Pfizer); ribociclib (Kisqali®, Novartis); abemaciclib (Ly2835219, Eli Lilly); and trilaciclib (GIT28, G1 Therapeutics).

In some embodiments, one or more other therapeutic agent is a phosphatidylinositol 3 kinase (PI3K) inhibitor. In some embodiments, a PI3K inhibitor is selected from idelalisib (Zydelig®, Gilead), alpelisib (BYL719, Novartis), taselisib (GDC-0032, Genentech/Roche); pictilisib (GDC-0941, Genentech/Roche); copanlisib (BAY806946. Bayer); duvelisib (formerly IPI-145, Infinity Pharmaceuticals); PQR309 (Piqur Therapeutics, Switzerland); and TGR1202 (formerly RP5230, TG Therapeutics).

In some embodiments, one or more other therapeutic agent is a platinum-based therapeutic, also referred to as platins. Platins cause cross-linking of DNA, such that they inhibit DNA repair and/or DNA synthesis, mostly in rapidly reproducing cells, such as cancer cells. In some embodiments, a platinum-based therapeutic is selected from cisplatin (Platinol®, Bristol-Myers Squibb); carboplatin (Paraplatin®, Bristol-Myers Squibb; also, Teva; Pfizer); oxaliplatin (Eloxitin® Sanofi-Aventis); nedaplatin (Aqupla®, Shionogi), picoplatin (Poniard Pharmaceuticals); and satraplatin (JM-216, Agennix).

In some embodiments, one or more other therapeutic agent is a taxane compound, which causes disruption of microtubules, which are essential for cell division. In some embodiments, a taxane compound is selected from paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), cabazitaxel (Jevtana®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®. Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, one or more other therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt), Novartis).

Other kinase inhibitors and VEGF-R antagonists that are in development and may be used in the present invention include tivozanib (Aveo Pharmaceuticals); vatalanib (Bayer/Novartis); lucitanib (Clovis Oncology); dovitinib (TK1258, Novartis); Chiauanib (Chipscreen Biosciences); CEP-11981 (Cephalon); linifanib (Abbott Laboratories); neratinib (HK1-272, Puma Biotechnology); radotinib (Supect®, IY5511, Il-Yang Pharmaceuticals. S. Korea); ruxolitinib (Jakafi®, Incyte Corporation); PTC299 (PTC Therapeutics); CP-547,632 (Pfizer); foretinib (Exelexis. GlaxoSmithKline); quizartinib (Daiichi Sankyo) and motesanib (Amgen/Takeda).

In some embodiments, one or more other therapeutic agent is an mTOR inhibitor, which inhibits cell proliferation, angiogenesis and glucose uptake. In some embodiments, an mTOR inhibitor is everolimus (Afinitor®, Novartis); temsirolimus (Torisel®, Pfizer); and sirolimus (Rapamune®, Pfizer).

In some embodiments, one or more other therapeutic agent is a proteasome inhibitor. Approved proteasome inhibitors useful in the present invention include bortezomib (Velcade®, Takeda); carfilzomib (Kyprolis®, Amgen); and ixazomib (Ninlaro®, Takeda).

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

In some embodiments, one or more other therapeutic agent is an aromatase inhibitor. In some embodiments, an aromatase inhibitor is selected from exemestane (Aromasin®, Pfizer); anastazole (Arimidex®, AstraZeneca) and letrozole (Femara®, Novartis).

In some embodiments, one or more other therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, one or more other therapeutic agent is a folic acid inhibitor. Approved folic acid inhibitors useful in the present invention include pemetrexed (Alimta®, Eli Lilly).

In some embodiments, one or more other therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, one or more other therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, one or more other therapeutic agent is a topoisomerase inhibitor. Approved topoisomerase inhibitors useful in the present invention include irinotecan (Onivyde®3, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, one or more other therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (Evista®, Eli Lilly).

In some embodiments, one or more other therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, one or more other therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFß). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1I/TGFß trap compound (NCT02699515); and (NCT02517398). M7824 is comprised of a fully human IgG1 antibody against PD-L1 fused to the extracellular domain of human TGF-beta receptor II, which functions as a TGFß "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE, gpNMB is a protein overexpressed by multiple tumor types associated with cancer cells' ability to metastasize.

In some embodiments, one or more other therapeutic agent is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, $AZd_6244$ from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered. e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed, under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xelodar™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; limofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases ($EGFR_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4. E2.5, E6.2. E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3K6, PI3Kp, PI3K-C2α, PI3K-C2β, PI3K-C2γ, Vps34, p 110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBT-05204, GSK-2126458, ZSTK-474, buparlisib, pictrelisib, PF-4691502, BYL-719, dactolisib, XL-147, XL-765, and idelalisib.

The term "Bel-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof see U.S. Pat. No. 7,390,799), NH-1 (Shenayng Pharmaceutical University), obatoclax (and analogs thereof, see WO2004106328), 5-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, cartilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to. Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., $4^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; $Zd_6474$; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-1-13, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-p. VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD 113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-IR antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase-(TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific $CD8^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+(Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15), rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams ET. AL., "Big opportunities for small molecules in immuno-oncology," Cancer Therapy 2015, Vol. 14, pages 603-622, the content of which is incorporated herein by reference in its entirety. In some embodiment, an immuno-oncology agent is selected from the examples described in Table 1 of Jerry L. Adams ET. AL. In some embodiments, an immuno-oncology agent is a small molecule targeting an immuno-oncoloby target selected from those listed in Table 2 of Jerry L. Adams ET. AL. In some embodiments, an immuno-oncology agent is a small molecule agent selected from those listed in Table 2 of Jerry L. Adams ET. AL.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BiTE®) antibody construct. In some embodiments, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MED10562 (Medimmune/AstraZeneca), an agonistic anti-OX40 antibody, in advanced solid tumors (NCT02318394 and NCT02705482); MED16469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its “do not eat” signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MED19447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

In addition to the prevention and/or treatment methods as described above, the present invention also provides the corresponding use for preventing and/or treating a disease, disorder, or condition as described herein. In some embodiments, the present invention provides a use of a compound or a pharmaceutically acceptable salt thereof, as described herein, for preventing and/or treating an viral infection, or an inflammatory disease, disorder, or condition, or a cancer, as described herein. In some embodiments, a use for preventing and/or treating an HIV infection as provided by the invention, is intended for a patient whose presence and/or expression level of an HIV splice variant as a biomarker is measured and/or monitored by the methods as described herein. In some embodiments, a use for preventing and/or treating an inflammatory disease, disorder, or condition, or a cancer, as provided by the invention, is intended for a patient whose presence and/or expression level of a spliced long noncoding RNA at miR-124 locus as a biomarker is measured and/or monitored by the methods as described herein.

Herein is further provided a compound of formulas I, Ia, Ib, b', Ic, Id, IV, IVa, IVb, IVb', IVc, or IVd as defined above, or a pharmaceutically acceptable salt thereof, for use for treating or preventing an inflammatory disease, disorder or condition, or a cancer in a patient in need thereof. In some embodiments, a compound of formulas I, Ia, Ib, Ib', Ic, Id, IV, IVa, IVb, IVb', IVc, or IVd as defined above, or a pharmaceutically acceptable salt thereof, for use as an anti-inflammatory agent is intended for patients whose presence and/or expression level of a spliced long noncoding RNA at miR-124 locus is monitored in a blood and/or tissue sample of said patient, prior to and/or during the course of said use.

Herein is further provided a compound of formulas I, Ia, Ib, Ib', Ic, Id, IV, IVa, IVb, IVb', IVc, or IVd as defined above, or a pharmaceutically acceptable salt thereof, for use for treating an HIV infection in a patient in need thereof. In some embodiments, a compound of formulas I, Ia, Ib, Ib', Ic, Id, IV, IVa, IVb, IVb', IVe, or IVd as defined above, or a pharmaceutically acceptable salt thereof, for use as an HIV treatment agent is intended for patients whose presence and/or expression level of an HIV splice variant is monitored in a blood and/or tissue sample of said patient, during the course of said use.

Further Exemplary Embodiments

1. A method of using an HIV splice variant of SEQ. ID. No. 1, as a biomarker of an HIV infection, or of an efficacy of a therapeutic treatment of an HIV infection, comprising measuring a presence or an expression level of the HIV splice variant of SEQ. ID. No. 1 in a biological sample.

2. A method of assessing biological effect of a compound on treating an HIV infection, comprising measuring a presence or an expression level of the HIV splice variant of SEQ. ID. No. 1 as a biomarker of an HIV infection.

3. A method of screening a compound or a vaccine in preventing and/or treating an HIV infection, comprising measuring a presence or an expression level of the HIV splice variant of SEQ. ID. No. 1 as a biomarker of an HIV infection.

4. A method of treating an HIV infection, comprising administering a therapeutic treatment to a patient, and measuring and/or monitoring a presence and/or expression level of the HIV splice variant of SEQ. ID. No. 1 in the patient.

5. A method of using lncRNA 0599-205 at the miR-124-1 locus as a biomarker of an inflammatory disease, disorder, or condition, or a cancer, or of an efficacy of a therapeutic treatment of an inflammatory disease, disorder, or condition, or cancer, comprising measuring a presence or an expression level of lncRNA 0599-205 at the miR-124-1 locus in a biological sample.

6. A method of assessing biological effect of a compound or a medical device on treating an inflammatory disease, disorder, or condition, or a cancer, comprising measuring a presence or an expression level of lncRNA 0599-205 at the miR-124-1 locus as a biomarker of an inflammatory disease, disorder, or condition, or a cancer.

7. A method of screening a compound or a medical device in treating an inflammatory disease, disorder, or condition, or a cancer, comprising measuring a presence or an expression level of lncRNA 0599-205 at the miR-124-1 locus as a biomarker of an inflammatory disease, disorder, or condition, or a cancer.

8. A method of treating an inflammatory disease, disorder, or condition, or a cancer, comprising administering a therapeutic treatment to a patient, and measuring and/or monitoring a presence and/or expression level of lncRNA 0599-205 at the miR-124-1 locus in the patient.

9. A method of treating an inflammatory disease, disorder, or condition, or a cancer, comprising administering a therapeutic treatment to a patient, and measuring and/or monitoring a presence and/or expression level of miR-124 in the patient.

10. A method of selecting a patient for a therapeutic treatment of an inflammatory disease, disorder, or condition, or a cancer, comprising measuring and/or monitoring a presence and/or expression level of lncRNA 0599-205 at the miR-124-1 locus in the patient.

11. A method of selecting a patient for a therapeutic treatment comprising measuring and/or monitoring a presence and/or expression level miR-124 in the patient.

12. The method of any one of embodiments 4 and 8-11, wherein the therapeutic treatment is a compound of Formula I:

I

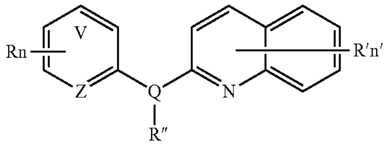

or a pharmaceutically acceptable salt thereof, wherein:

Z is C or N;

V is C or N;

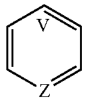

means an aromatic ring wherein V is C or N. and when V is N, V is ortho, meta or para relative to Z;

each R is independently hydrogen, halogen, —CN, hydroxyl, $(C_1\text{-}C_3)$fluoroalkyl, $(C_1\text{-}C_3)$fluoroalkoxy, $(C_3\text{-}C_6)$cycloalkyl, $—NO_2$, $—NR_1R_2$, $(C_1\text{-}C_4)$alkoxy, phenoxy, $—NR_1—SO_2—NR_1R_2$, $—NR_1—SO_2—R_1$, $—NR_1—C(=O)—R_1$, $—NR_1—C(=O)—NR_1R_2$, $—SO_2—NR_1R_2$, $—SO_3H$, $—O—SO_2—OR_3$, $—O—P(=O)—(OR_3)(OR_4)$, $—O—CH_2—COOR_3$, $(C_1\text{-}C_3)$alkyl, said alkyl being optionally mono- or di-substituted by a hydroxyl group or a group of formula (IIa):

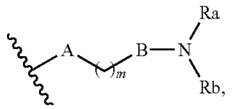

or a group of formula (IIIa):

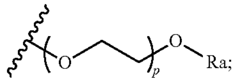

Q is N or O, provided that R" does not exist when Q is O;

each of $R_1$ and $R_2$ is independently hydrogen or $(C_1\text{-}C_3)$alkyl;

each of $R_3$ and $R_4$ is independently hydrogen, $Li^+$, $Na^+$, $K^+$, $N^+(Ra)_4$ or benzyl;

n is 1, 2 or 3;

n' is 1, 2 or 3;

each R' is independently hydrogen, $(C_1\text{-}C_3)$alkyl, hydroxyl, halogen, $—NO_2$, $—NR_1R_2$, morpholinyl, morpholino, N-methylpiperazinyl, $(C_1\text{-}C_3)$fluoroalkyl, $(C_1\text{-}C_4)$alkoxy, $—O—P(=O)—(OR_3)OR_4)$, —CN, a group of formula (IIa):

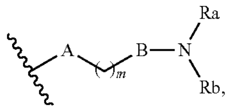

or a group of formula (IIIa):

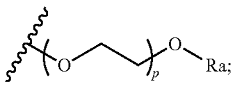

A is a covalent bond, oxygen, or NH;

B is a covalent bond or NH;

m is 1, 2, 3, 4 or 5;

p is 1, 2 or 3;

each of Ra and Rb is independently hydrogen, $(C_1\text{-}C_5)$alkyl, or $(C_3\text{-}C_6)$cycloalkyl, or Ra and Rb form together with the nitrogen atom to which they are attached a saturated 5- or 6-membered heterocycle, said heterocycle being optionally substituted by one or more Ra, provided that when R' is a group (IIa) or (IIIa), n' may be 2 or 3 only if other R' groups are different from said group (IIa) or (IIIa); and R" is hydrogen, $(C_1\text{-}C_4)$alkyl, or a group of formula (IIa) as defined herein.

13. The method of embodiment 12, wherein the compound is selected from formulas Ia-Id:

Ia

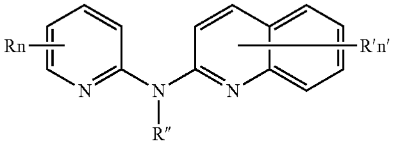

Ib

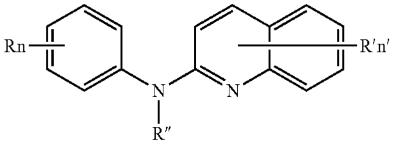

Ic

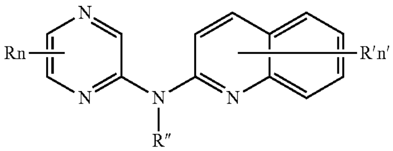

Ib'

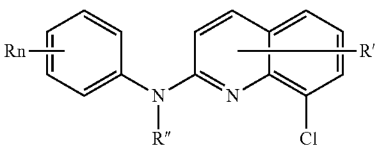

Id

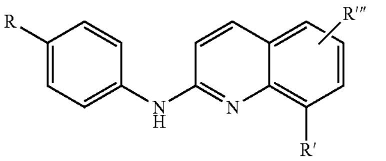

or a pharmaceutically acceptable salt thereof.

14. The method of embodiments 12 or 13, wherein the compound is ABX464, or a pharmaceutically acceptable salt thereof.

15. The method of any one of embodiments 4 or 8-11, wherein the therapeutic treatment is a compound of formula IV:

IV

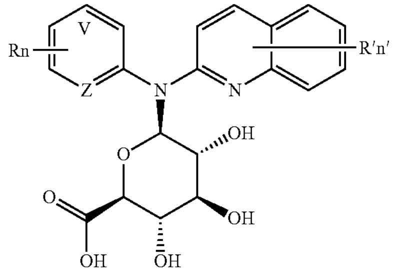

or a pharmaceutically acceptable salt thereof, wherein each of variables V, Z, R, R', n, and n' is as described in embodiment 8.

16. The method of embodiment 15, wherein the compound is selected from formulas IVa-IVd:

IVa

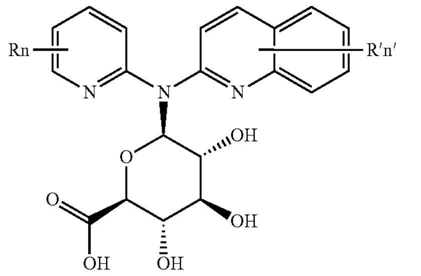

IVb

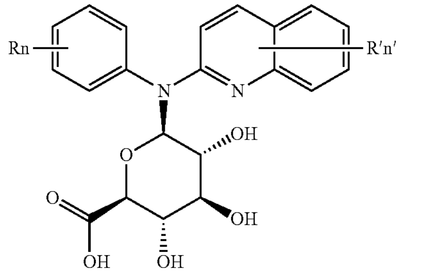

IVc

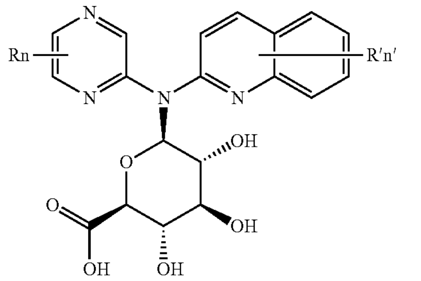

IVb'

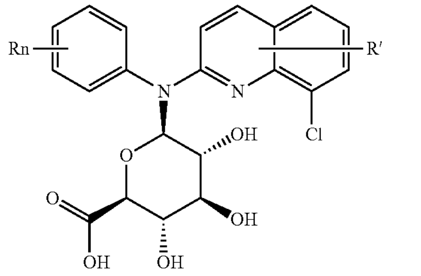

-continued

IVd

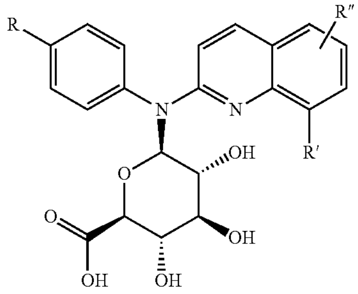

or a pharmaceutically acceptable salt thereof.

EXEMPLIFICATION

Human Samples

All experiments on human biopsies were performed in accordance with relevant guidelines and regulations. The experiments were approved by the AEMPS (Spanish Agency) No AEMPS: 16-0728 under the contract No EudraCT: 2016-002797-1título ESTUDIO ABIERTODE LA SEGURIDAD, FARMACOCINÉTICA Y FARMACODINÁMICA DE ABX464 EN ADULTOS SERONEGATIVOS Y SEROPOSITIVOS PARA EL VIH-1. Informed consent was obtained from all subjects.

Cell Culture, Infection and Transfection

Buffy coats from HIV-negative individuals were obtained from the local blood donation center in Centre de transfusion sanguine Montpellier. Human peripheral blood mononuclear cells (PBMCs) were isolated by Ficoll (Histopaque, Sigma) gradient centrifugation. CD4+ and CD8+ T cells were purified from PBMCs after Ficoll gradient centrifugation by Human CD4+ beads positive selection and CD8+ beads positive selection, respectively (Miltenyi). PBMCs, CD4+ and CD8+ T cells were grown at 37° C. and 5% CO2 to a density of 1.5×106 cells/ml in RPMI GlutaMAX medium (Life Technologies) supplemented with 10% fetal calf serum (FCS) (Thermo Fisher), 40 U/ml of IL2 (PeproTech) and 5 μg/mL of PHA (Roche) for 2 days. Three days later, cells were resuspended at 1.5×106 cells/ml in RPMI supplemented with 10% FCS and 40 U/ml IL2 and separated into two parts (infected and uninfected cells). Cells were infected with 80 ng of p24/106 cells of the YU-2 strain for 4 to 6 hours and then rinsed with PBS before medium renewal.

Both infected and uninfected cells were then centrifuged and resuspended to a density of 1.5×106 cells/ml in medium supplemented with diluted drug solubilized in DMSO (Sigma) to a final 0.05% DMSO concentration or antiretroviral compounds according to the manufacturer's instructions. Cells were treated for 6 days with a medium renewal at day 3. HIV p24 titration was performed by ELISA from cell culture supernatants with Innotest kit (Ingen) according to the manufacturer's instructions.

To generate monocyte-derived macrophages, monocytes were isolated using CD14+ positive microbeads (Miltenyi) and cultured in X-VIVO 10 medium (Lonza) supplemented with 10 mM HEPES, 1 mM sodium pyruvate, 1% non-essential amino acids, 10% FBS, 10 ng/ml GM-CSF and 100 ng/ml M-CSF for 7 days with medium renewal at day 3. After 7 days of differentiation, the cells were washed, plated in 6-well plates and incubated for 24 hours in medium without cytokine addition. Cells were treated for 6 days with a partial medium change at day 3.

HeLa cells from ATCC were cultivated at 37° C. and 5% CO2 in DMEM GlutaMAX medium (Life Technologies) supplemented with 10% FCS (Thermo Fisher). The region corresponding to lncRNA0599-205 was synthesized by IDT (Integratde DNA Technologies) and cloned into pcDNA3.1 to generate the pc-lncRNA-0599-205 plasmid. pc-lncRNA-0599-205 (2 μg per 400,000 cells) was transiently transfected in HeLa cells using jetPEI reagent (Polyplus) according to the manufacturer's instructions.

miRNA (RT-q)-PCR Analysis miRNAs were extracted from PBMCs, CD4+ or CD8+ T cells using the NucleoSpin miRNeasy kit (Macherey-Nagel) according to the manufacturer's instructions, miRNA reverse transcription (RT) was performed using the miScript II RT kit (Qiagen). The resultant cDNA was used as a template for real-time qPCR performed with the miScript SYBR Green PCR kit (Qiagen), together with the appropriate primers (Qiagen). A specific miR-124 primer (Hs_miR-124a), a control-specific primer (Ce_miR-39) and two housekeeping gene (miR-26 and miR-191)-specific primers (Hs_miR-26a and Hs_miR-191) were used to perform relative qPCR. The PCR analysis was performed on a LightCycler 480 Instrument II (Roche Molecular Systems, Inc). All reactions were run in triplicate. The relative levels of miR-124 were calculated using the $2^{-\Delta\Delta Ct}$ method.

Total RNA was extracted from macrophages using the Macherey-Nagel NucleoSpin miRNeasy kit, miRNA reverse transcription (RT) was performed on 2 μl of total RNA according to the Applied Biosystems TaqMan Advanced miRNA assays protocol for TaqMan qPCR. A specific miR-124 primer (Hs_miR-124a), a spike control-specific primer (Ce_miR-39) and housekeeping gene (miR-191)-specific primers (Hs_miR-191) were used to perform relative qPCR. PCR runs were analyzed with Applied Biosystems ViiA 7 software.

miR-124 Quantification in Human Biopsies

Quantification of miR-124 was performed on rectal biopsies sample from patients that have been collected in PAXgene Tissue Containers (PreAnalytiX). RNA extractions were performed using the PAXgene Tissue miRNA Kit (PreAnalytiX) following manufacturer's protocol. Briefly, samples were immersed in 250 μl of Buffer TM1 in a 2 ml Safe-Lock microcentrifuge tube containing one 5 mm stainless bead. Samples were disrupted and homogenized using Qiagen TissueLyser apparatus during 2×2 minutes at 20 Hz. The rest of the procedure was performed following the manufacturer's protocol. At the end of the procedure, each RNA was eluted into 32 μl of TM4 Buffer. RNA concentration and purity were measured using a NanoDrop ND-1000 spectrophotometer (Thermo Scientific). RNA integrity was assessed using an Agilent 2200 TapeStation with RNA ScreenTape. cDNA templates were prepared using the TaqMan Advanced miRNA cDNA Synthesis Kit (Applied Biosystems) starting from the 10 ng total RNA matrix and following the manufacturer's protocol. qPCR was carried out using two TaqMan Advanced miRNA Assays (Applied Biosystems), one targeting the miR-124-1 miRNA (assay ID: 477879 mir) and the other targeting an endogenous miRNA, miR16 (assay ID: 477860_mir), which was used as a reference for expression data normalization, according to the manufacturer's instructions. QPCR was performed on the LightCycler 480 Instrument II (Roche Molecular Systems, Inc). All assays were labeled using FAM-MGB chemistry.

Statistical Data Analysis

All statistical analyses and plots were done with R software v3.5. For normalization and processing, we used edgeR v3.22.1, EDASeq v2.14 and DESeq2 v1.20. We decided to use counts per million (CPM) over transcripts per million (TPM) mainly because TPM discards a lot of information about the original count sizes and thus would have produced too much noise for differential testing. The first step was to filter the data. We considered a gene to be expressed at a reasonable level in a sample if it had at least five counts for each million mapped reads in that sample. For marker selection, we used a type $1^{(*)}$ error α threshold set to 5%, enabling a highly flexible approach to the differential analyses despite the lack of replicates. For the same reason, the $\log_2$ fold change cutoff was set to 1.5 for both positive and negative values, and the cutoff p-value was typically ≤0.05. Those appropriate cutoffs allowed us to identify differentially expressed genes. The false discovery rate (FDR) values were computed for illustration purposes but were not taken into account in the decision due to the lack of replicates. The first methodology choice was Benjamini and Hochberg. This procedure provides less stringent control of type 1 errors compared to familywise error rate (FWER) procedures (such as the Bonferroni correction). We added an MDS plot for the data with R and edgeR package. The MDS plot produces a plot in which distances between samples correspond to the leading biological coefficient of variation (BCV) between those samples. In this plot, we did not observe segregation between the DMSO-NI, 464-NI, DMSOI and 464-I conditions. We also produced several volcano plots with R and the EDASeq package. These plots were a good representation of the differential expression (DE) testing in the RNA-Seq experiments. These plots showed the $\log_2$fold-change (FC) and the $-\log_{10}$ of p-values for all genes investigated in the DE test. The green points highlighted are markers that satisfied our selection criteria (significant in both p-value and $\log_2$FC). The yellow points highlighted are genes that satisfied the $\log_2$FC criterion but failed the p-value criterion. We retained these points to investigate further even though they had no decisional value.

Sequencing and Bioinformatics Analysis

RNA CaptureSeq of HIV RNA and Cellular microRNAs

Total RNA was extracted from infected and uninfected PBMC samples using TRIzol reagent (Invitrogen) following the manufacturer's protocol. The RNA concentrations and purity were determined using the RNA 6000 Bioanalyzer kit (Agilent). For cDNA synthesis, 1 μg of total RNA was treated with DNase I (Invitrogen) and then utilized as a template for reverse transcription using the Verso cDNA kit with a blend of random hexamers and anchored oligo-dT (Thermo Scientific), according to the manufacturer's instructions. After KAPA Hyper Prep (ROCHE) library preparation from 1 μg total RNA, we proceeded with SeqCap EZ capture (ROCHE) following the manufacturer's recommendations. Hybrid selection was performed with a custom SeqCap EZ Choice Library (Roche NimbleGen) containing the following regions; chromosome 8 (9,760,617 to 9,761,780 and 65,285,285 to 65,296,944), chromosome 20 (61,797,549 to 61,812,855), chromosome 1 (1,102,000 to 1,106,000), chromosome 13 (92,000,074 to 92,006,833), chromosome 15 (22,512,831 to 2,513,641) and the genome of the HIV Ada8 strain. This library was designed through the NimbleDesign portal (v1.2.R1) using genome build hg19 NCBI Build 37.1/GRCh37. Sequencing was performed on a NextSeq 500 (Illumina) with 18 samples on a HighOutput Cartridge (2×400 million reads of 75 bases each).

CD4+ T Cells Sequencing

A full-detailed report describing the complete analysis was submitted to Gene Expression Omnibus (GEO, https:// www.ncbi.nlm.nih.gov/geo/query/acc.cgi?acc=GSE116073). Total RNA extraction was performed according to the Qiagen miRNeasy □ kit. RNA concentrations were determined using Qubit□ fluorometric quantification and purity by the RNA 6000 Bioanalyzer kit (Agilent). RNA-Seq libraries were constructed with the TruSeq stranded mRNA sample preparation (low-throughput protocol) kit from Illumina, according to the manufacturer's instructions. Aliquots of 1.2 μg of total RNA were used for the construction of the libraries. The final cDNA libraries were validated with a Fragment Analyzer (Advanced Analytical, Ankeny, IA) and quantified with a KAPA qPCR kit (Kapa Biosystems, Wilmington, MA). On the 8 sequencing lanes of a flow cell V4, the 32 libraries were pooled in equal proportions by sets of 4 libraries per lane, denatured with NaOH and diluted to 16 μM before clustering. Cluster formation and primer hybridization and single-end read, 50-cycle sequencing were performed on the cBot and HiSeq 2500 (Illumina, San Diego, CA), respectively. Image analysis and base calling were performed using the HiSeq Control Software with the Real-Time Analysis component. Demultiplexing was performed using Illumina's sequencing analysis software. The quality of the data was assessed using FastQC from the Babraham Institute and the Illumina software SAV (Sequence Analysis Viewer). Potential contaminants were investigated with the FastQ Screen software from the Babraham Institute.

To investigate splicing activity we used SUPPA v2.0.0, a tool developed in Python 3.4 and especially designed for this approach. To study splicing across multiple conditions, we performed three modular operations that were run separately. The first step was to generate events from the annotation file commonly named the GTF file (general transfer format). The second step was to quantify event inclusion levels (PSIs) from our samples. Finally, differential splicing across multiple conditions was calculated for all replicates.

To generate the different alternative splicing events from an input annotation file (GTF format), the method reads transcript and gene information solely from the "exon" lines in the GTF. It then generates the events and outputs an 'ioe' file, which contains the relationship between each event and the transcripts that share this particular event. Specifically, it provides the transcripts that contribute to the numerator (one form of the event) and the denominator (both forms of the event) of the PSI calculation. For the generation of PSI values, SUPPA reads the ioe file generated in the first step and a transcript expression file with the transcript abundances.

SUPPA calculates the magnitude of the splicing changes (ΔPSI) and their significance across the biological conditions, using four replicates per condition. Conditions are analyzed in a sequential order specified as input. Statistical significance is calculated by comparing the observed ΔPSI between conditions with the distribution of the ΔPSI between replicates as a function of gene expression (measured as the expression of the transcripts defining the events). Using the output from the differential splicing analysis, we classified the events into four major groups: Alternative 5' splice site (A5), Alternative 3' splice site (A3), Alternative first and last exons (Altexons) and Retained intron (RI). Using this classification, we classified the differential splicing events encountered in the different comparisons of samples using a very stringent cutoff of psi-score difference (ΔPSI) fixed at >0.4 and a p-value <0.05. We used simple Perl scripts to establish raw count tables from the SUPPA outputs.

MicroRNA Array Analysis

Total RNAs were extracted from infected and uninfected PBMC samples using miRNeasy kit (Qiagen) following the manufacturer's protocol. The RNA concentrations were determined using the Nanodrop spectrophotometer (ThermoFisher). Quality controls were performed using expression console metrics. A full-detailed report describing the complete analysis was submitted to GEO (https://www.ncbi.nlm.nih.gov/geo/query/acc.cgi?acc=GSE116148). All miRNA arrays were normalized using "RMA+DABG" normalization method within the Affymetrix Expression Console with dedicated annotation files downloaded from the Affymetrix web server. Probes were considered expressed if the DABG p-value was less than 0.05 and not expressed otherwise. A miRNA was considered expressed in one condition if the probe was expressed in ¾ or more of the replicates. Finally, a miRNA was considered differentially expressed between conditions A and B if 1) it was expressed in A or B; 2) its fold change was ≥1.5; and 3) its paired t-test p-value was ≥0.05.

The volcano plots were produced using R. They show the M-value (log 2(fold change)) and the −log 10(p-value) of all miRNAs for the comparisons 464_I vs. DMSO_I, 464_NI vs. DMSO_NI and DMSO_I vs. DMSO_NI. The significantly (FC ≥1.5 and p-value ≤0.05) upregulated miRNAs were highlighted in red and the downregulated miRNAs in green.

TaqMan Low Density Array (TLDA)

MicroRNA profiling of samples was performed using TaqMan Array Human MicroRNA panels A and B (Life Technologies). Each TLDA card detects 384 features, including 377 human miRNAs, three endogenous small RNA controls (one of them being in quadruplicate), and a negative control. In total, 754 human miRNAs were quantified. Reverse transcription and preamplification were performed following the manufacturer's instructions (Megaplex™ RT Primers and Megaplex™ PreAmp Primers, Life Technologies). Nine microliters of diluted preamplified product added to 900 μL of total mix were used per TLDA card. Real-time quantitative PCR was performed with the ViiA 7 real-time PCR system, and the data were collected with the manufacturer's ViiA™ Software. Gene Expression Suite software (Applied Biosystems) was further used to process the array data. Automatic thresholds were checked individually and corrected when necessary.

In the data preprocessing step, the HiSeq control and real-time analysis software generates image analysis, base calling, and base call quality automatically in real time. "Dirty" raw reads were defined as reads that contained adaptor sequence or high content of unknown bases and low-quality reads. These reads were removed before downstream analysis to decrease data noise. The filtering steps were as follows:

The quality of the RNA-seq libraries was first evaluated using the FastQC v0.11.5 software. We use the FastQ Screen Contaminant finder to test the alignment of a large set of data to different genomes representing potential sources of contamination. The software generates a graph showing the proportions of reads aligning with the different genomes tested. FastQ Screen uses the Bowtie2 aligner. Alignment is performed on a subset of the sequences of each sample.

Then, the reads were subjected to standard quality control (QC) and filter criteria according to the following parameters: (1) trimming and cleaning reads that aligned to primers and/or adaptors, (2) reads with over 50% low-quality bases (quality value ≤15) in one read, and (3) reads with over 10% unknown bases (N bases). We used a program called Trimmomatic to remove primers and bad quality reads. After filtering, we removed short reads (<36 bp); the remaining reads are called "clean reads" and were stored in FASTQ format.

Once we were confident in the quality of our sequencing data, we proceeded to align the clean reads within FASTQ files to a reference sequence. Alignments were performed using the TopHat2 v2.0.8b tool against the human GRCh38 reference genome.

TopHat2 is a splice-aware aligner that uses the Bowtie2 aligner to align the data before counting the reads that are mapped to each gene. Bowtie2 behavior was adjusted to support local alignment by setting it to sensitive. TopHat2 outputs were stored in BAM files (accepted_hits.bam, typically) that contained all the alignments. TopHat2 outputs also reported alignment statistics. As the SAM file format was then required to count the reads, BAM files were sorted by name and converted to SAM format using the SAMtools-1.3.1 software. To compute gene level raw counts from the mapped reads in each library, we used the tool htseq-count v0.6.1p1 of the Python package HTSeq, using the default union-counting mode. The HTSeq package produced a raw counts table for each library, which was needed to determine each gene's expression level. DEG (differentially expressed gene) screening aims to find genes differentially expressed between the samples and perform further functional analysis on them. Gene expression levels and DEGs were computed by R software and a suite of R packages. We opted to focus our efforts and limit our statistical analysis to only specific libraries to outline and gain a deeper understanding of the effect of ABX464. In our work, we decided to compare DMSO versus DMSOi libraries, ABX464 versus DMSO libraries and 464i versus DMSOi libraries. Additionally, to obtain a meaningful result, in our statistical design, we considered the 4 donors as biological replicates.

Flow Cytometry

PBMCs or CD4+ T cells from different donors in suspension were labeled with appropriate anti-human monoclonal antibodies (mAb) (all from BioLegend). Washing and reagent dilutions were performed with FACS buffer (PBS containing 2% fetal calf serum and 0.05% sodium azide [NaN3]). All acquisitions were performed on a Cyan ADP (Beckman Coulter) flow cytometer. Data were analyzed with FlowJo software (Ashland, OR). Cellular debris and dead cells were excluded by their light-scattering characteristics.

Measurement of Unspliced and Spliced lncRNA 599-205

The retrotranscription (RT) reactions were performed with 1 μg of total RNA using the Maxima First Strand cDNA Synthesis Kit (ThermoFisher Scientific). Genomic DNA elimination was performed before amplification, but nevertheless, an RT negative control was performed without enzyme to confirm the absence of DNA contamination. qPCR was performed with the LightCycler® 480 SYBR Green I Master Mix (Roche) and the following primers: total lncRNA 599-205 Fwd (CCCTCCACCACTTGGGAC) and total lncRNA 599-205 Rev (GACCTGGGGATTCAGCCTTC), unspliced lncRNA 599-205 Fwd (GAACAAAGAGCCTTTGGAAGAC) and unspliced lncRNA 599-205 Rev (GGAAGGGACCACAGCATC), spliced lncRNA 599-205 Fwd (CACTCAGCGATGGAGGAAA) and spliced lncRNA 599-205 Rev (CCAATCACACAGACAATGAGATAAC), internal control β-actin Fwd (GTGAAGGTGACAGCAGTCGGTT) and β-actin Rev (GAAGTGGGGTGGCTTTTAGGA). The amplification run conditions were as follows: 95° C. (10 seconds), 58° C. (30 seconds), and 72° C. (30 seconds) for 40 cycles.

Results

1. ABX464 Generates Spliced HIV RNA Variants

To profile viral transcriptional events modulated by ABX464 and thereby assess the full depth of the HIV transcriptome, we employed a recently described targeted RNA capture and sequencing strategy (RNA CaptureSeq). This strategy involves the construction of tiling arrays across the HIV genome, against which cDNAs are hybridized, eluted and sequenced. RNA CaptureSeq is similar to previous in-solution capture methods and exome sequencing approaches, but when combined with deep-sequencing technology, provides saturating coverage and permits the robust assembly of rare and unannotated HIV transcripts.

Figure 6:
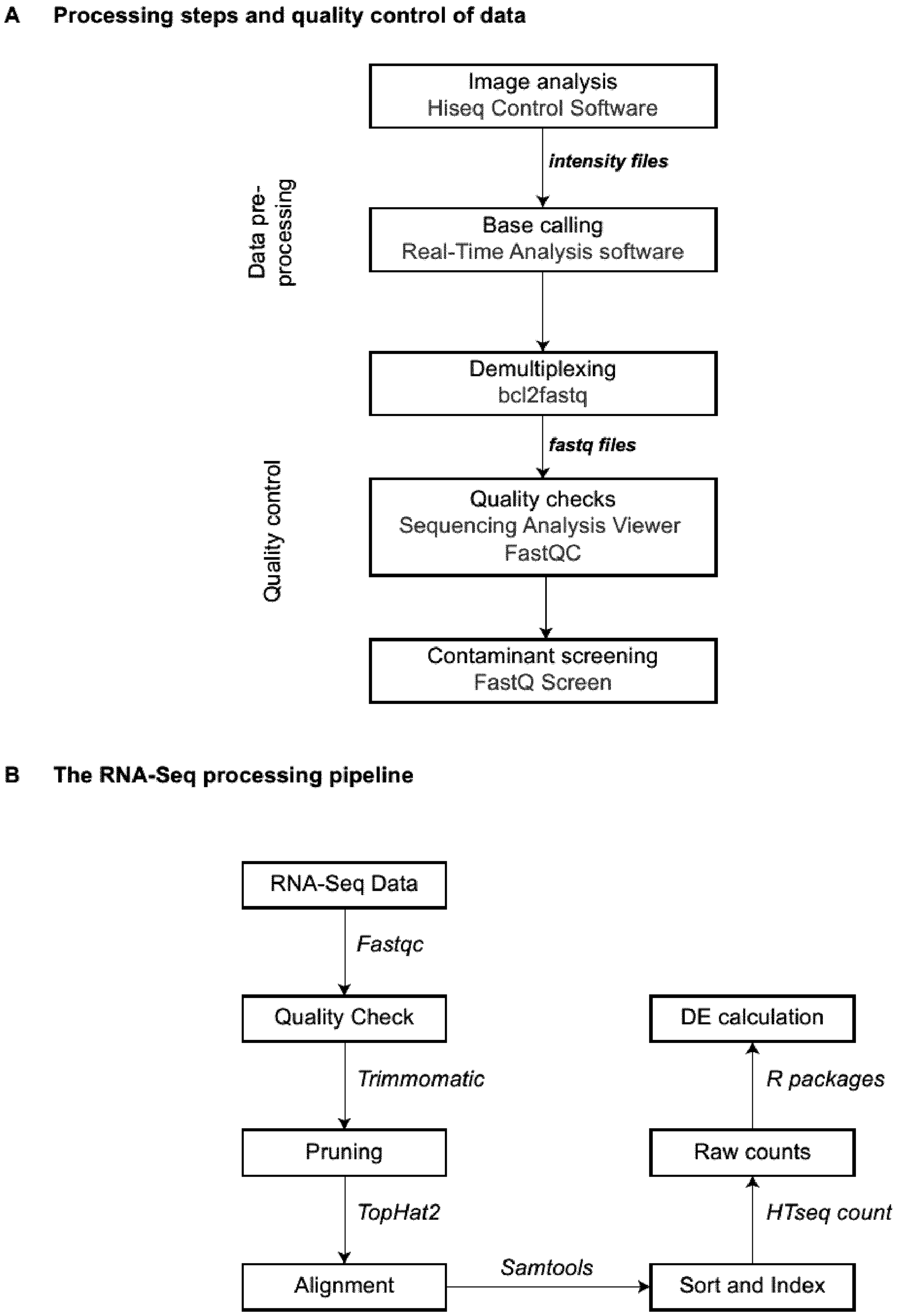
FIG. 6 depicts: A. Processing steps, and B, the RNA-seq processing pipeline.

PBMCs from 6 HIV-negative donors were infected with the YU-2 strain, followed by treatment with ABX464. Our protocol resulted in mild infection that did not lead to cell death at 8 days postinfection (dpi), and viral replication was inhibited by more than 70% with 5 μM of ABX464 (FIG. 1B). After cDNA capture from infected cells that were untreated or treated with ABX464, libraries were prepared and sequenced using an Illumina sequencing facility. To highlight potential new splicing events induced by ABX464, we used a custom bioinformatics pipeline with the main step involving the assembly of putative transcripts from targeted RNA sequencing reads to construct contigs (Illumina paired-end 2×75 bp) (FIGS. 6 A and B). The putative transcripts (contigs) were then mapped to the HIV genome. The HIV profiling datasets used in our analysis yielded high sequence coverage (2 to 30 million reads for the 9 kb genome), allowing deep quantification of HIV splice variants. We were able to reliably quantify each HIV alternative splicing over a wide range of transcript abundances and show that while ABX464 treatment resulted in enhanced splicing, ABX464 did not favor generation of any splice variant over the others (FIG. 1C, Table III).

Figure 7:
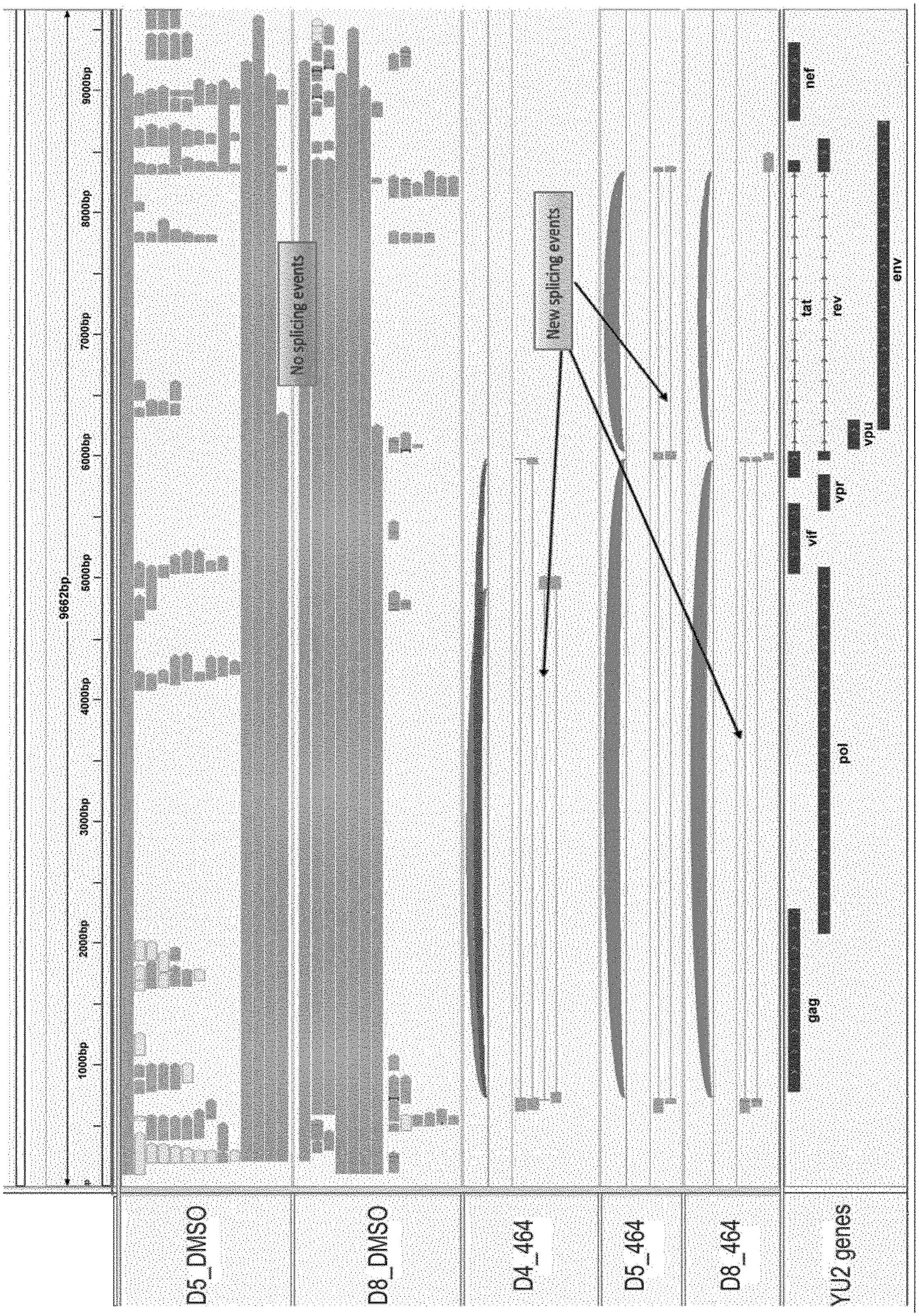
FIG. 7 depicts representation of assembled contigs from two untreated samples (D5_DMSO and D8_DMSO) and three ABX464 treated samples (D4_464, D5_464 and D8_464).

To test whether enhanced splicing by ABX464 generates new viral RNA variants, the splicing events were filtered and analyzed. After mapping the contigs to the genome of the YU-2 strain, the latter was used as an anchor for additional clustering and assembly of new HIV transcripts. The partial gene structures generated by the spliced alignment were merged whenever they shared consecutive splicing sites spanning an intronic viral sequence. The superstructures so formed correspond to all possible HIV gene structures for which each complete exon is supported by at least one of the alignments. At the HIV transcript level, this led to the formation of superassemblies, where each superassembly is a merge of initial contigs matching a predicted superstructure. Notably, the linking of contigs to the HIV-1 genomic sequence and the requirement that all splicing sites in merged contigs coincide, precluded the formation of spurious superassemblies. FIG. 1C and Table III present the distribution of the number of contigs that were merged to form one superassembly for each donor. While, in all samples treated by ABX464, most of the assembled contigs (90%) corresponded to spliced RNAs (FIG. 1C, Table IV and FIG. 7) or small RNAs containing gag-pol sequences that can be released from introns, in untreated samples, spliced RNAs represented a minor fraction (less than 24%), and the majority of contigs corresponded to full-length unspliced viral RNA (more than 74%) (FIG. 1C, Table IV and FIG. 7). This result demonstrated that ABX464 preferentially generated spliced HIV RNA variants in infected PBMCs, which would compromise the subsequent synthesis of full-length HIV-1 pre-mRNA and assembly of infectious particles, thereby leading to inhibition of viral replication.

Interestingly, one of the spliced variants generated by ABX464 treatment (FIGS. 1 A and D) was present in cells infected by both the YU-2 and Ada-M strains, and no polymorphism in its sequence was detected in the HIV-1 B and C subtypes that were strongly inhibited by ABX464. Furthermore, this new splice variant was detected using long read sequencing, which points to the additional accuracy that this method brings in delineating complex and rare spliced isoforms and estimating their relative abundances. This new RNA variant can generate immunogenic peptides or being toxic to cells harboring proviral DNA. This is consistent with the diminished viral loads and reduced viral DNA levels (ABIVAX, data in file) observed in HIV patients treated with ABX464. Thus, ABX464 not only enhanced the splicing of HIV RNA but also generated a new HIV splice variant.

Table III shows read assemblies and contig counts from PBMCs infected with the YU2 strain, either untreated (D1_DMSO, D4_DMSO, D5_DMSO, D6_DMSO, D7_DMSO and D8_DMSO) or treated with ABX464 (D1_464, D4464, D5_464, D6_464, D7_464 and D8_464).

Table IV shows contig counts of complete mRNA or spliced RNA transcripts of Gag, Pol, vif, vpr, tat, rev, vpu and env from PBMCs infected with YU2 strain, either untreated (D1_DMSO, D4_DMSO, D5_DMSO, D6_DMSO, D7_DMSO and D8_DMSO) or treated with ABX464 (D1_464, D4_464, D5_464, D6_464, D7_464 and D8_464).

TABLE III

| LIB names | Total paired-end reads before cleaning | Total paired-end reads after adapters cleaning | Total paired-end reads after contaminants cleaning | Total assembled contigs | Mapped contigs |
|---|---|---|---|---|---|
| D1_DMSO | 7 948 802 | 7 884 109 | 7 006 433 | 683 | 63 |
| D4_DMSO | 30 625 849 | 30 363 868 | 27 810 800 | 1873 | 373 |
| D5_DMSO | 27 140 691 | 26 874 233 | 23 571 947 | 693 | 273 |
| D6_DMSO | 2 997 402 | 2 927 628 | 2 674 892 | 558 | 38 |
| D7_DMSO | 15 024 678 | 14 803 409 | 13 887 294 | 1489 | 190 |
| D8_DMSO | 17 570 815 | 17 386 693 | 16 491 699 | 1687 | 180 |
| D1_464 | 4 940 644 | 4 879 559 | 4 557 902 | 362 | 90 |
| D4_464 | 30 800 345 | 30 505 238 | 28 468 138 | 1413 | 225 |
| D5_464 | 1 973 736 | 1 939 172 | 1 826 516 | 793 | 17 |
| D6_464 | 4 450 825 | 4 385 103 | 4 174 706 | 227 | 49 |
| D7_464 | 7 374 222 | 7 279 017 | 6 912 908 | 982 | 46 |
| D8_464 | 8 507 861 | 8 381 026 | 7 835 264 | 759 | 48 |

TABLE IV

| YU2 libraries | Complete_ mRNA | Gag | Pol | Vif | vpr | tat | rev | vpu | env |
|---|---|---|---|---|---|---|---|---|---|
| D1_DMSO | 123 | 6 | 9 | 2 | 6 | 2 | 2 | 5 | 3 |
| D4_DMSO | 174 | 6 | 12 | 5 | 5 | 7 | 9 | 11 | 8 |
| D5_DMSO | 194 | 6 | 7 | 6 | 4 | 8 | 11 | 5 | 10 |
| D6_DMSO | 80 | 3 | 10 | 3 | 2 | 8 | 2 | 4 | 2 |
| D7_DMSO | 146 | 6 | 6 | 2 | 7 | 2 | 8 | 3 | 6 |
| D8_DMSO | 166 | 8 | 4 | 9 | 2 | 4 | 3 | 10 | 4 |
| D1_464 | 11 | 18 | 67 | 32 | 14 | 16 | 23 | 7 | 59 |
| D4_464 | 13 | 42 | 61 | 34 | 14 | 18 | 21 | 5 | 42 |
| D5_464 | 6 | 25 | 17 | 15 | 9 | 19 | 17 | 13 | 37 |
| D6_464 | 32 | 13 | 14 | 16 | 12 | 15 | 9 | 11 | 13 |
| D7_464 | 15 | 19 | 12 | 12 | 11 | 18 | 12 | 11 | 35 |
| D8_464 | 6 | 26 | 35 | 25 | 12 | 24 | 29 | 17 | 42 |

2. ABX464 does not Affect Cellular Splicing

To ensure that ABX464 acted specifically on HIV splicing and did not significantly or globally affect the splicing events of human genes, we used a high-throughput RNAseq approach. Many genome-wide expression studies of HIV infection are based on analyses of total peripheral blood mononuclear cells (PBMCs), which consist of over a dozen cell subsets, including T cells. B cells, NK cells and monocytes. To avoid the dilution of the specific gene expression signals of particular cell subsets by those from the other cells and thus a reduction of the specificity of this approach, we used purified CD4+ T cells from the PBMCs of 4 donors. The CD4+ T cells were uninfected or infected with the YU-2 strain and were untreated or treated for 6 days with ABX464, followed by high-throughput RNAseq. Each raw dataset of the samples contained between 44 and 105 million single-end reads (50 bp), with an average of approximately 60 million raw reads per sample (FIG. 2A). More than 97% of the bases had a quality score of ≥Q20. Approximately 98% of the total raw reads were mapped to the human genome sequence (GRCh38), giving an average of 60 million human reads per sample for further analyses. The reads that were correctly mapped (approximately 98% of total input reads) to the gene and transcript locations (GTF annotation file) (FIG. 2A) were subsequently analyzed using in-house package suites for transcript abundance normalization and evaluation. Multidimensional scaling analysis (MDS) is an unsupervised global analysis approach and is useful for reducing the dimensionality of gene expression data (FIG. 2B). MDS minimizes dimensions, preserving the distances among data points, and allows for projecting multidimensional gene data onto just two or three new dimensions that explain most of its variance. As a result, it is possible to visually interpret major trends in the data, for example, in terms of the similarities among various data points. The MDS of our gene expression data showed, without any outliers, that the different donors separated well and distributed into the DMSO (untreated) and ABX464 treatments that were infected or uninfected. The displayed variance was donor-dependent (clustered by donor) but treatment-independent (no data structure related to the different treatments), which suggests that the ABX464 molecule did not induce a major difference in CD4+ T cell gene expression (FIG. 2B).

Figure 2C:
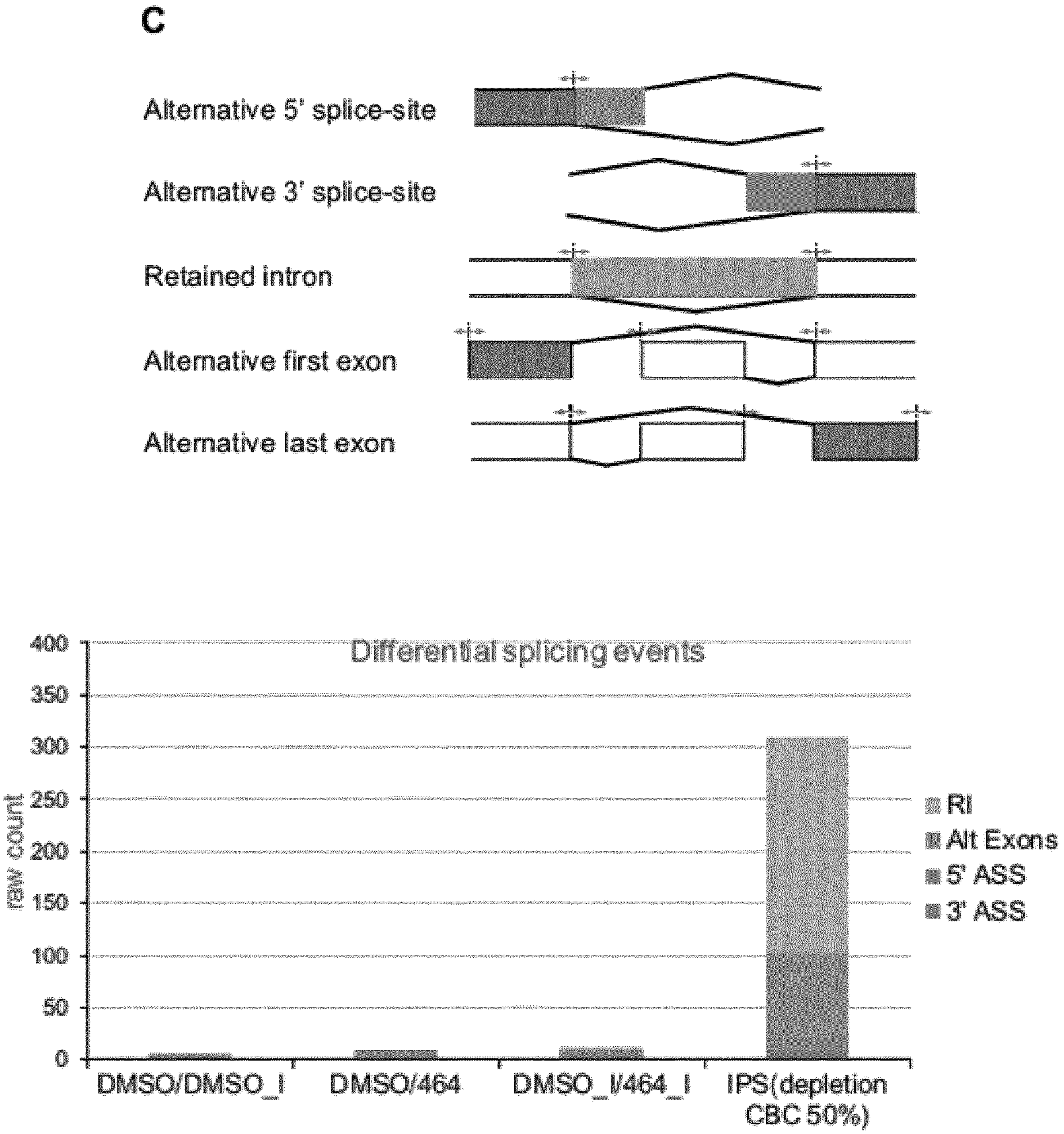
FIG. 2 depicts that ABX464 has no global effect on cellular splicing. A. The effect of ABX464 on infected and uninfected CD4+ T cells was tested by a high-throughput RNAseq approach. Sixteen libraries were constructed using 4 conditions: uninfected (DMSO_NI), uninfected treated with ABX464 (ABX464_NI), infected (DMSO_I) and infected treated with ABX464 (464_I), corresponding to 4 donors. Approximately 38 million reads (more than 50% of the total raw reads) were aligned to exons of the human genome sequence in each of the samples. B. Multidimensional scaling analysis (MDS) was used to interpret major trends in the data. C. Alternative splicing (AS) events of cellular genes were classified into five major groups (left panel): Alternative 5' splice site (A5SS, orange), Alternative 3' splice site (A3SS, blue), Skipped exon (SE, gray), Mutually exclusive exons (MXE, gray) and Retained exon (RI, yellow). AS event counts comparing infected vs uninfected samples (DMSO_I vs DMSO_NI), uninfected vs uninfected treated by ABX464 (DMSO_NI vs 464_NI), infected vs infected treated by ABX464 (DMSO_I vs 464_I) and after 50% depletion CBC in IPS (IPS depletion of CBC by 50%) (right panel). D. By comparing exon coverage reads of a common highly expressed gene (B2M) between the ABX464 and DMSO conditions in the 4 donors, we confirmed that ABX464 did not increase splicing events in B2M. E. Volcano plot of DMSO_I vs DMSO_NI (upper panel), DMSO_NI vs 464_NI (middle panel), DMSO_I vs 464_I (lower panel). The gene expression variation generated by ABX464 treatment was very low in infected (6 downregulated genes) and uninfected (6 downregulated genes) samples.
Figure 2D:
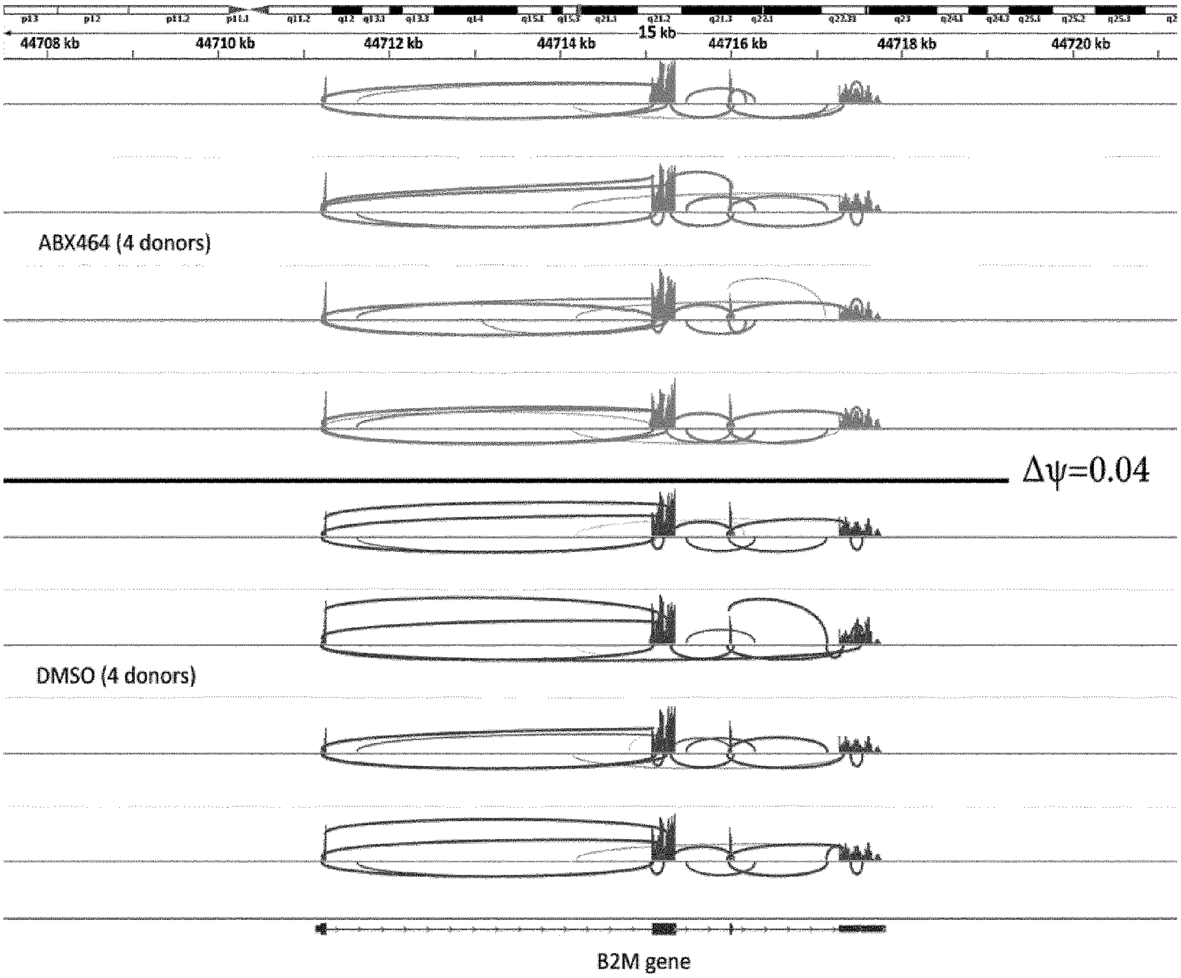
Figure 8:
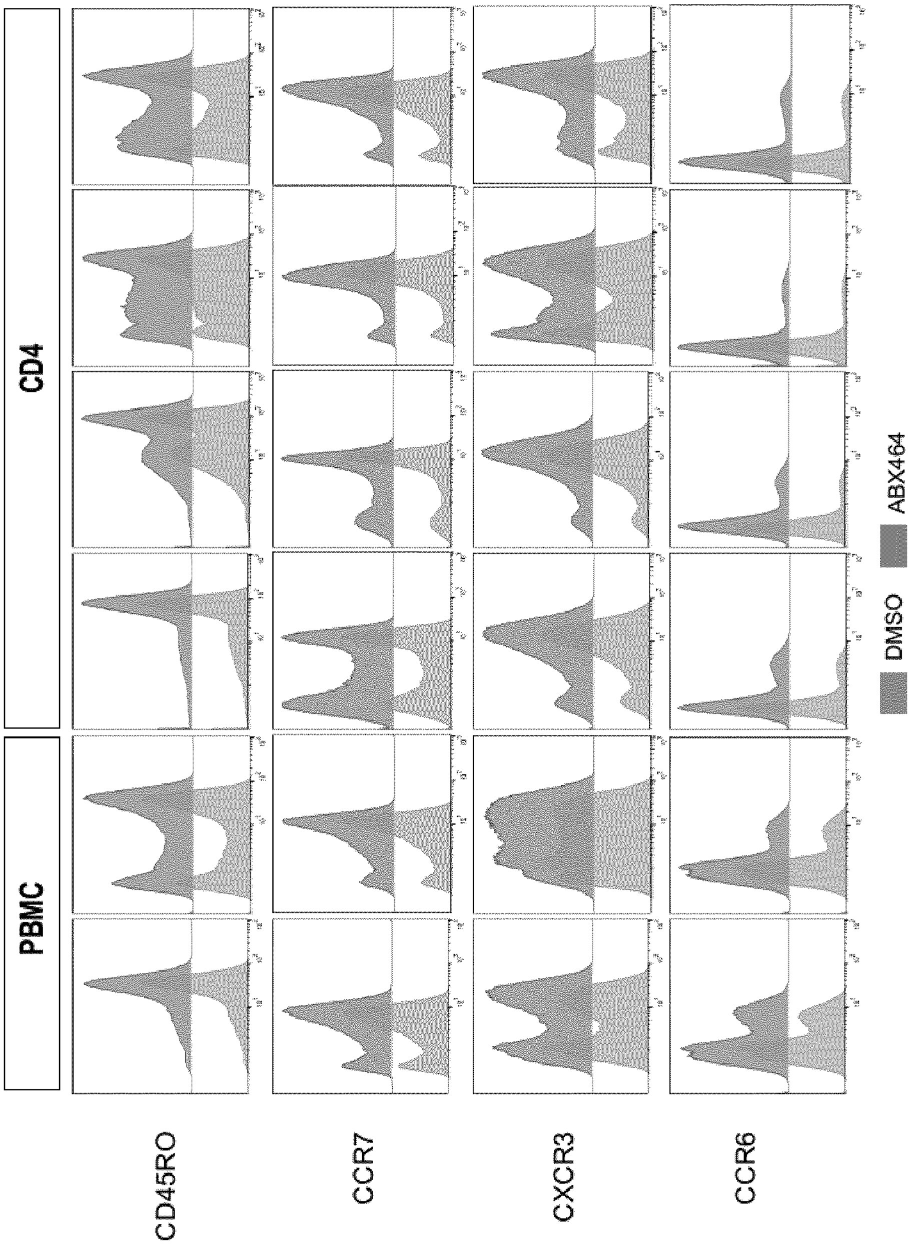
FIG. 8 depicts FACS analysis using CD45, CCR7, CCR3 and CCR6 surface markers of PBMCs (2 donors) and CD4 (4 donors) both untreated (red) and treated with ABX464 (blue).

For a gross estimation of the alternate splicing events modulated by ABX464 in infected and uninfected CD4+ T cells, we compared junction read counts that originated from exon-exon boundaries across different samples (FIG. 2C). While the alignment of reads to exon junctions was purely coincidental, we did not observe gross differences in the total number of reads corresponding to exon-exon boundaries between treated and untreated CD4+ T cells, whether infected or uninfected, across any of the samples (FIG. 2C). For a more statistically qualified assessment of alternate splicing in these CD4+ T cells, we followed a method for differential splicing analysis across multiple conditions named SUPPA (super-fast pipeline for alternative splicing analysis). The alternate splicing events were classified into five major groups: Alternative 5' splice site (A5SS), Alternative 3' splice site (A3SS), Alternative first and last exons (Alt exons) and Retained exon (RI) (FIG. 2C). A "percent splicing index (psi)" score (ψ-score) was calculated for each of the transcript variants for each sample. Using a stringent cutoff, the difference of ψ-score from untreated sample was fixed at 0.4 and p-value was fixed at 0.05 for differential splicing events induced upon treatment with ABX464 to be considered significant. The number of significant events for each of the 5 possible AS events is presented in FIG. 2C and Table I. No switch-like events were detected where the difference in psi-score was exactly 1 or −1. We next calculated the ψ-scores of transcripts in uninfected versus infected CD4+ T cells (FIG. 2C). No switch-like events were detected in infected or uninfected T CD4+ samples when compared to ABX464-treated samples (FIG. 2C). The exact numbers of common and differential splicing events between infected and uninfected CD4+ T cells treated with ABX464 were very low (fewer than 10 events, Table 1), while depletion of NCBP1 (Nuclear Cap Binding protein subunit 1), a component of the CBC, in stem cells by only 50% gave rise to large variations, with 81 Alt exon, 12 A 5'SS, 10 A 3'SS and 206 IR events (FIG. 2C). The high level of IR indicated that CBC complex is a major component preventing accumulation of unspliced RNA as most of unspliced transcripts will be degraded by nonsense mediated decay (NMD). Comparison of exon coverage reads of a common highly expressed gene, B2M, between the ABX464 and DMSO conditions in the 4 donors revealed that ABX464 did not increase splicing events in B2M (FIG. 2D). In summary, ABX464 treatment did not induce alternate splicing of transcripts, and therefore. ABX464 had no potential to dramatically alter gene expression in activated CD4+ T cells. Consistent with this result, FACS analysis of purified activated CD4+ T cells or PBMCs from 7 donors after 6 days of ABX464 treatment did not reveal any changes in the CCR6CXCR3 or CD45CCR7 (Th 17/Th1 and effector memory cells, respectively) subpopulation (FIG. 8).

Table I below lists splicing events in CD4 T cells: infected vs uninfected (DMSOI vs DMSO), uninfected treated with ABX464 vs uninfected and untreated (464 vs DMSO) and infected treated with ABX464 vs infected and untreated (464_I vs DMSO_I).

TABLE I

| ABX464_NI_VS_DMSO_NI | | | |
|---|---|---|---|
| Gene symbol | Ensembl ID | description | Event type |
| LINC01119 | ENSG00000239332 | long intergenic non-protein coding RNA 1119 | A3 |
| STMND1 | ENSG00000230873 | stathmin domain containing 1 | Alt exons |
| ZNF177 | ENSG00000188629 | zinc finger protein 177 | A3 |
| FGF22 | ENSG00000070388 | fibroblast growth factor 22 | A3 |
| AL139035.1 | ENSG00000280710 | Clone-based | Alt exons |
| MRPL52 | ENSG00000172590 | mitochondrial ribosomal protein L52 | A5; Alt exons |
| HCG20 | ENSG00000228022 | HLA complex group 20 (non-protein coding) | Alt exons |
| RHBDD2 | ENSG00000005486 | rhomboid domain containing 2 | Alt exons |
| AL157955.2 | ENSG00000258826 | Clone-based | A3 |
| TMEM147 | ENSG00000105677 | transmembrane protein 147 | RI |
| COX6C | ENSG00000164919 | cytochrome c oxidase subunit 6C | Alt exons |
| ATIC | ENSG00000138363 | 5-aminoimidazole-4-carboxamide ribonucleotide formyltransferase/IMP cyclohydrolase | A5 |
| STMND1 | ENSG00000230873 | stathmin domain containing 1 | Alt exons |
| GEM | ENSG00000164949 | GTP binding protein overexpressed in skeletal muscle | Alt Exons |
| CDRT15 | ENSG00000223510 | CMT1A duplicated region transcript 15 | A5 |
| WDR72 | ENSG00000166415 | WD repeat domain 72 | A5 |
| SMIM11A | ENSG00000205670 | small integral membrane protein 11A | AL |

TABLE I-continued

| | | | |
|---|---|---|---|
| EGLN2 | ENSG00000269858 | egl-9 family hypoxia inducible factor 2 | Alt exons |
| GNRHR2 | ENSG00000211451 | gonadotropin releasing hormone receptor 2 (pseudogene) | RI |
| ZNE584 | ENSG00000171574 | zinc finger protein 584 | A3 |
| LINC01869 | ENSG00000180279 | long intergenic non-protein coding RNA 1869 | A3 |

| DMSO_1_VS_DMSO_NI | | | |
|---|---|---|---|
| Gene symbol | Ensembl ID | description | Event type |
| CHTF8 | ENSG00000168802 | chromosome transmission fidelity factor 8 | Alt exons |
| KCTD2 | ENSG00000180901 | potassium channel tetramerization domain containing 2 | A5 |
| ETS1 | ENSG00000134954 | ETS proto-oncogene 1; transcription factor | A5 |
| RASAL2-AS1 | ENSG00000224687 | RASAL2 antisense RNA 1 | A5 |
| SLC16A9 | ENSG00000165449 | solute carrier family 16 member 9 | Alt exons |
| RPP40 | ENSG00000124787 | ribonuclease P/MRP subunit p40 | Alt exons |

3. ABX464 does not Alter Cellular Gene Expression

Figure 2E:
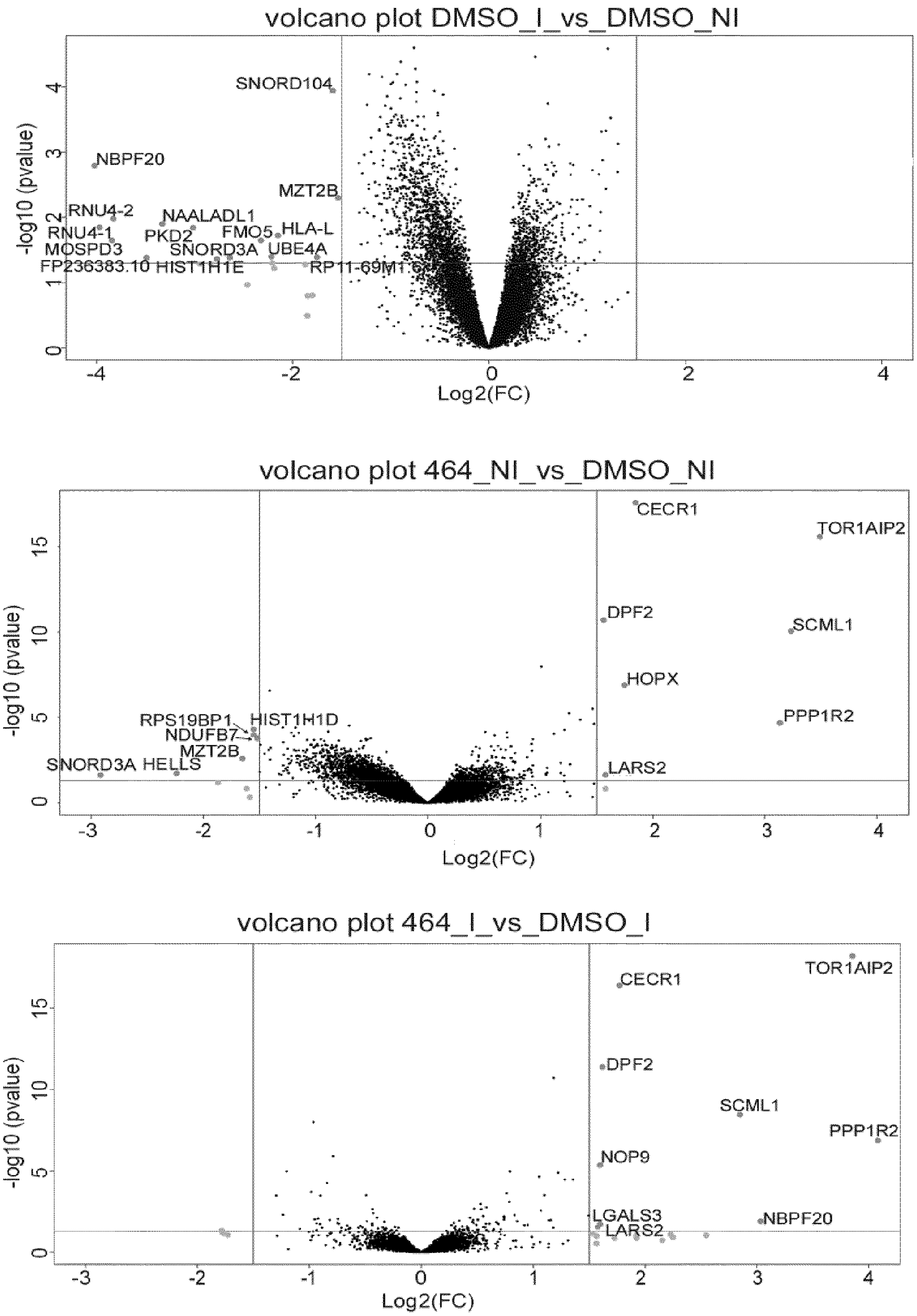

To determine whether ABX464 induced a quantitative change in the transcriptome of infected cells, we measured transcript levels (see FIG. 6 for pipeline) from the RNAseq data. More than 60 000 different transcripts were detected among all samples. After counts per million normalization (CPM), transcripts of each sample were filtered out with a coverage cutoff value of CPM >5; that is, a gene was considered to be expressed in a sample if it had at least five counts for each million mapped reads in that sample. Since this experiment used four donors, four replicates were available for each condition (infected/uninfected cells with/without ABX464 treatment), and a gene was considered to be expressed if it was expressed to at least five counts for each million mapped reads in all replicates. Following these selection criteria, we ended up with a list of transcripts common to all samples, including 11 700 different transcripts with an average of around 3 000 raw counts per transcript. Using the CPM values of the qualified genes, a global expression plot was produced for each donor. Under the conditions of mild infection used in our study, we did not detect strong changes in gene expression, with only 15 genes being downregulated in response to infection in untreated samples (FIG. 2E top panel, Table II). ABX464 treatment resulted in the upregulation of 9 genes in the infected samples, and 6 downregulated and 7 upregulated genes in the uninfected samples (FIG. 2E middle and lower panels, respectively; Table II), demonstrating a mild effect of ABX464 treatment on gene expression (FIG. 2E). The six genes that were upregulated following ABX464 treatment were shared between infected and uninfected samples, suggesting that this upregulation was mediated by ABX464 treatment and was independent of infection. Three of the six genes, TOR1AIP2, SCML1 and PPP1R2, had fold changes above 3 with p-values of $10^{-5}$. Interestingly, TOR1AIP2, a protein thought to regulate protein folding as well as intracellular trafficking, was recently shown to constrain the late steps of HIV replication and may, therefore, be an effector of ABX464-induced changes.

Table II below lists genes modulated in T CD4 cells: infected vs uninfected (DMSO_I vs DMSO), uninfected treated with ABX464 vs uninfected and untreated (464 vs DMSO) and infected treated with ABX464 vs infected and untreated (464_I vs DMSO_I). Upregulated genes in bold and down regulated genes in italics.

TABLE II

| DMSO_I_vs_DMSO_NI | | | | | | |
|---|---|---|---|---|---|---|
| Gene Symbol | Ensembl ID | chr | description | log2(FC) | FC | P-Value |
| SNORD104 | ENSG00000199753 | 17 | small nucleolar RNA, C/D box 104 | −1.593239134 | 0.3314265 | 0.000113748 |
| MZT2B | ENSG00000152082 | 2 | mitotic spindle organizing protein 2B | −1.545615646 | 0.342549493 | 0.005014214 |
| HLA-L | ENSG00000243753 | 6 | major histocompatibility complex, class I, L (pseudogene) | −2.155554923 | 0.224446745 | 0.018996735 |
| FMO5 | ENSG00000131781 | 1 | flavin containing monooxygenase 5 | −2.32723033 | 0.199266303 | 0.022279359 |
| RP11-69M1.6 | ENSG00000279865 | 12 | pseudogene | −1.75254756 | 0.296777256 | 0.040623948 |
| UBE4A | ENSG00000110344 | 11 | ubiquitination factor E4A | −2.226.441782 | 0.2136851 | 0.039977521 |
| SNORD3A | ENSG00000263934 | 17 | small nucleolar RNA, C/D box 3A | −2.648926643 | 0.159438656 | 0.041651979 |
| HIST1H1E | ENSG00000168298 | 6 | histone cluster 1 H1 family member | −2.769812645 | 0.146623409 | 0.043246739 |
| PKD2 | ENSG00000118762 | 4 | polycystin 2, transient receptor potential cation channel | −3.020380563 | 0.123246573 | 0.014543367 |
| NAALADL1 | ENSG00000168060 | 11 | N-acetylated alpha-linked acidic dipeptidase like 1 | −3.333148179 | 0.099225299 | 0.012581 |
| RNU4-1 | ENSG00000200795 | 12 | RNA, U4 small nuclear 1 | −3.972391545 | 0.063707563 | 0.014002979 |
| RNU4-2 | ENSG00000202538 | 12 | RNA, U4 small nuclear 2 | −3.830896068 | 0.070272495 | 0.010356151 |
| MOSPD3 | ENSG00000106330 | 7 | motile sperm domain containing 3 | −3.845633809 | 0.069558286 | 0.022670456 |
| FP236383.10 | ENSG00000277105 | 8 | miRNA | −3.494083339 | 0.088751583 | 0.040882842 |
| NBPF20 | ENSG00000162825 | 1 | Neuroblastoma Breakpoint Family, Member 20 | −4.017571383 | 0.061743395 | 0.001624932 |

| ABX464_NI_vs_DMSO_NI | | | | | | |
|---|---|---|---|---|---|---|
| Gene Symbol | Ensembl ID | chr | description | log2(FC) | FC | P-Value |
| SNORD3A | ENSG00000263934 | 17 | small nucleolar RNA, C/D box 3A | −2.923985868 | 0.13176 | 0.026481173 |
| HELLS | ENSG00000119969 | 10 | helicase, lymphoid specific | −2.246421514 | 0.21075 | 0.018558217 |
| MZT2B | ENSG00000152082 | 2 | mitotic spindle organizing protein 2B | −1.658291634 | 0.31681 | 0.002657817 |
| HIST1H1D | ENSG00000124575 | 6 | histone cluster 1 H1 family member d | −1.559586171 | 0.33925 | 5.18E−05 |
| RPS19BP1 | ENSG00000187051 | 22 | ribosomal protein S19 binding protein 1 | −1.566230636 | 0.33769 | 0.000115799 |
| NDUFB7 | ENSG00000099795 | 19 | NADH: ubiquinone oxidoreductase subunit B7 | −1.520475764 | 0.34857 | 0.000168054 |
| CECR1 | ENSG00000093072 | 22 | Adenosine Deaminase 2 | 1.842665068 | 3.58672 | 2.65E−18 |
| DPF2 | ENSG00000133884 | 11 | double PHD fingers 2 | 1.560531204 | 2.94962 | 2.45E−11 |
| HOPX | ENSG00000171476 | 4 | HOP Homeobox | 1.744005457 | 3.34964 | 1.47E−07 |
| LARS2 | ENSG00000011376 | 3 | leucyl-tRNA synthetase 2, mitochondrial | 1.580307045 | 2.99033 | 0.026767164 |
| TOR1AIP2 | ENSG00000169905 | 1 | torsin 1A interacting protein 2 | 3.485915121 | 11.20379 | 2.59E−16 |
| SCML1 | ENSG00000047634 | X | Scm polycomb group protein like 1 | 3.229297195 | 9.37811 | 9.67E−11 |

TABLE II-continued

| | | | | | | |
|---|---|---|---|---|---|---|
| PPP1R2 | ENSG00000184203 | 3 | protein phosphatase 1 regulatory inhibitor subunit 2 | 3.136231549 | 8.79224 | 2.52E−05 |

| ABX464_I_vs_DMSO_I | | | | | | |
|---|---|---|---|---|---|---|
| Gene Symbol | Ensembl ID | chr | description | log2(FC) | FC | P-Value |
| CECR1 | ENSG00000093072 | 22 | Adenosine Deaminase 2 | 1.770654479 | 3.41208711 | 4.33E−17 |
| DPF2 | ENSG00000133884 | 11 | double PHD fingers 2 | 1.61885639 | 3.07134797 | 4.52E−12 |
| NOP9 | ENSG00000196943 | 14 | NOP9 nucleolar protein | 1.594464835 | 3.019824765 | 4.35E−06 |
| LGALS3 | ENSG00000131981 | 14 | galectin 3 | 1.589357824 | 3.009153755 | 0.723536038 |
| LARS2 | ENSG00000011376 | 3 | leucyl-tRNA synthetase 2, mitochondrial | 1.580389838 | 2.990506469 | 0.025849185 |
| SCML1 | ENSG00000047634 | X | Scm polycomb group protein like 1 | 2.85086263 | 7.214316067 | 3.52E−09 |
| NBPF20 | ENSG00000162825 | 1 | Neuroblastoma Breakpoint Family, Member 20 | 3.029199621 | 8.163566761 | 0.013076519 |
| TOR1AIP2 | ENSG00000169905 | 1 | torsin 1A interacting protein 2 | 3.84681594 | 14.38821722 | 6.11E−19 |
| PPP1R2 | ENSG00000184203 | 3 | protein phosphatase 1 regulatory inhibitor subunit 2 | 4.073227898 | 16.83308732 | 1.35E−07 |

4. ABX464 Upregulates miR-124

Figure 3:
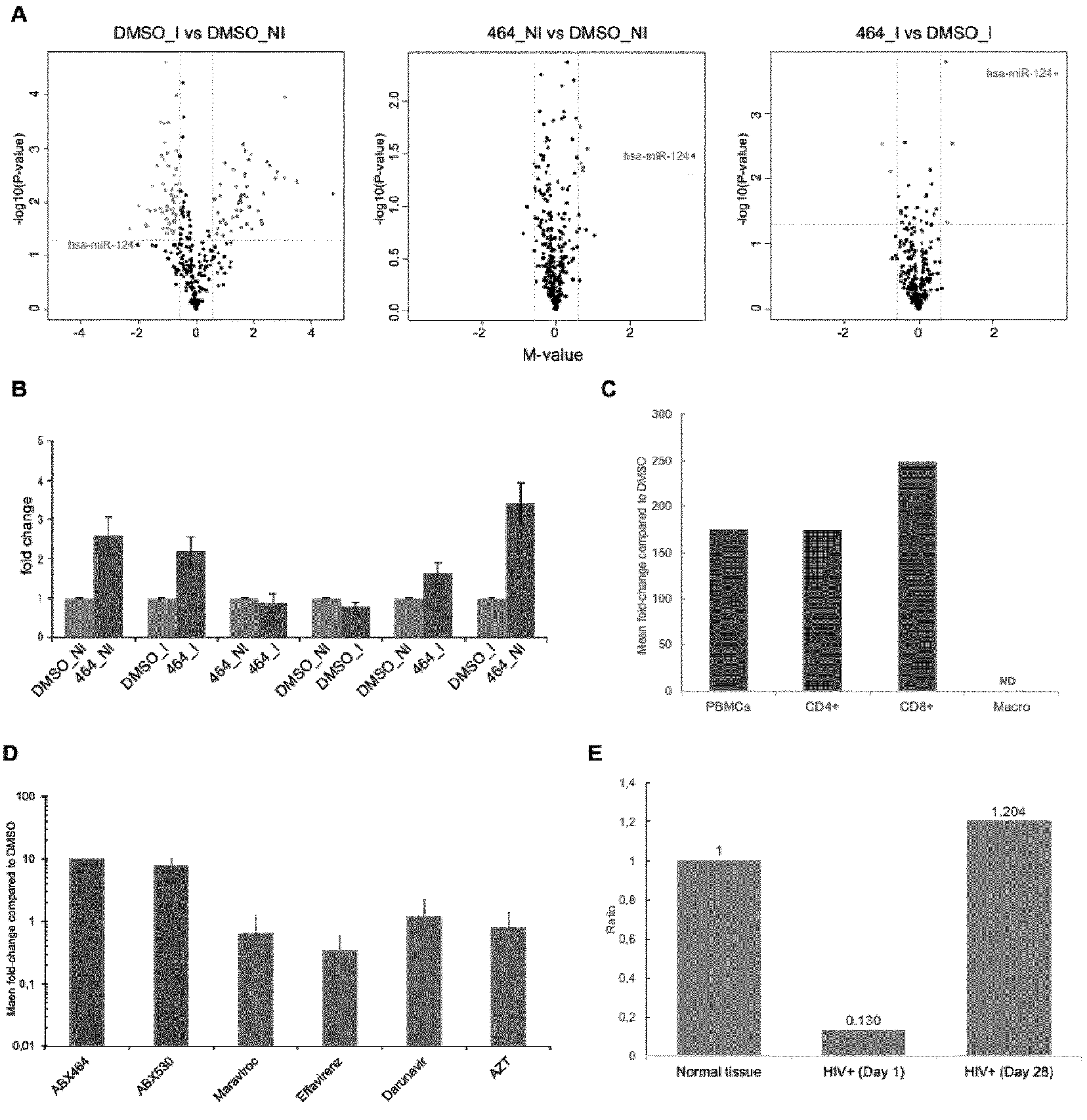
FIG. 3 depicts that ABX464 upregulates a single microRNA, the anti-inflammatory miR-124. A. Microarray analysis of small RNAs from PBMCs from 6 donors. PBMC were infected with the YU-2 strain (I) or uninfected (NI) and treated with ABX464 or untreated (DMSO). Volcano plots show that infection leads to large variations in small noncoding RNAs (left panel), whereas ABX464 induced a reproducible upregulation of a single microRNA, miR-124, in infected and uninfected cells (right and middle panels, respectively). B. Quantification of miR-124 expression using TaqMan Low Density Array technology in CD4+ T cells under the same conditions as in A. C. Expression of miR-124 measured by qPCR in PBMCs, purified CD4+ and CD8 T cells, and macrophages treated with ABX464 in comparison to untreated cells (DMSO, fold change). D. Expression of miR-124 in PBMCs treated with the antiretrovirals ABX464. ABX530, maraviroc, efavirenz, darunavir and AZT compared to untreated cells (DMSO, fold change). E. Quantification of miR-124 in rectal biopsies of healthy participants (n=10) and HIV patients undergoing ART at days 1 and 28 of treatment with ABX464 (n=9). Individual graphs show the results for each patient in comparison with the results for healthy participants.
Figure 9C:
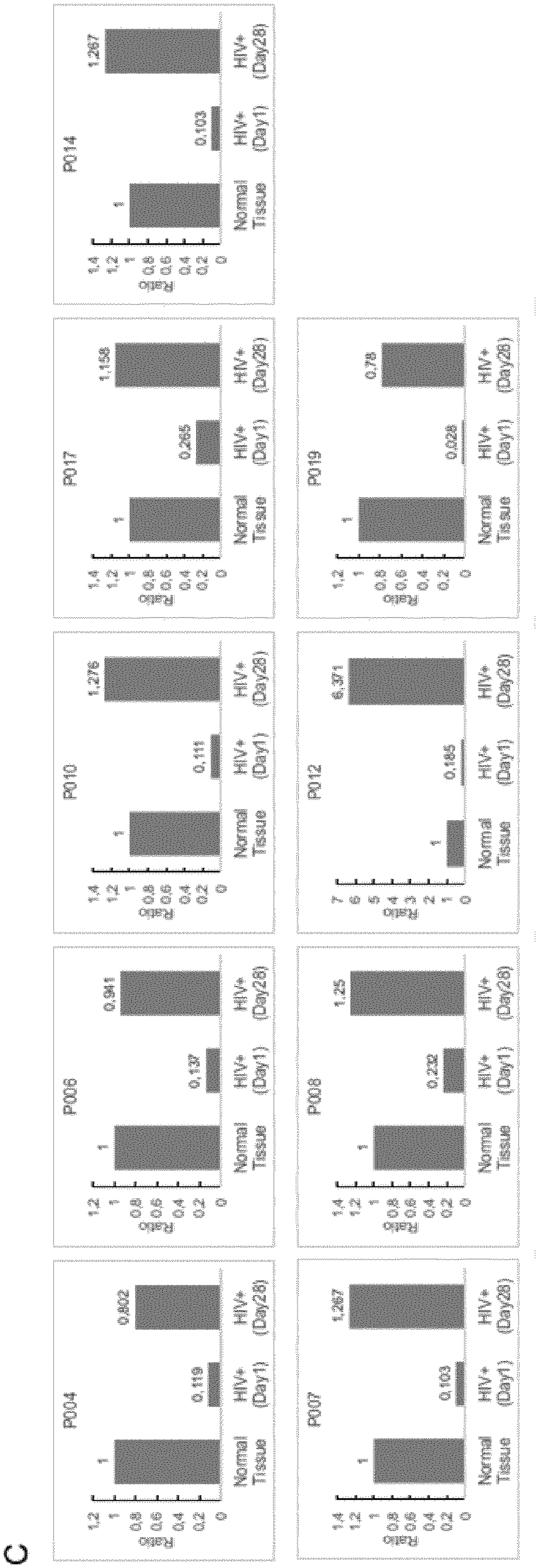
FIG. 9 depicts analysis of the effect of ABX464 treatment on miRNA expression. A, miRNA expression profiling of PBMCs from 6 donors using TaqMan Low Density Array (TLDA). The volcano plots show the differential miRNA expression in PBMCs treated vs. untreated with ABX464 (left panel), and infected vs. uninfected (right panel). B. Comparison of miR-124 expression in macrophages of 6 donors using TaqMan PCR. C. Quantification of miR-124 in biopsies of healthy volontaries (Normal tissue), HIV-infected patients undergoing ART after 28 days of ABX464 treatment (HIV+ Day1) and 28 days later (HIV+ Day 28). D. Quantification of miR-124 in biopsies of HIV patients undergoing ART at day 1 (D1) and day 28 (D28) of treatment and 28 days after stopping the treatment (D56).
Figure 9D:
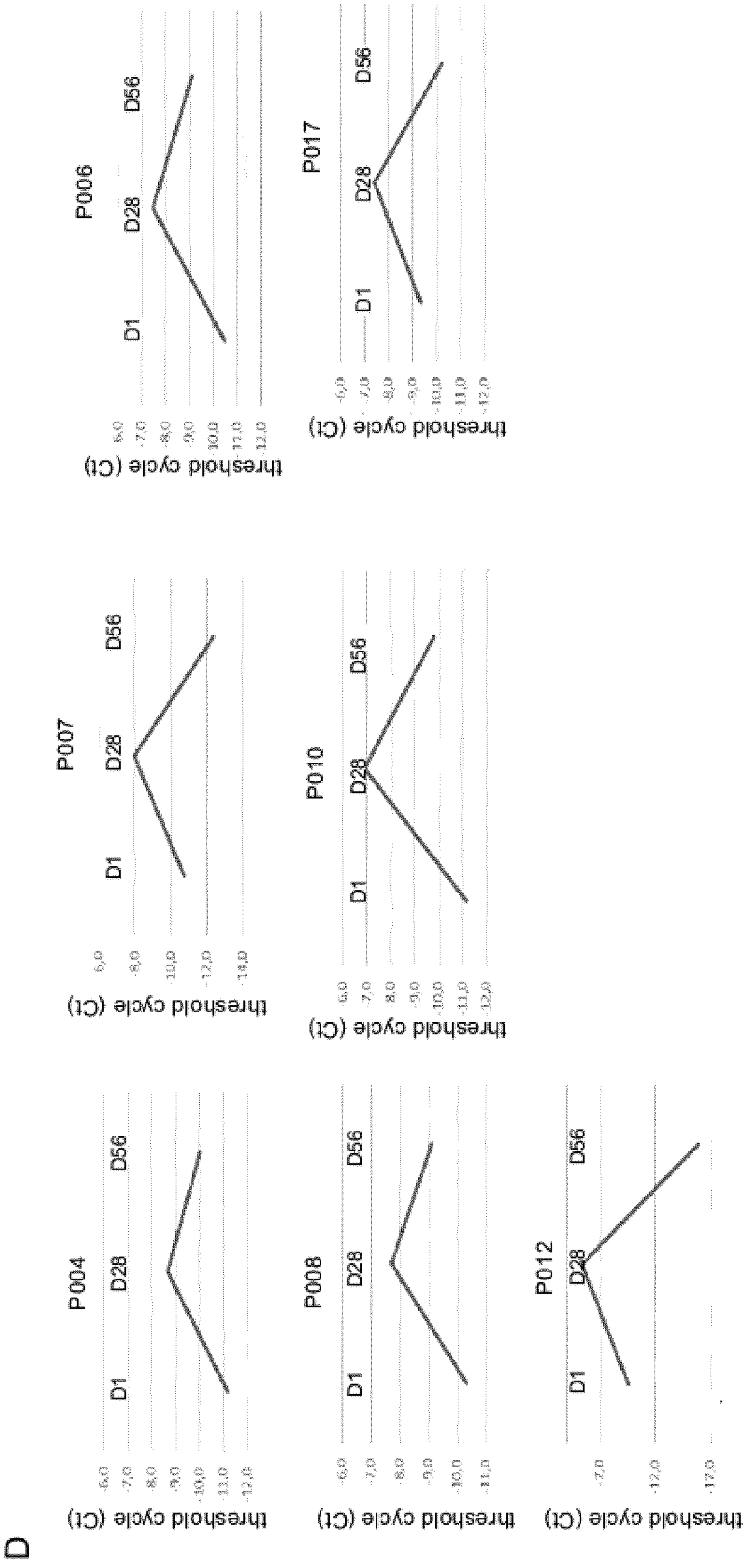

Since the CBC complex, which is targeted by ABX464, is involved in the biogenesis of small noncoding RNAs, and our global analysis thus far did not include these, we decided to evaluate if miRNAs or small nucleolar RNAs (snoRNAs) were differentially regulated by ABX464. We performed a microarray analysis for these RNAs from the PBMCs of 6 donors. Cells that were infected with the YU-2 strain, followed by treatment with ABX464 were compared with uninfected and untreated controls. A total of 104 human miRNAs and 40 snoRNAs were significantly differentially expressed in infected PBMCs, when compared to uninfected PBMCs (data not provided), with a false discovery rate lower than 0.05 and fold change higher than 1.5. The cluster analyses revealed complete separation of the infected and uninfected samples based on the expression profiles of the differentially expressed miRNAs (FIG. 3A). While infection led to this substantial variation in the expression of small noncoding RNAs (FIG. 3A, left panel), ABX464 treatment induced reproducible upregulation of a single microRNA, miR-124, in infected and uninfected cells (FIG. 3A, middle and right panels respectively). To confirm this result, we used another method of profiling microRNA, the TaqMan Low Density Array (TLDA), which is based on reverse transcription real-time PCR, with a screening capacity for 760 miRNAs (FIG. 9A). Again, only miR-124 was observed to be upregulated by ABX464. Furthermore, quantitative PCR of total RNA isolated from infected and uninfected PBMCs of 5 donors demonstrated that infection led to a slight reduction in miR-124 expression (FIG. 3B, also visible in the total analysis in FIG. 3A), but treatment with ABX464 resulted in significant upregulation of miR-124 in both infected and uninfected cells (FIG. 3B). Next, we determined whether the observed miR-124 response to ABX464 treatment in PBMCs could be attributed to specific cell types. Using purified CD4+, CD8 and macrophages cells, we found that ABX464 treatment resulted in upregulation of miR-124 in lymphoid cells (FIG. 3C) but not in monocyte-derived macrophages, where the expression of miR-124 was undetectable (FIG. 3C, FIG. 9B). Finally, we proved that this upregulation of miR-124 is specific to the ABX class of small molecules, since other antiretrovirals such as maraviroc, efavirenz, darunavir and AZT did not upregulate the expression of miR-124 in PBMCs, whereas ABX530, a molecule that has the same properties as ABX464, induced upregulation of miR-124 to a similar extent as ABX464. (FIG. 3D).

In recent years, miR-124 has emerged as a critical modulator of immunity and inflammation. miR-124 is known both as a key regulator of microglia quiescence in the central nervous system and as a modulator of monocyte and macrophage activation. miR-124 also plays a critical role in both innate and adaptive immune response. In particular, miR-124 was shown to be a critical mediator of cholinergic anti-inflammatory action by reducing IL-6, TNF-α and MCP-1 production. Interestingly, IL-6, TNF-α and MCP-1 were upregulated in the commonly used DSS-induced experimental mouse model of colitis, whereas ABX464 reduced the expression of these proinflammatory cytokines. Persistent immune activation and systemic inflammation also play central roles in the pathogenesis of HIV disease. Many HIV-infected individuals treated with antiretroviral therapy (ART) exhibit residual inflammation associated with non-AIDS-related morbidity and mortality. Based on the observed downregulation of miR-124 expression upon HIV infection of PBMCs or CD4+ T cells, and subsequent upregulation with ABX464 treatment, we decided to examine if similar modulation of miR-124 expression was seen in HIV patients undergoing antiretroviral therapy (ART). Since the chronic inflammatory state in patients receiving combination ART is primarily related to the extent of damaged gut-associated lymphoid tissue, miR-124 expression was monitored in rectal biopsies from HIV-infected patients undergoing ART and treated with ABX464 (N=9). miR-124 expression was downregulated in HIV patients treated with ART, in comparison to its expression in colon biopsies from healthy donors (N=10). Treatment with ABX464 for 28 days restored the expression of miR-124 to the level of healthy donors (FIG. 3E). When ABX464 treatment was stopped for 28 days, the expression of miR-124 decreased to reach the level seen before treatment (FIGS. 9C and D), indicating that the changes observed in expression were specifically due to ABX464. Thus, ABX464 modulates the expression of miR-124 both in vitro and in HIV patients.

Figure 4A:
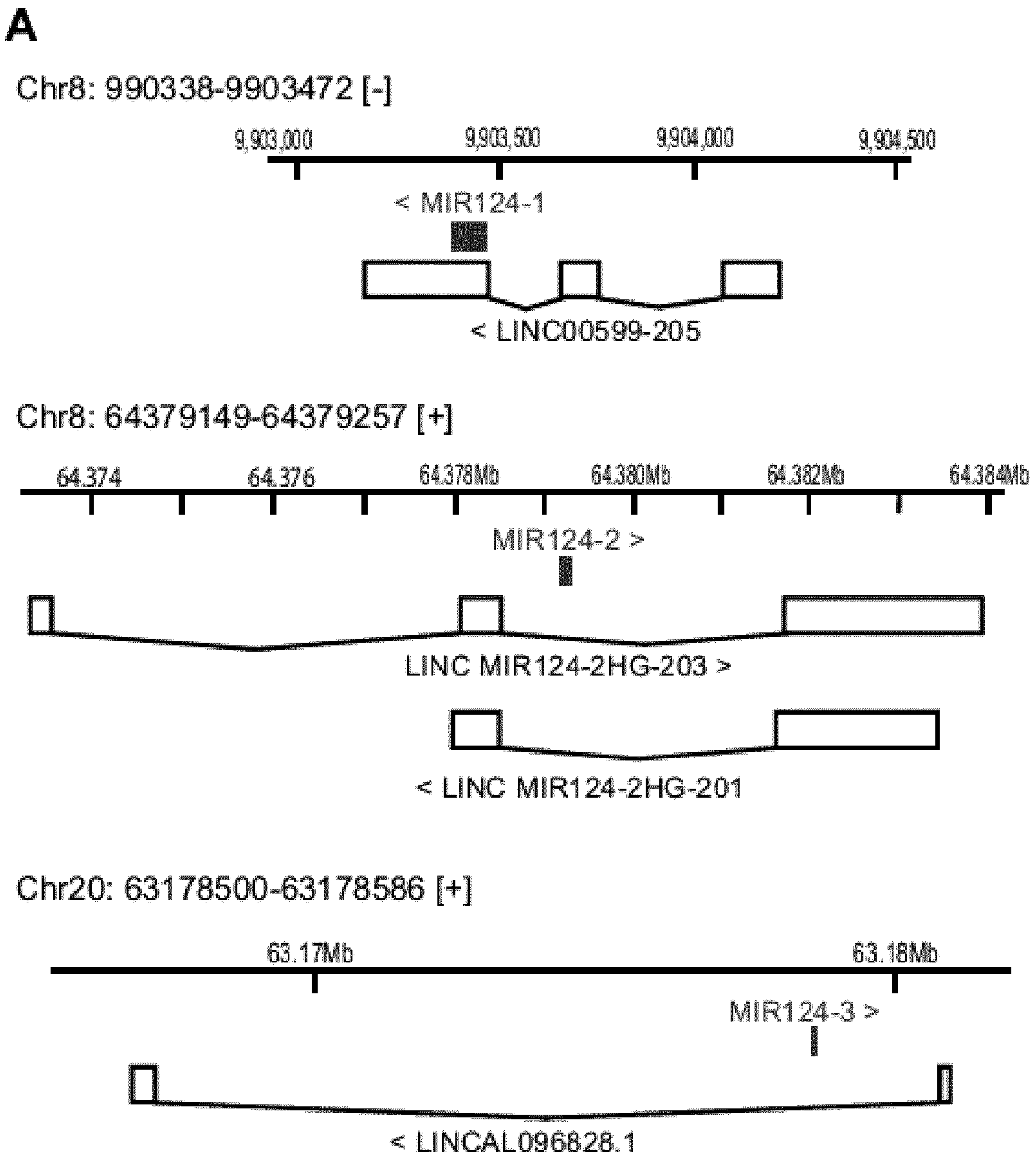
FIG. 4 depicts that miR-124 upregulation by ABX464 originates from splicing of a long noncoding RNA at the miR-124-1 locus. A. There are three genes encoding miR-124, miR-124-1, miR-124-2, and miR-124-3, located on chromosomes 8 and 20 in the human genome. B. We employed a targeted RNA capture and sequencing strategy to determine which gene was induced by ABX464. In both infected and uninfected cells, treatment with ABX464 leads to upregulation of miR-124 from the miR.124.1 locus, whereas a control locus, miR-429, is not affected. C. Locus miR-124-1 contains a long noncoding RNA (LncRNA 0599-205) whose splicing is stimulated by ABX464. D. Counts of the reads at splice junctions (J1, J2, J3 and J4), exon-exon (J5 and J6) and the miR-124 75 bp region (miR-124) quantified by RNA CaptureSeq in PBMCs treated with ABX464.
Figure 4B:
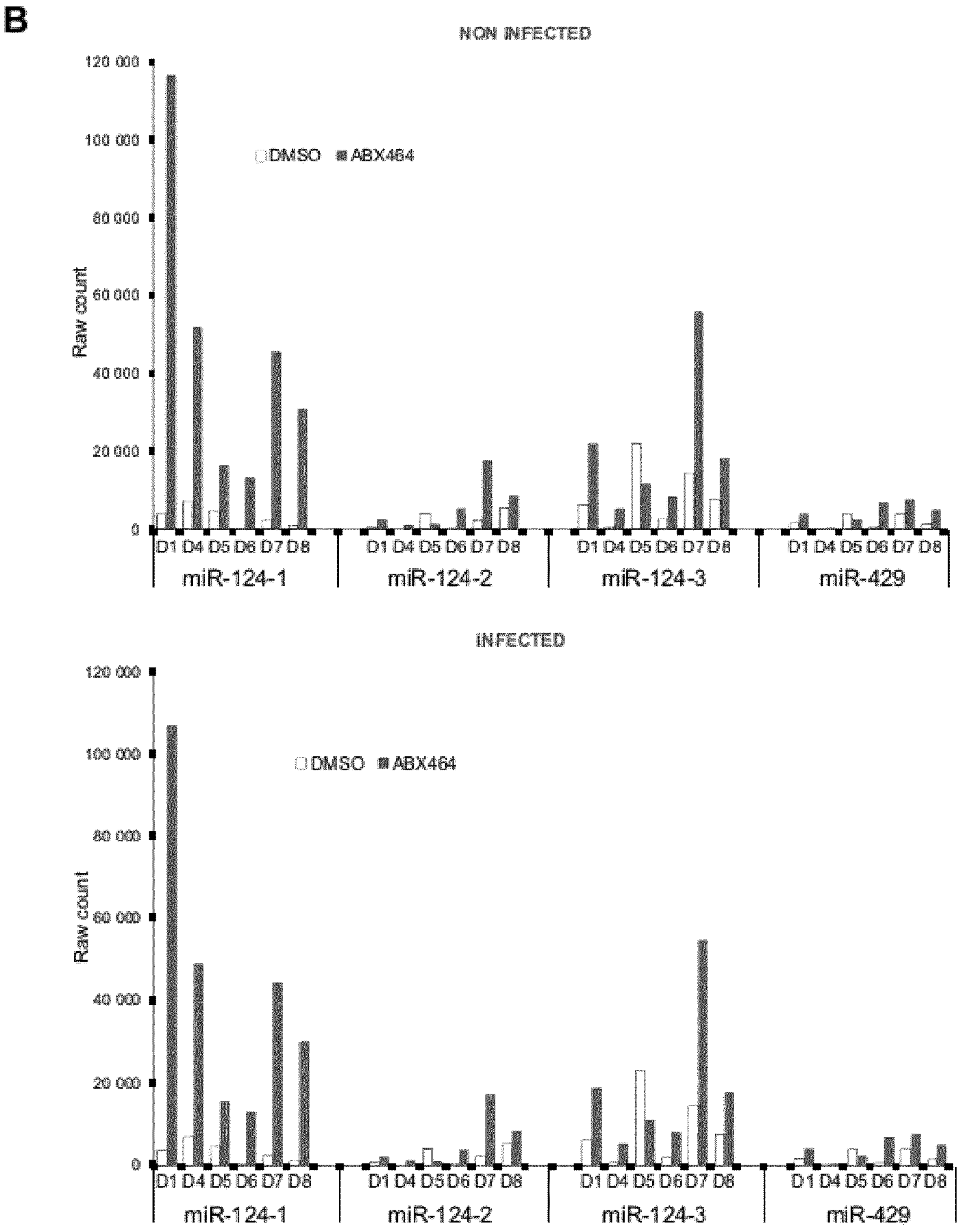

5. ABX464-Induced Splicing of a Long Noncoding RNA at the miR-124-1 Locus Results in Upregulation of miR-124 miR-124 is encoded from three independent genes, miR-124-1, miR-124-2, and miR-124-3, located on human chromosomes 8 and 20 (FIG. 4A). To determine which of these genes is induced by ABX464, we employed targeted RNA CaptureSeq to assess the full depth of the transcriptome. The increased sequencing depth of RNA CaptureSeq together with ab initio transcript assembly was employed to determine which locus is affected by ABX464 treatment (FIGS. 4 A and B). We reconstructed all transcripts assembled within the precapture RNA-Seq data with a similar uniformity of transcript coverage (100% of transcript chains reconstructed; FIGS. 4 A and B). The total number of reads for untreated as well as ABX464 treated samples varied between 2 and 30 million in infected and uninfected PBMCs (Table V). The number of reads from the three loci encoding miR-124 in the treated samples were 4- to 12-fold higher than in the untreated samples (FIG. 4B, Table V), confirming that ABX464 led to a large increase in miR-124. In contrast, ABX464 had no effect on the expression of miR-429 (FIG. 4B), located outside the miR-124 region, again showing the specificity of ABX464 in targeting miR-124.

Most of the aligned reads from the 10-kb regions of each locus originated from miR-124-1 and miR-124-3, whereas the number of aligned reads from miR-124-2 was quite low even after ABX464 treatment (FIG. 4B). The effect of ABX464 on the expression of miR-124 was most pronounced from the miR-124-1 locus (FIG. 4B). All mapped reads from the miR-124-1 locus in the treated samples aligned to miR-124 and a 2 kb region surrounding it. Close inspection of this region indicated that the miR-124 sequence is embedded in a long noncoding RNA (lncRNA 0599-205) at the miR-124-1 locus (FIGS. 4 A and C).

The sequencing depth of RNA CaptureSeq permitted us to assemble ab initio transcripts exhibiting a complex array of splicing patterns. This approach revealed that splicing of lncRNA 0599-205 is activated by ABX464, and this splicing was not present in untreated samples (FIGS. 4C and D). Most of the contigs in the untreated samples aligned with unspliced lncRNA 0599-205. Mapping the reads at the splice junctions (J1, J2, J3 and J4) and exon-exon junctions (J5 and J6) of this lncRNA allowed quantification of spliced and unspliced RNA in the treated samples (FIG. 4D). After 8 days of treatment with ABX464, which we assumed would be enough time for the transcripts to reach steady-state levels, the level of unspliced RNA was nine times higher than that of spliced RNA. Since spliced RNA is more stable than unspliced RNA, we must consider that spliced lncRNA 0599-205 is a source of miR-124 upregulation and therefore becomes less stable. Consistent with this prediction, we found that miR-124 production (reads that mapped to only the 85 bp miR-124 region) compensated for the lack of spliced lncRNA 0599-205 (FIG. 4D).

Table V shows read counts for the three genes encoding miR-124; mir124.1, mir124.2 and mir124.3 in PBMCs either untreated (D1_DMSO, D4_DMSO, D5_DMSO, D6_DMSO, D7_DMSO and D8_DMSO) or treated with ABX464 (D1_464, D4_464, D5_464, D6_464, D7_464 and D8_464).

TABLE V

| LIB names | Total reads | mir124.1 | mir124.2 | mir124.3 |
|---|---|---|---|---|
| D1_DMSO | 4 879 559 | 116164 | 2580 | 21900 |
| D4_DMSO | 30 505 238 | 51798 | 1204 | 5306 |

TABLE V-continued

| LIB names | Total reads | mir124.1 | mir124.2 | mir124.3 |
|---|---|---|---|---|
| D5_DMSO | 1 939 172 | 16352 | 1440 | 11709 |
| D6_DMSO | 4 385 103 | 13294 | 5358 | 8498 |
| D7_DMSO | 7 279 017 | 45480 | 17676 | 55708 |
| D8_DMSO | 8 381 026 | 30950 | 8830 | 18253 |
| D1_464 | 7 884 109 | 4014 | 704 | 6439 |
| D4_464 | 30 363 868 | 7114 | 4 | 701 |
| D5_464 | 26 874 233 | 4748 | 4222 | 21941 |
| D6_464 | 2 927 628 | 324 | 362 | 2542 |
| D7_464 | 14 803 409 | 2486 | 2326 | 14460 |
| D8_464 | 17 386 693 | 1088 | 5452 | 7772 |

6. Splicing of lncRNA 0599-205 is Required for the Production of miR-124

To directly assess the contribution of lncRNA 0599-205 to the production of miR-124, we cloned the genomic sequence of chromosome 8 from 9 903 167 through 9 904 210 of lncRNA 0599-205 into a plasmid vector (FIG. 5A). Both the spliced and unspliced transcripts of lncRNA 0599-205 could be readily detected in the transfected HeLa cells (FIG. 5B). However, we failed to detect an upregulation of miR-124 in transfected HeLa cells in response to ABX464 treatment since splicing is maximized in HeLa cells and the CBC complex would have an effect at the site of transcription (FIG. 5B). However, transient transfection of the plasmid into HeLa cells resulted in a dramatic (1 250-fold) increase in miR-124 levels (FIG. 5C, left panel). In contrast, when the splice sites of the lncRNA 0599-205 are mutated only traces of miR-124 are detected (FIG. 5C, left panel). Consistent with the fact that unpliced lncRNA 0599-205 are less stable, the amount of mutated lncRNA 0599-205 is less than wild type (FIG. 5C, right panel). All together, the results demonstrate that splicing of the lncRNA 0599-205 is a prerequisite for the production of mir-124.

Discussion

Figure 5:
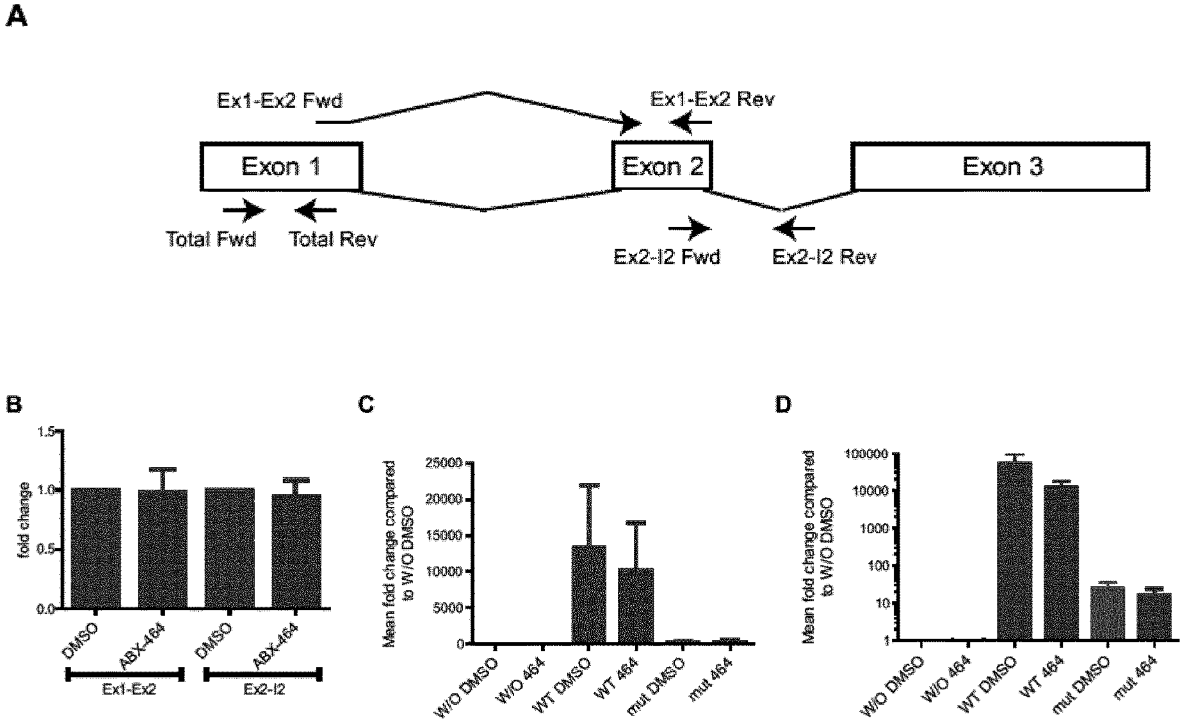
FIG. 5 depicts that splicing of LncRNA 0599-205 is required for the production of miR-124. A. Schematic representation of LncRNA 0599-205 precursor and primers used to amplify different derived RNAs. B. Quantification of spliced and unspliced LncRNA 0599-205 in the presence or absence of ABX464. C. Quantification of the expression of miR-124 following transfection of a wild type and splicing mutant of lncRNA0599-205 plasmids in HeLa cells in the presence or absence of ABX464. D. Quantification of total wild type and splicing mutant lncRNA0599-205 in the presence or absence of ABX464.

Our investigation provides new insights into the mechanism of action of ABX464 in upregulating the anti-inflammatory miR-124 in treated UC patients and inhibition of viral replication in HIV patients. ABX464 binds CBC (ABIVAX, data in file), a complex that stimulates processing reactions of capped RNAs, including their splicing, 3'-end formation, degradation, and transport. Given that the CBC is believed to bind all classes of m7G-capped RNAs, including precursors and mature forms of mRNAs, stable long noncoding RNAs (lncRNAs), nonadenylated histone RNAs, and precursors of spliceosomal small nuclear RNAs (snRNAs), it is important to understand how the binding of ABX464 to CBC complex achieves its specificity. Both the variation of splicing of HIV RNAs and lncRNA 0599-205 are robustly induced by ABX464. We don't know the reason for that. It could be that weak splice sites that characterizes both transcripts, is at the origin of the induction of these splicing events by ABX464-CBC complex. Before to be exported to cytoplasm most of human protein coding genes are spliced, if not they are degraded in the nucleus, and in the cytoplasm a pioneer round of translation is important for mRNA quality control. The lncRNA 0599-205 like any RNA in the cell will be degraded or stay at its site of transcription which is the case of many long coding RNA. The miR-124 sequence is at the 3rd exon of lncRNA 0599-205, this is also a peculiar situation because most of microRNA are generally classified as "intergenic" or "intronic" based upon their genomic location. Intergenic miRNAs are known to be transcribed as independent transcription units, while intronic miRNAs are believed to be processed from the introns of their hosting transcription units and hence share common regulatory mechanisms and expression patterns with their host genes. Since ABX464 treatment did not induce any variation of the microRNA other than miR-124 and very little variation of expression of genes that might host microRNA, we believe that ABX464-CBC interaction induces a specific effect of viral RNA and miR-124 biogenesis. This latter point is also demonstrated by the fact that miR-124 is transcribed by 3 loci but only the miR-124.1 locus is affected by ABX464 treatment and also the splicing of lncRNA 0599-205 is required for the production of miR-124 (FIG. 5).

Nuclear cap functions are mediated by the CBP80 and CBP20 proteins, which associate cotranscriptionally with the nascent RNA. CBP20 interacts directly with the m7G cap through its classical RNA recognition motif (RRM), while CBP80 ensures high-affinity binding of the full CBC and provides a platform for interactions with other factors. We have demonstrated that ABX464, by binding the CBC, prevents the production of the unspliced viral RNA required for viral replication and induces the production of miR-124 from lncRNA-0599-205. However, ABX464 had a negligible impact on cellular splicing. Therefore, ABX464 acts as an enhancer of viral but not cellular splicing. Binding of ABX464 may change the conformation of the CBC to allow efficient interaction of CBP80 with a splicing factor and thereby render recognition of the viral splicing sites more efficient. It is known that HIV RNA has suboptimal splicing sites to allow inhibition of splicing of the 9 kb primary transcript at later stages of infection. In contrast, most cellular genes require splicing for expression, and unspliced intron-containing transcripts are retained in the nucleus where they are degraded. Depletion of NCBP1 by 50% leads to upregulation of unspliced IR transcripts confirming the implication of CBC in NMD. ABX464 is making sure that viral HIV RNA is spliced (since it is transcribed from integrated pro viral DNA resembling any gene in the cell), exported and unspliced viral RNA is degraded (presumably by NMD). ABX464 is not changing any of CBC functions therefore it is not expected that ABX464 by binding the CBC complex change the general RNA biogenesis in the cell. However, very little is known about CBC complex under HIV infection or immune cells activation. The finding that ABX464 binds to CBC and induce specific changes in immune cells; miR-124 overexpression by modulating the splicing 0599-205 long coding RNA and enhancement of splicing of HIV RNA, will be of great help to understand the involvement of CBC under HIV infection and inflammation.

A prediction of splice site strength using maximum entropy (MaxEnt) revealed that the 5' splice site between exon 2 and intron 2 of lncRNA 0599-205 is very weak compared to the other splice site (Table VI). Since unspliced lncRNA 0599-205 cannot exit the nucleus due to quality control machinery and CBC-mediated control, spliced lncRNA 0599-205 constitutes a miRNA storage form, possibly in addition to other functional properties of the intact spliced transcript. This storage may be maintained through low transcriptional and degradative activity of unspliced lncRNA 0599-205 and producing only low levels of mature miR-124 release under normal conditions. Indeed, when lncRNA 0599-205 is unspliced, its fate is similar to that of other short-lived transcripts, susceptible to a CBC complex called CBC-NEXT, which promotes RNA degradation via the nuclear RNA exosome. Consistently, the splicing of lncRNA 0599-205 is a prerequisite for the production of miR-124. The splicing of lncRNA 0599-205 is important to stabilize the mature transcript for recognition by the microRNA processing machinery and thereby produce miR-124. ABX464 treatment could, thus, enable the rapid release of a large amount of miR-124 through lncRNA 0599-205 splicing without requiring transcriptional activation of the lncRNA 0599-205 locus. In HIV patients this could be the mechanism by which miR-124 is up-regulated following treatment with ABX464 (FIG. 3E).

HeLa cells, which contain a large excess of splicing factors, efficiently produce HIV viral RNA splice products and a large amount of miR-124 from transfected HIV and lncRNA 0599-205 constructs, respectively. Thus, ABX464 does not impede the normal function of CBC in splicing but renders it more efficient. As viral but not cellular genes require the unspliced state for viral replication, and splicing of lncRNA 0599-205 can affect miR-124 expression, ABX464 inhibits viral replication and induces anti-inflammatory miR-124 expression. Large numbers of studies in different cells and systems have found that miR-124 is a critical modulator of inflammatory and immunological responses. The finding that ABX464 upregulates miR-124 expression in infected patients could be a major advantage in treating residual inflammation associated with non-AIDS-related morbidity and mortality in HIV patients. In many cases, miR-124 functions as a negative regulator for inflammatory signals, providing negative feedback to help maintain homeostasis. Furthermore, Ulcerative colitis patients treated with ABX464 also demonstrate elevation of miR-124 and show evidence of a robust and consistent efficacy signal of ABX464. Thus, ABX464 is a small molecule with therapeutic potential not only against HIV, but also against inflammatory diseases.

Table VI shows prediction of splice site strength using maximum entropy (MaxEnt). MAXENT scores of 5' splice sites and 3' splice sites at the exon1-intron1-exon2 (Exon1-Exon2 ss) and exon2-intron2-exon3 (Exon2-Exon3 ss) boundaries.

TABLE VI

| | 5' ss sequence | MAXENT score | 3' ss sequence | MAXENT score |
|---|---|---|---|---|
| Consensus | CAG/guaagu | 10.86 | ugucccuuuuuuuuccacag/CUG | 12.6 |
| Exon1-Exon2 ss | GAG/guaaag | 9.65 | uccuccuuuccuuuccucag/GAG | 11.46 |
| Exon2-Exon3 ss | GCG/gcggga | -4.66 | uccuccuuuccuuccucag/GAG | 11.46 |

The invention claimed is:

1. An in vitro or ex vivo method of selecting at least one patient for a therapeutic treatment of an inflammatory disorder, which is inflammatory bowel disease, the method comprising a) detecting a level of expression of miR-124 as a biomarker in a biological sample collected from a patient and comparing to a control reference value, wherein the control reference value is measured in a control sample, which is taken from a set of normal, non-diseased members of a population, or from the least one patient prior to the presence of inflammatory bowel disease, b) selecting the at least one patient for the therapeutic treatment of the inflammatory disorder bowel disease, wherein a reduced expression level of miR-124 was detected in the biological sample of the at least one patient, and c) administering the therapeutic treatment to the at least one patient, wherein the therapeutic treatment includes ABX464 of Formula I

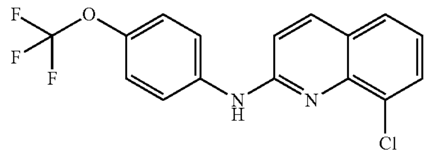 [SMILES: FC(F)(F)Oc1ccc(Nc2ccc3cccc(Cl)c3n2)cc1]

8-chloro-N-(4-(trifluoromethoxy)phenyl)quinolin-2-amine I or a pharmaceutically acceptable salt thereof.

2. The in vitro or ex vivo method of selecting at least one patient according to claim 1, wherein the biological sample is a biological fluid, a cell sample, a tissue biopsy, or a plurality of samples from a clinical trial.

3. The in vitro or ex vivo method of selecting at least one patient according to claim 2, wherein the biological fluid is selected from the group consisting of a biological tissue sample, a whole blood sample, a swab sample, a plasma sample, a serum sample, a saliva sample, a vaginal fluid sample, a sperm sample, a pharyngeal fluid sample, a bronchial fluid sample, a fecal fluid sample, a cerebrospinal fluid sample, a lacrymal fluid sample and a tissue culture supernatant sample.

4. The in vitro or ex vivo method of selecting at least one patient according to claim 1, wherein the biological sample is blood.

5. The in vitro or ex vivo method of selecting at east one patient according to claim 1, wherein the inflammatory bowel disease is selected from Crohn's disease and ulcerative colitis.

* * * * *